United States Patent
St Amant, III

(10) Patent No.: US 10,627,322 B1
(45) Date of Patent: *Apr. 21, 2020

(54) MODULAR SAMPLE SYSTEM INCORPORATING MOUNTING BRACKET INDEPENDENT OF HOUSING, AND METHOD THEREFORE

(71) Applicant: Mayeaux Holding, LLC, Gonzales, LA (US)

(72) Inventor: Valmond Joseph St Amant, III, St Amant, LA (US)

(73) Assignee: MAYEAUX HOLDING, LLC, Gonzales, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/179,674

(22) Filed: Nov. 2, 2018

Related U.S. Application Data

(63) Continuation-in-part of application No. 16/005,431, filed on Jun. 11, 2018, which is a continuation-in-part
(Continued)

(51) Int. Cl.
  *G01N 1/22* (2006.01)
  *G01N 33/22* (2006.01)

(52) U.S. Cl.
  CPC ......... *G01N 1/2247* (2013.01); *G01N 1/2226* (2013.01); *G01N 33/225* (2013.01); *G01N 2001/2238* (2013.01)

(58) Field of Classification Search
  CPC ......... B01L 3/502715; B01L 3/502707; B01L 7/00; B01L 2300/0816; B01L 3/563; B01L 2200/027; B01L 2200/0689; B01L 2300/0874; B01L 2200/028; G01N 2035/00326; G01N 35/00693; G01N 35/1095; G01N 1/2214; G01N 30/20;
(Continued)

(56) References Cited

U.S. PATENT DOCUMENTS 3,666,340 A   3/1972   Albeanese, III
3,858,752 A   1/1975   Marvin, Jr. et al.
(Continued)

OTHER PUBLICATIONS

Mustang Sampling LLC, Mustang Intelligent Vaporizer Sampling System Model 2/MIV2, Product Sheet, (C) 2009-2016, vol. 2.6. Mustang Sampling LLC, US.
(Continued)

*Primary Examiner* — Brandi N Hopkins
(74) *Attorney, Agent, or Firm* — Joseph T Regard, Ltd plc

(57) ABSTRACT

A modular sample conditioning system formed for in-situ sampling installation, referenced herein as "source mounted". The present invention relates to a docking platform or substrate configured to receive multiple, diverse sampling components in various flow configurations, coupled with a unique housing/enclosure formed to engage the docking platform so as to further strengthen and stabilize the mount, the enclosure (in rigid and non-rigid, flexible forms) also formed to engage one or more of the mounted sampling components, so as to provide access outside of the enclosure for visibility and/or manual access of same, providing an easily installed and maintained, user-accessible, on-site modular sampling conditioning/monitoring system.

53 Claims, 55 Drawing Sheets

Related U.S. Application Data of application No. 15/615,786, filed on Jun. 6, 2017, and a continuation-in-part of application No. 15/228,814, filed on Aug. 4, 2016, now Pat. No. 10,073,013.

(60) Provisional application No. 62/202,478, filed on Aug. 7, 2015.

(58) Field of Classification Search
CPC ......... G01N 2001/2267; G01N 1/2247; G01N 30/30; G01N 1/2035; G01N 2001/105; G01N 2001/205; F16K 27/12; Y10T 29/4973

See application file for complete search history.

(56) References Cited

U.S. PATENT DOCUMENTS

| | | | |
|---|---|---|---|
| 4,194,657 A | | 3/1980 | Thor |
| 4,688,537 A | | 8/1987 | Calkins et al. |
| 4,821,905 A | | 4/1989 | Ing |
| 5,109,709 A | | 5/1992 | Nimberger |
| 5,501,080 A | | 3/1996 | McManus et al. |
| 5,531,130 A | | 7/1996 | Welker |
| 5,844,123 A | * | 12/1998 | Marsh ................ G01N 33/0042 73/19.12 |
| 6,092,519 A | | 7/2000 | Fish |
| 6,357,304 B1 | | 3/2002 | Mayeaux |
| 6,539,312 B1 | | 3/2003 | Nimberger et al. |
| 6,701,794 B2 | | 3/2004 | Mayeaux |
| 6,827,486 B2 | * | 12/2004 | Welker .................. G01K 13/02 374/147 |
| 6,904,816 B2 | | 6/2005 | Mayeaux |
| 7,004,041 B2 | | 2/2006 | Mayeaux |
| 7,134,318 B2 | | 11/2006 | Mayeaux |
| 7,162,933 B2 | | 1/2007 | Thompson et al. |
| 7,471,882 B2 | | 12/2008 | Peebles et al. |
| 7,886,624 B1 | * | 2/2011 | Mayeaux ............. G01N 1/2035 73/866.5 |
| 8,196,480 B1 | | 6/2012 | Mayeaux |
| D674,052 S | | 1/2013 | Thompson |
| 9,395,280 B2 | | 7/2016 | Thompson et al. |
| 9,459,185 B2 | | 10/2016 | Thompson et al. |
| 10,107,437 B2 | | 10/2018 | Wolfe |
| 2002/0036167 A1 | * | 3/2002 | Mayeaux ............. G01N 1/2035 210/637 |
| 2010/0058881 A1 | | 3/2010 | Braaten |
| 2012/0325694 A1 | | 12/2012 | Thompson |
| 2017/0074693 A1 | | 3/2017 | Wolfe |
| 2017/0234777 A1 | | 8/2017 | St Amant, III |
| 2019/0040988 A1 | | 2/2019 | Wolfe |

OTHER PUBLICATIONS

Mustang Sampling LLC, Mustang Sample Conditioning System/MSCS, Product Sheet, (C) 2009-2016, vol. 1.4, Mustang Sampling LLC, US.

Mustang Sampling LLC, Mustang Sample Conditioning System /P53, Product Sheet, (C) 2009-2016, vol. 2.1, Mustang Sampling LLC, US.

Mustang Sampling, LLC, Mustang PONY Heated Probe Enclosure, Product Sheet, (C) 2009-2016, vol. 4.3, Mustang Sampling LLC, US.

Welker Inc, SCHS Sample Conditioning Heated System, Product Sheet, (C) 2016, vol. 05-16/200, Welker Inc, US.

Intertec-Hess GMBH, Intertec Product Enclosures, web page, www.intertec.info/v2/index.php/en/enclosures. (C) 2014, Intertect-Hess GMBH, Germany.

Emerson Electric Co, Drawing 370XA Multi-Stream Enclosure 72904, www.emerson.com/documents/automation/drawing-370xa-multi-stream-enclosure-en-72904.pdf, Ver 3 Jan. 7, 2016, US.

Emerson Electric Co, Drawing 370XA Multi-Stream Enclosure 72902, www.emerson.com/documents/automation/drawing-370xa-multi-stream-enclosure-en-72902.pdf, Ver 3 Jan. 7, 2016, US.

SpectraSensors Inc, SS500/SS2000/SS3000 Gas Analyzer Installation/Maintenance Manual, (C) 2016, See pp. A-9, A-10, PN 4900002215 Rev D, SpectraSensors Inc, US.

Intertec-Hess GMBY, Intertec Multibox 170, Product Sheet, downloaded Feb. 5, 2018 from /www.intertec.info/documents/en/kd128enpdf, KD128010en,US.

Intertec-Hess GMBY, Intertec Multibox 170, Product Sheet, http://www.bright-technology.ro/files/GRP%20Enclosure/MULTIBOX/MULTIBOX_170.pdf, dated Sep. 17, 2014,KD128-8e0MULTIBOX 170.

Intertec-Hess GMBY, Diabox 87, Product Sheet, dated May 13, 2013, KD222-12en, US.

A+ Corp LLC, Genie GP2 Membrane Probe, Product Sheet, (C) 2012, SCC-GP2-PS_0116, A+ Corp LLC, US.

A+Corp LLC, Genie GPR Probe Regulator, Product Sheet, (C) 2012, SCC-GPR-PS_038, A+ Corp LLC, US.

Intertec Instrumentation, Multibox 80, Product Sheet, dated Sep. 3, 2016, KD126-10ca, US.

Thermon MFG Co, Heated Insulation Jacket, Product Sheet, Mar. 9, 2018, Form PAF0060U-0911, US.

Thermaxx-Products, Thermaxx Jackets, Product Brochure, (C) 2011, US.

Neptech Inc, Flexotherm Heated Blankets, Product Brochure, Feb. 13, 2015, US.

A+ Corp LLC, Genie 760 Direct Drive Probe, Product Sheet, (C) 2012, SCC-780-PS_0116, A+ Corp LLC, US.

A+ Corp LLC, Genie 757 Spot Smpl Assembly, Product Sheet, (C) 2012, SCC0757-PS_1014, A+ Corp LLC, US.

A+ Corp LLC, Kozy Insulators, Product Sheet, (C) 2012, SCC-Kozy-PS_0712, A+ Corp LLC, US.

A+ Corp LLC, Kozy Insulators, Installation Instructions, (C) 2010, A+ Corp LLC, US.

Powerblanket, Pipe, Valve and Manifold Heaters, Product Sheet, 2014, Powerblanket, US.

Mustang Sampling LLC, Mustang Sample Conditioning System/MSCS, Product Sheet, (C) 2009-2017, vol. 1.5, Mustang Sampling LLC, US.

Mustang Sampling LLC, Mustang Sample Conditioning System /P53, Product Sheet, (C) 2009, vol. 1.2, Mustang Sampling LLC, US.

Mustang Sampling LLC, Mustang Pony Heated Probe Enclosure, Product Sheet, (C) 2009, vol. 2.1, Mustang Sampling LLC, US.

Powerblanket, Cover your Assets, 2016 Product Catalog, Jan. 25, 2016, Powerblanket, US.

Third Party Submission filed Sep. 4, 2017 under 37 CFR 1.290 in U.S. Appl. No. 15/258,227, filed Sep. 7, 2016, Wolfe (Inv), 3 Pgs.

Third Party Submission Concise Description of Relevance filed Sep. 4, 2017 Citing 2017/0234777 A1 in U.S. Appl. No. 15/258,227, filed Sep. 7, 2016, Wolfe (Inv), 7 Pgs.

Third Party Submission Concise Description of Relevance per 37 CFR 1.290 filed Sep. 4, 2017 in U.S. Appl. No. 15/258,227, filed Sep. 7, 2016, Wolfe (Inv), 3 Pgs.

* cited by examiner

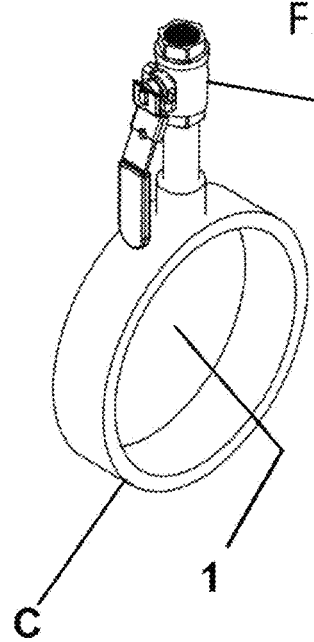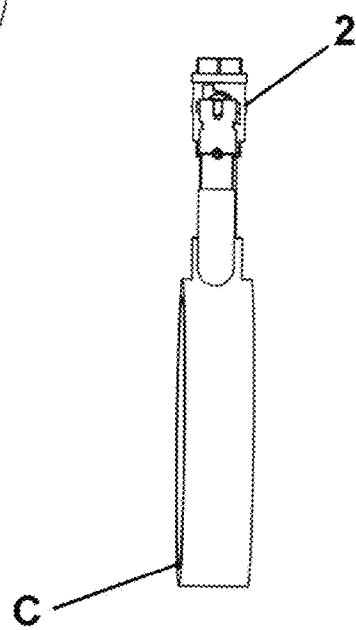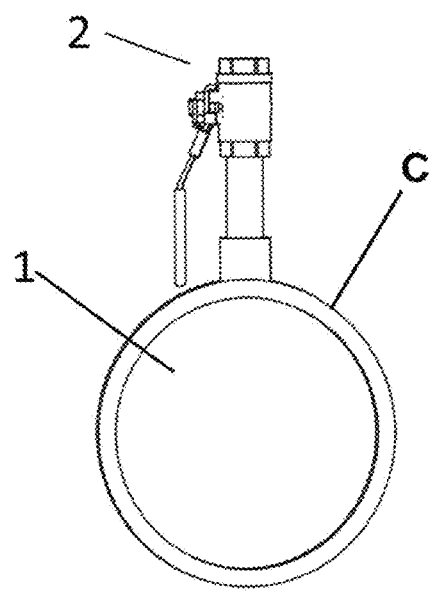

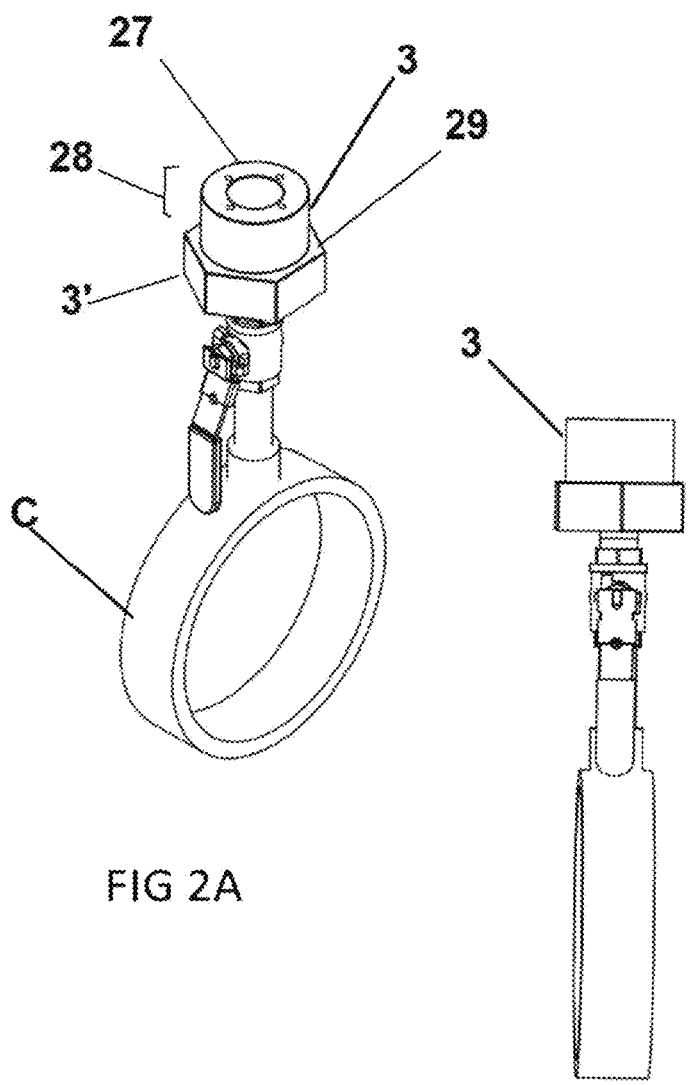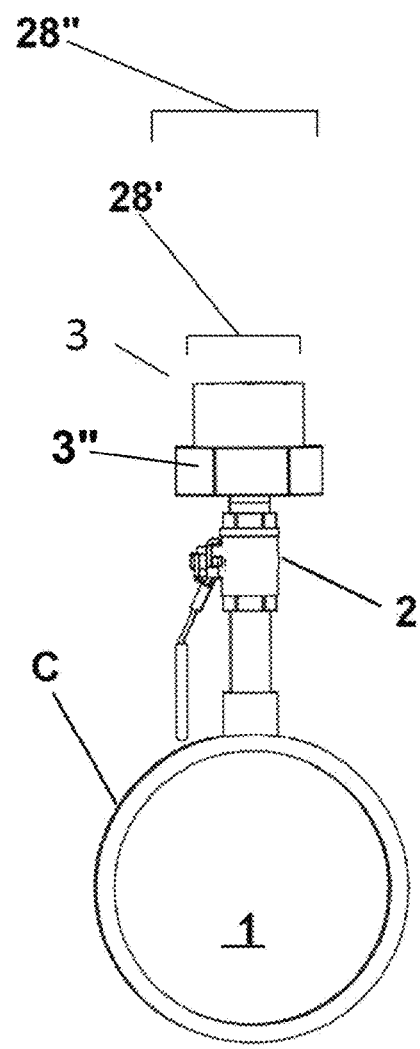
FIG 2A
FIG 2B
FIG 2C

5

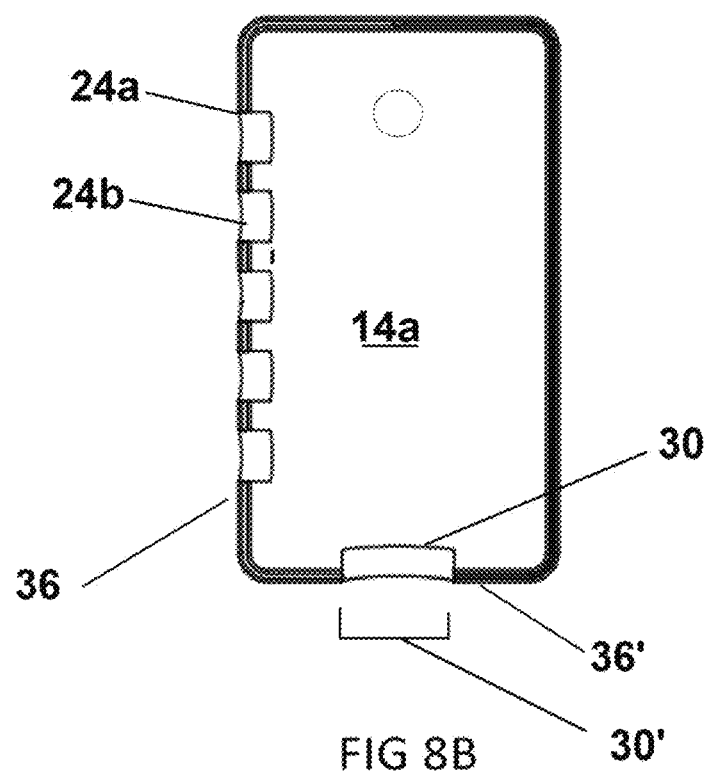

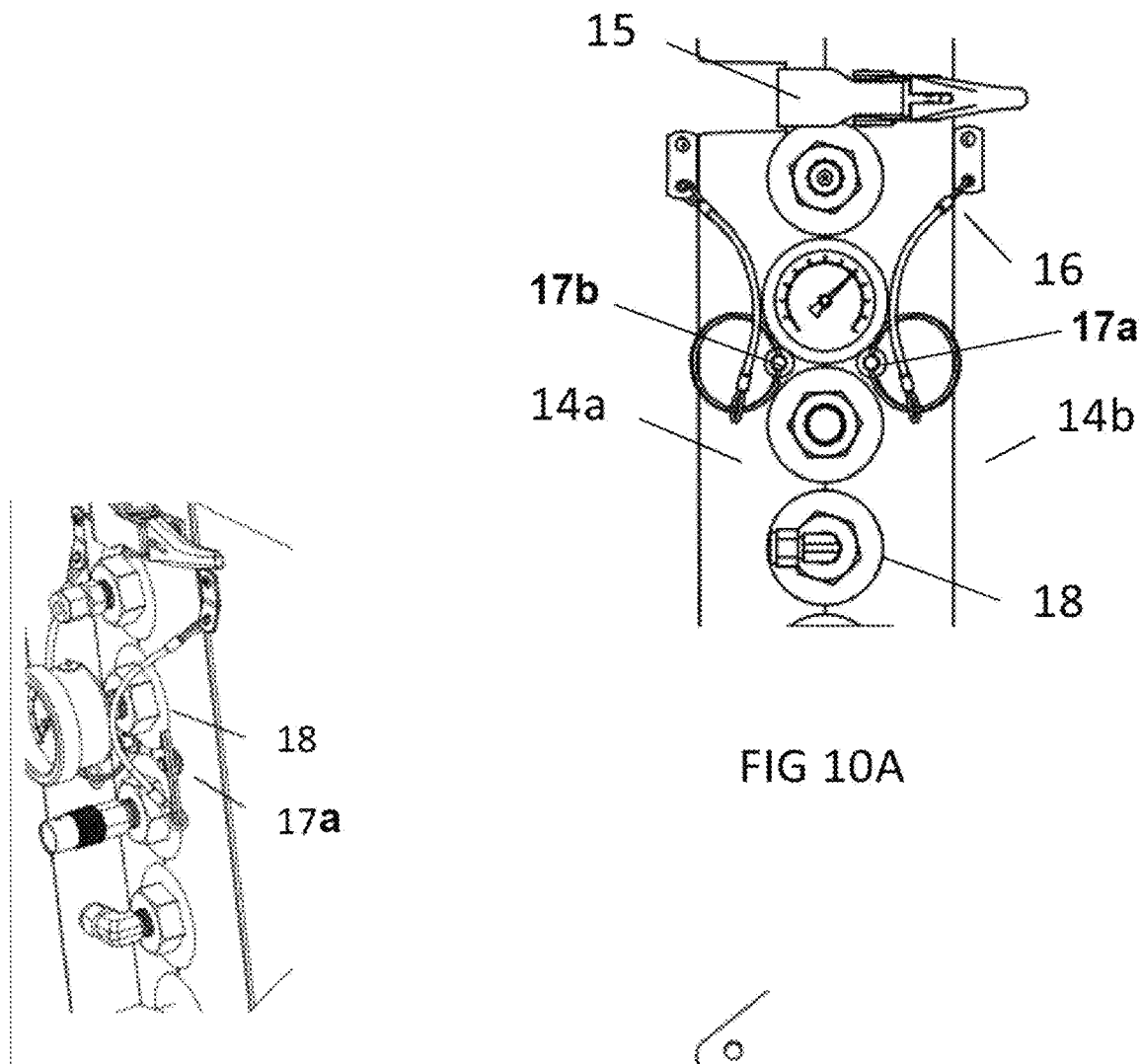
FIG 10A
FIG 10B
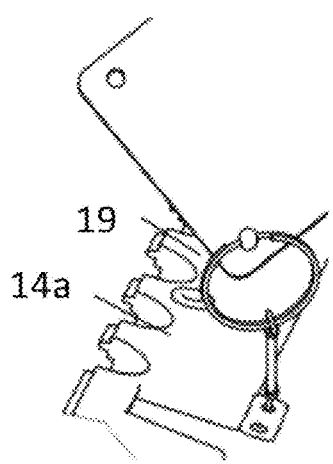
FIG 10C

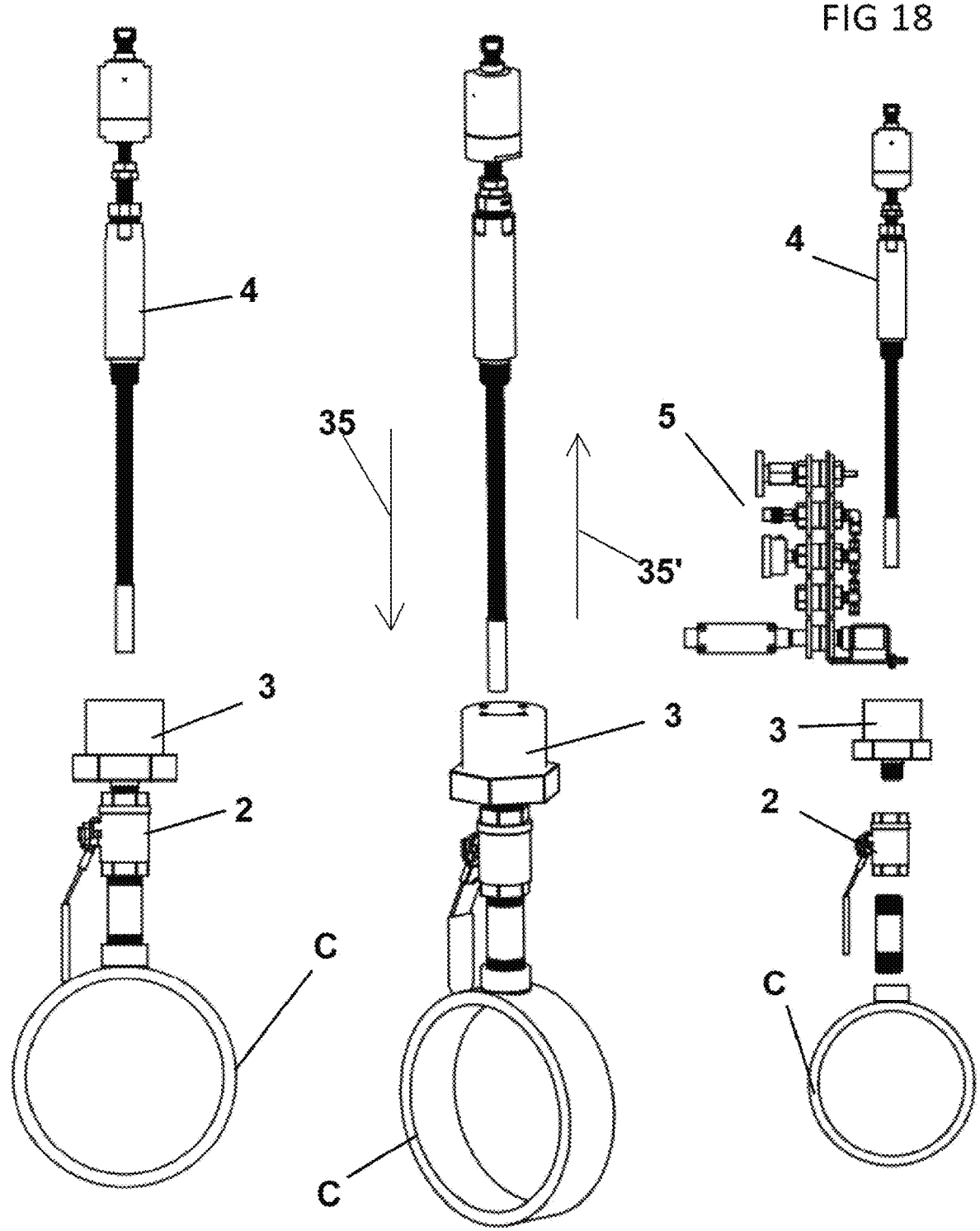

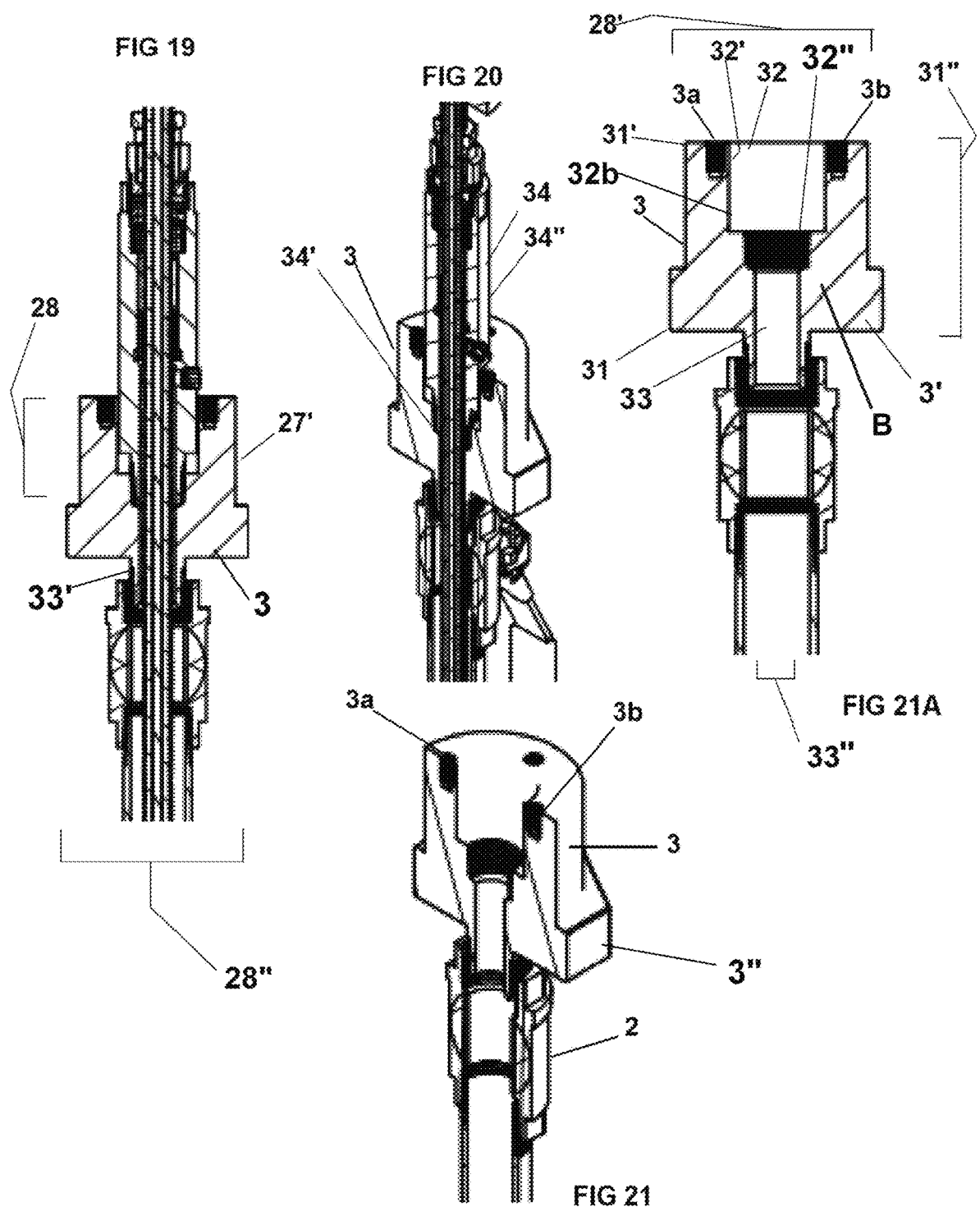

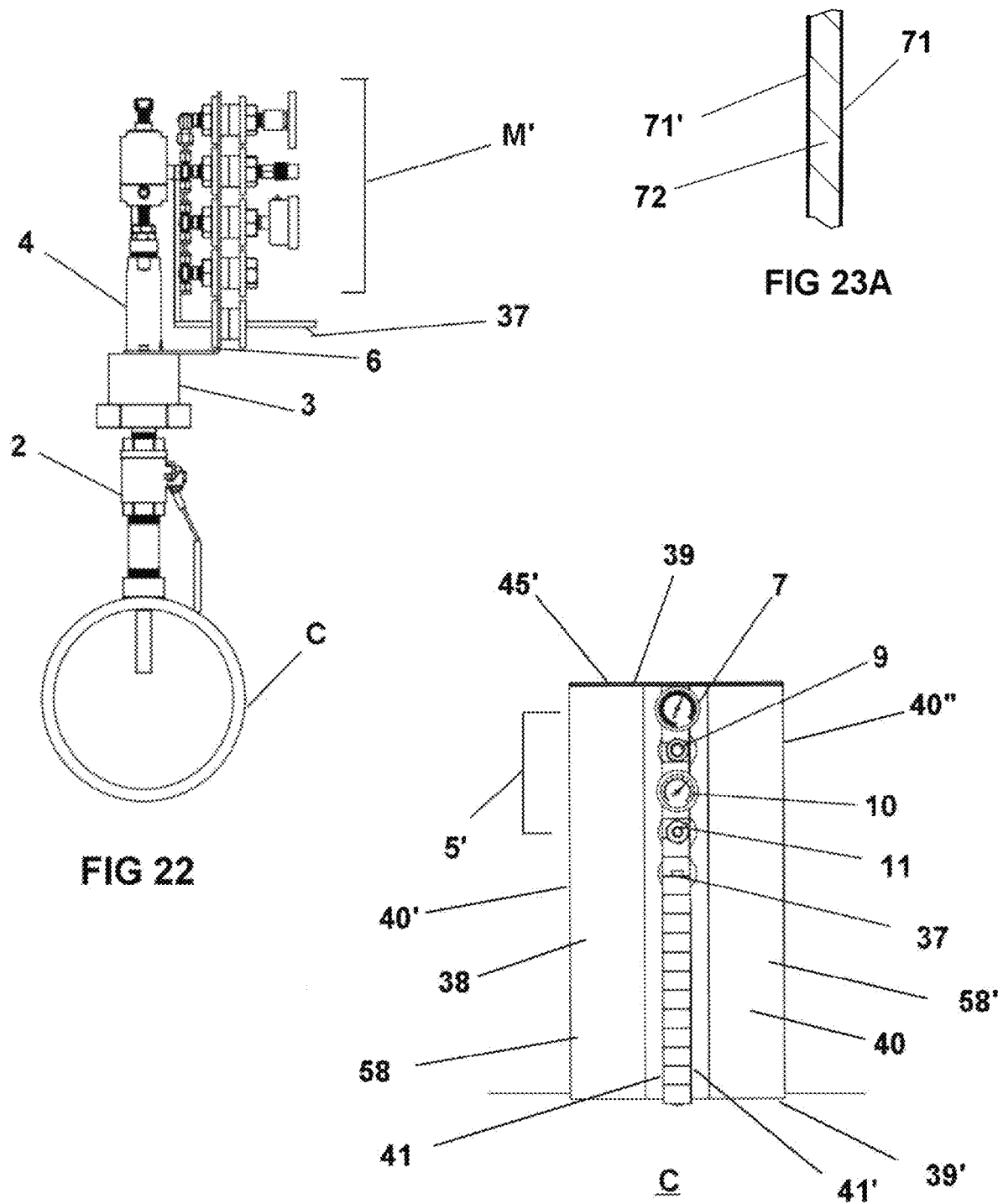

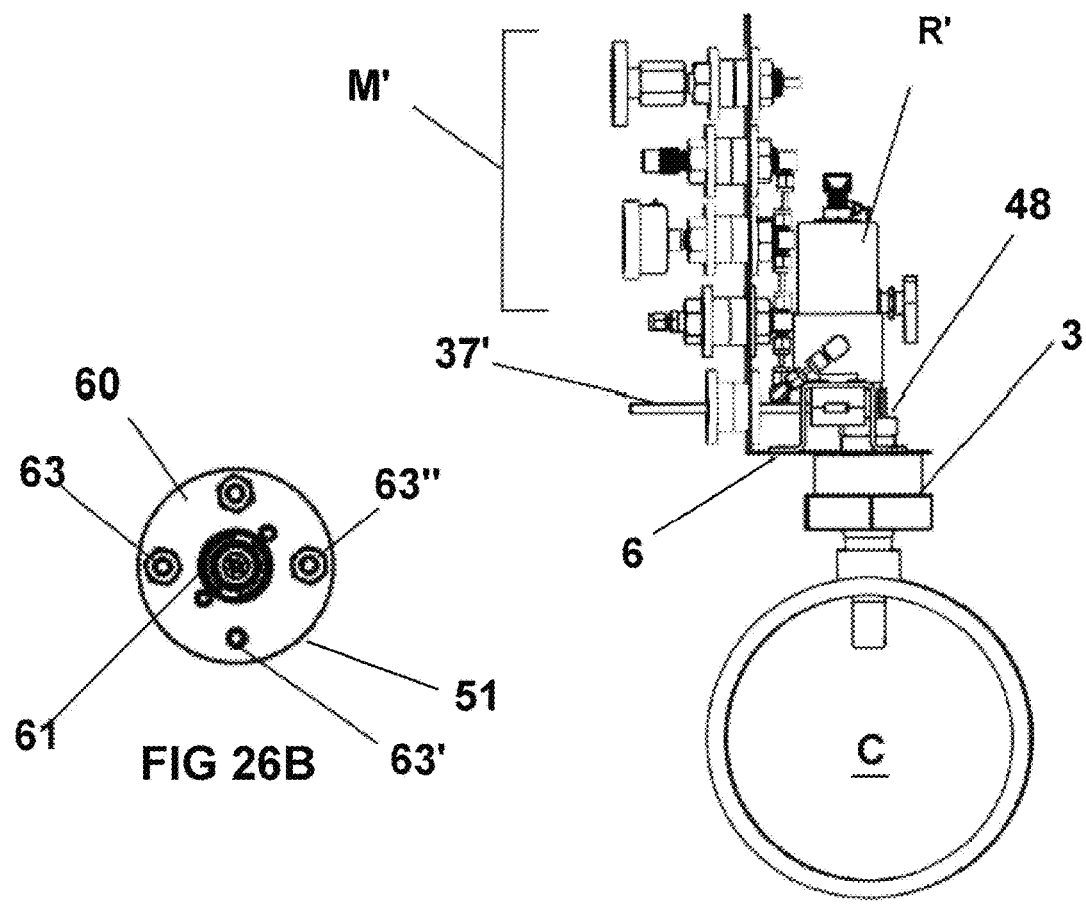
FIG 25
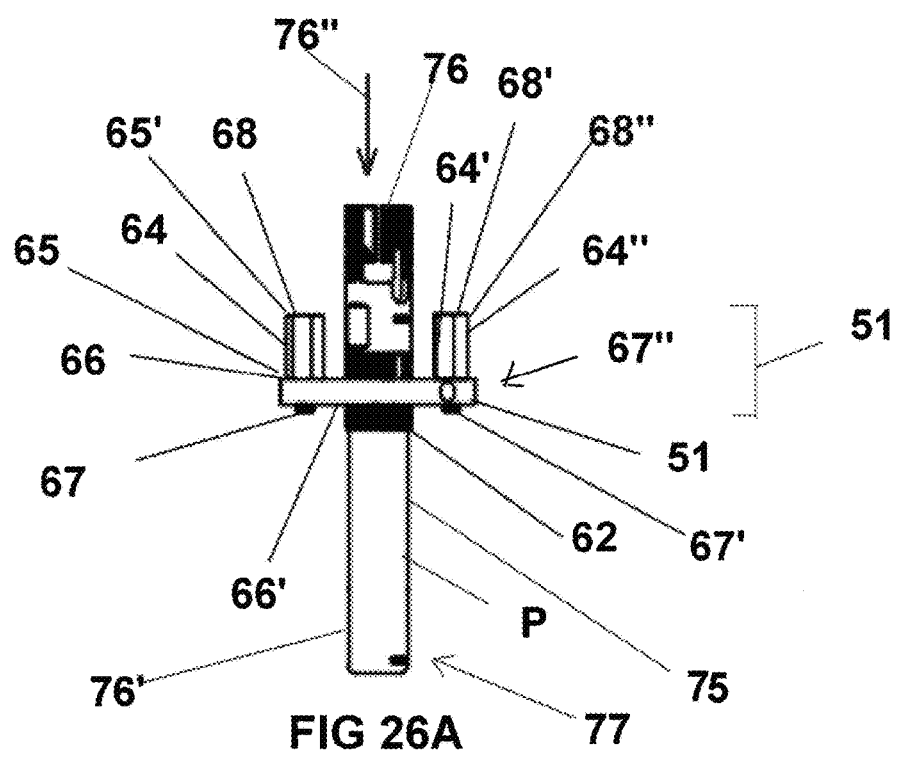
FIG 26B
FIG 26A

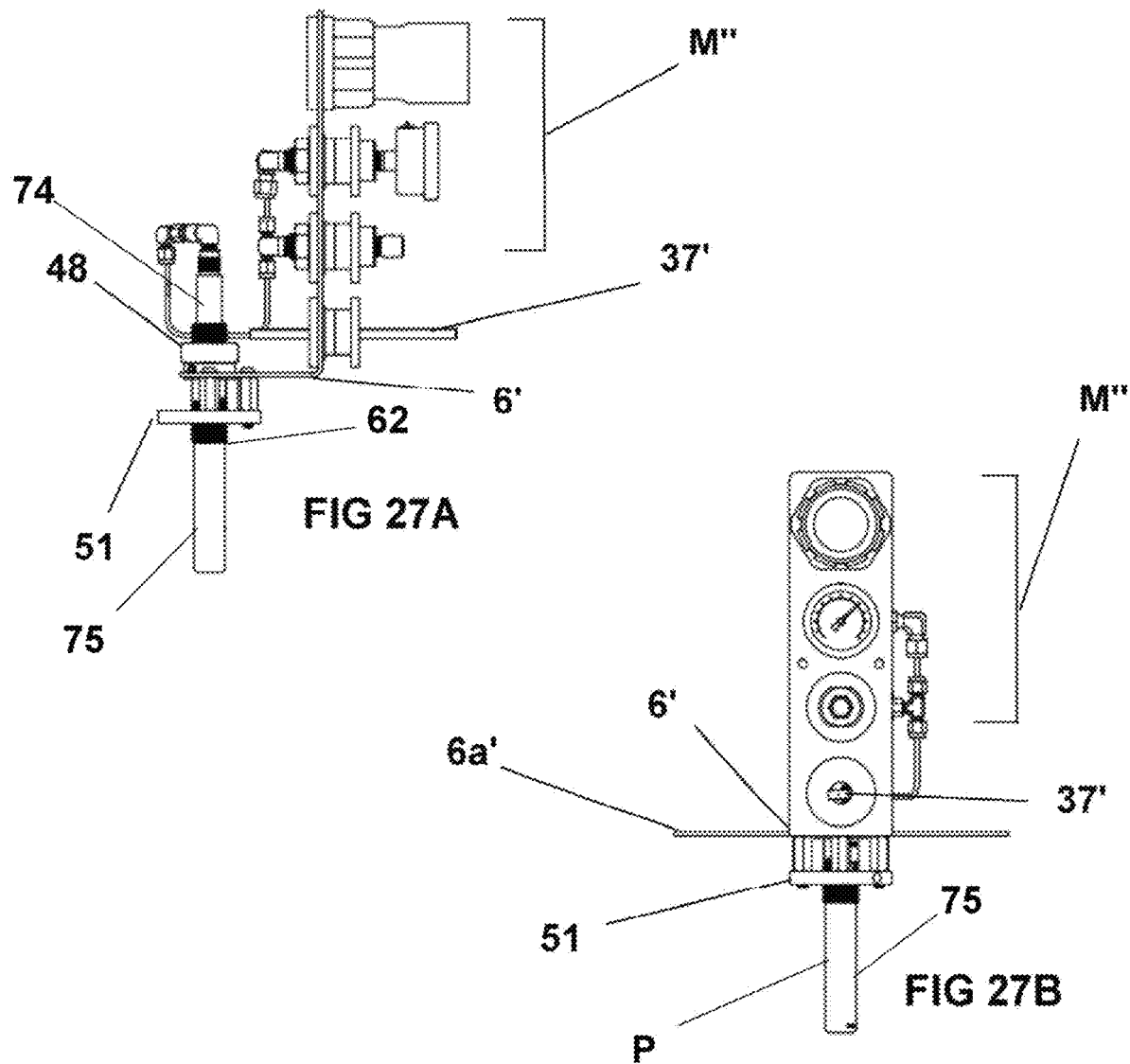

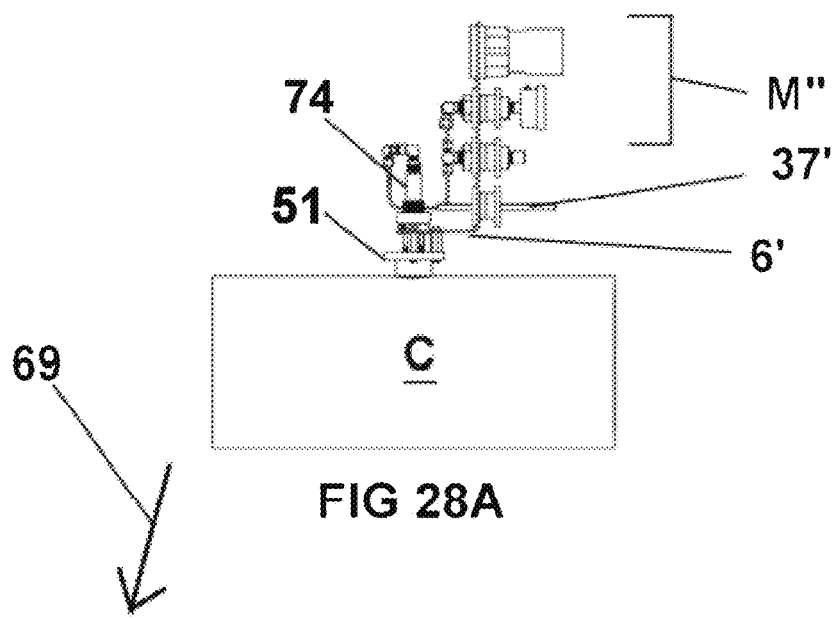
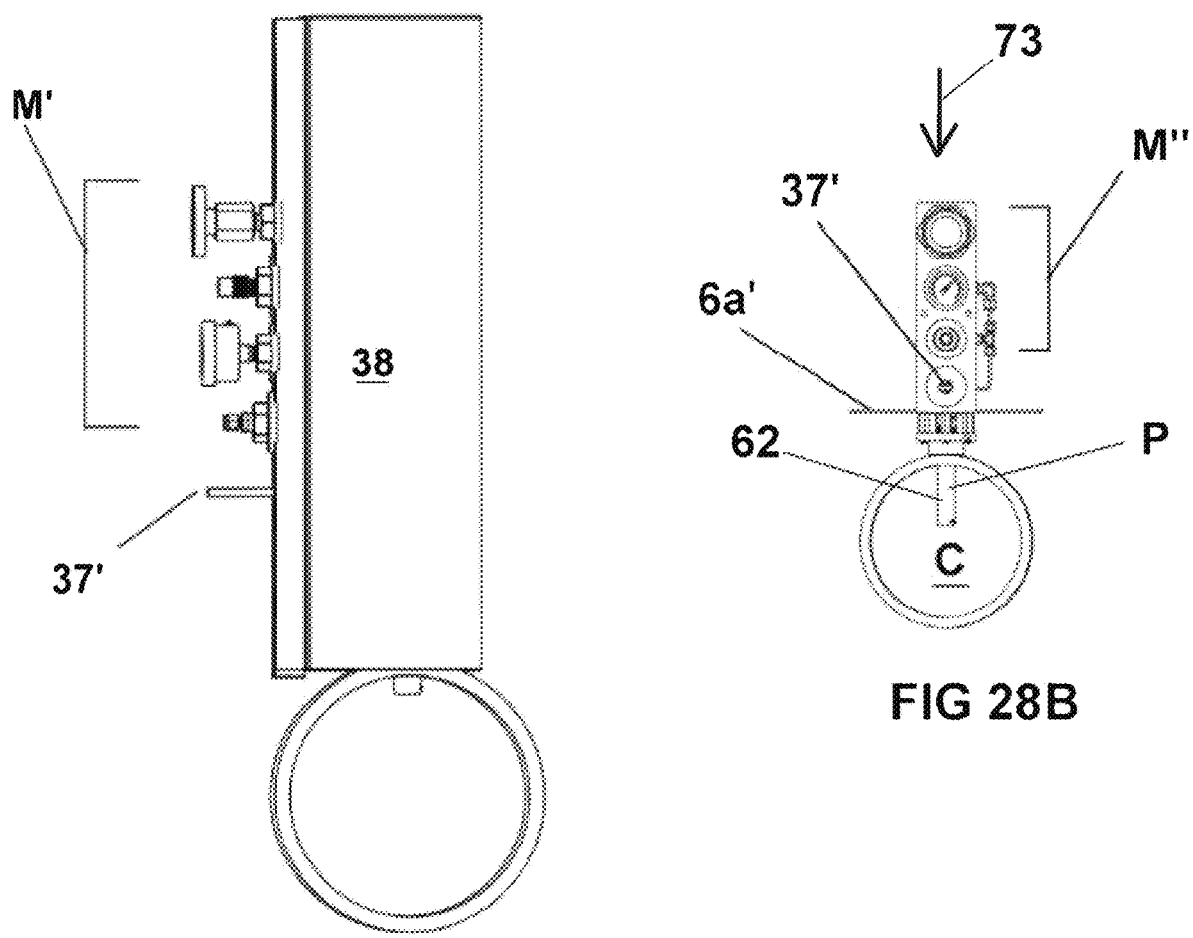

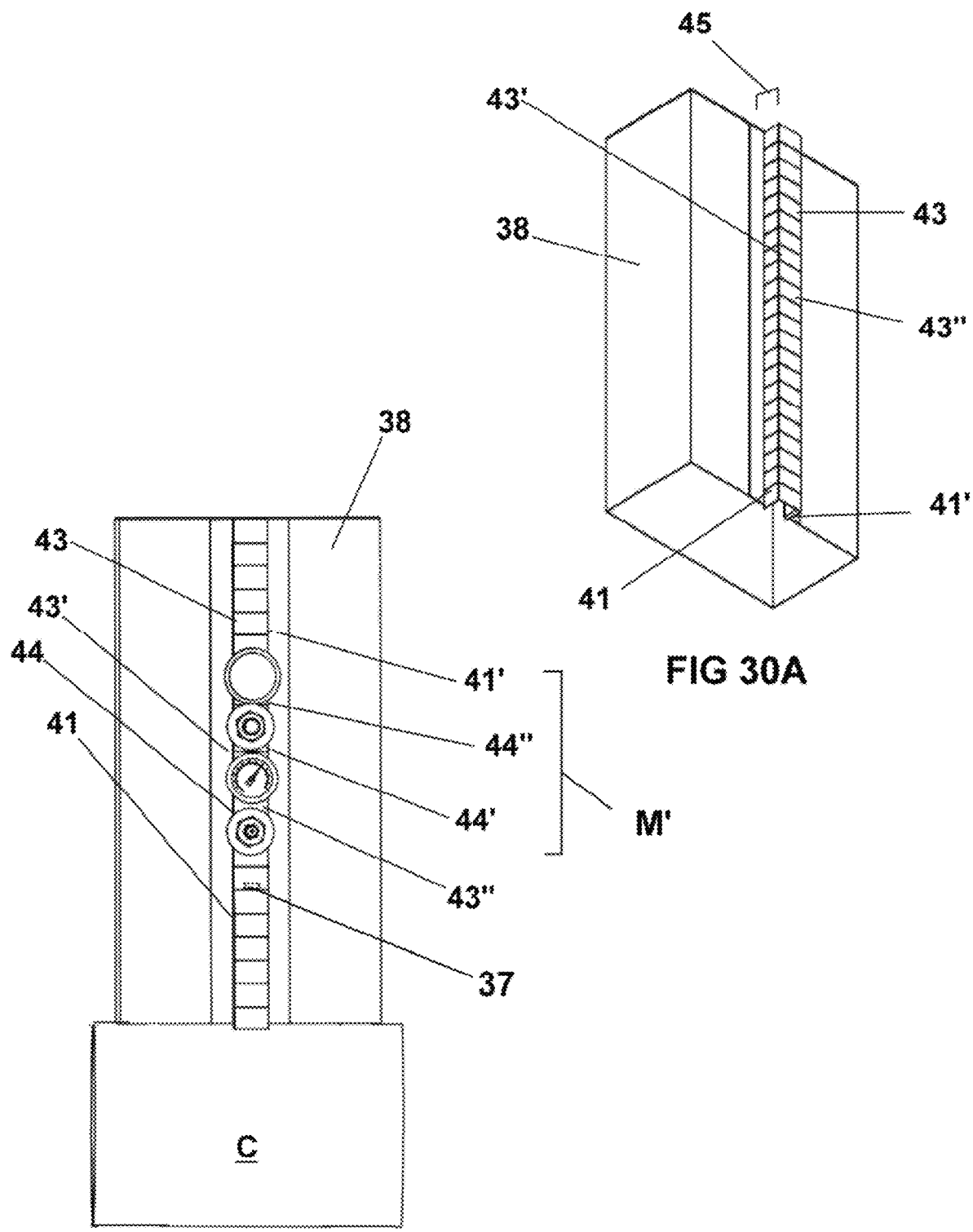

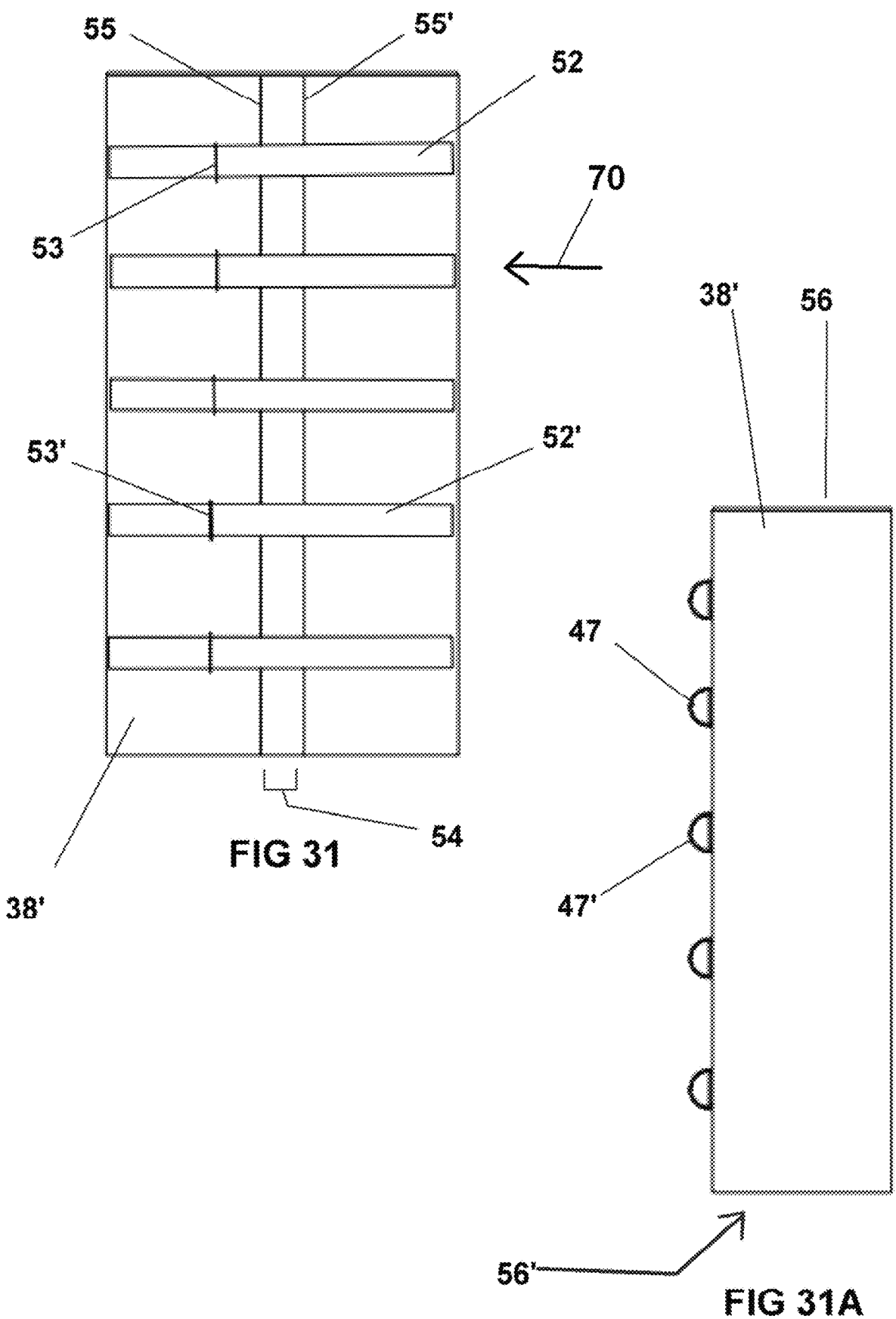

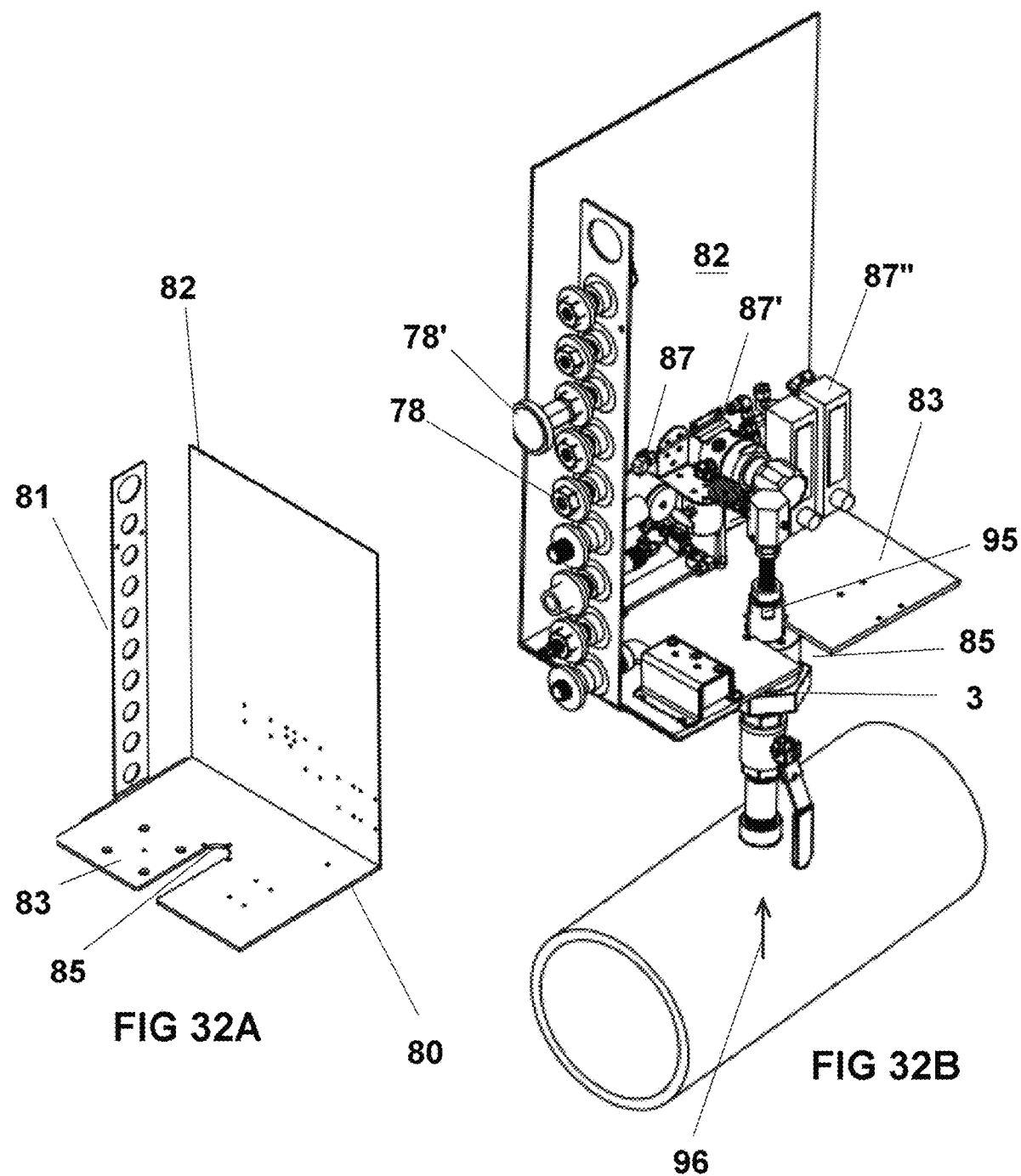

MODULAR SAMPLE SYSTEM INCORPORATING MOUNTING BRACKET INDEPENDENT OF HOUSING, AND METHOD THEREFORE

CROSS REFERENCE TO RELATED APPLICATIONS

The present application is a continuation in part of the U.S. Utility patent application Ser. No. 16/005,431 filed Jun. 11, 2018, entitled "Modular Sample System incorporating Bracket Independent of Housing and Method Therefore", listing Valmond Joseph St Amant III as inventor, which '431 application is a continuation in part of U.S. Utility patent application Ser. No. 15/228,814 filed Aug. 4, 2016, now U.S. Pat. No. 10,073,013 B2, entitled "Modular Sample System incorporating Bracket Independent of Housing and Method Therefore", listing Valmond Joseph St Amant III as inventor, which '814 application claims the benefit of U.S. provisional patent application Ser. 62/202,478 filed Aug. 7, 2015. Said '431 present application is also a Continuation in Part of U.S. Utility application Ser. No. 15/615,786 filed Jun. 6, 2017 entitled "Source Mounted Wet Gas Sampling System" listing Valmond Joseph St Amant III as inventor.

FIELD OF THE INVENTION

The present invention relates to sampling of pressurized process fluids for on-stream and spot sampling of pressurized process fluid such as natural gas or the like, said pressurized process gas having liquid entrained therein, or otherwise referenced as multiphase or "wet" in areas, including those with limited electrical power available. The present invention contemplates a source mounted sample system that is lower cost than the prior systems. One embodiment of the present invention provides a bifurcated housing which is supported by modular components protruding therethrough. Another embodiment eliminates the hard enclosure housing and replaces it with a flexible housing. The present invention also eliminates the need for a heater block, utilizing an existing heat trace instead. Finally, the present system further contemplates an improved, lower cost substrate coupling and allows for a less expensive fixed membrane probe or the like to be used instead of the more expensive insertable probes. The present system can utilize a docking platform or substrate configured to receive multiple, diverse sampling components customizable to various flow configurations coupled with engaging one or more of the mounted sampling components. The enclosure/housing of the preferred embodiment of the present invention particularly is suitable for use in Bureau of Land Management (BLM) regulated areas, utilizing a flexible, insulative material, providing advantages in mounting/removal in tight installations, cost, and flexibility of use, as well as providing superior access for enhanced visibility and/or manual access of same, providing an easily installed and maintained, user-accessible, on-site modular sampling conditioning/monitoring system. Finally, an alternative design of the present invention provides a split half enclosure for use in the bifurcated housing which is formed for use in areas where space is at a premium, such as between closely-spaced, thread-o-lets on a pipeline meter run or the like.

BACKGROUND OF THE INVENTION

Natural Gas is comprised of a mixture of gases (See API 14.1 Section 6.3 and naturalgas.org). Natural gas is bought and sold based on its heating value (BTU) which is derived from a compositional analysis of the natural gas. It is the BTU content that determines the monetary value of a given volume of natural gas. This BTU value is generally expressed in decatherms (one million BTU). In the determination of total heat value of a given volume of gas, a sample of the gas is analyzed and from the composition its heat value per unit volume is calculated. This value is generally expressed in BTU/cu ft. The typical range of transmission quality gas ranges between 1000 and 1100 BTU/cu ft. Production gas, storage facility gas, NGL, and new-found Shale Gas can have much higher heating values up to or even exceeding 1500 BTU/cu ft.

There has been a long-standing controversy between gas producers and gas transporters regarding entrained liquid typically present in most high BTU/cu ft. gas (rich or "wet" gas). Transporter tariffs require essentially liquid-free gas. Liquid in the gas being transported causes operational and safety problems. The practice is to separate the liquid before entering a transport (pipe) line.

The API 14.1 standards (Manual of Petroleum Measurement Standards, 2006) scope does not include supercritical fluid (dense phase) or "wet gas" "(a term referenced by the Natural Gas industry as a gas that is at or below its hydrocarbon dew point temperature and/or contains entrained liquid), nor does the GPA 2166 standard (Obtaining Natural Gas Samples for Analysis by Gas Chromatography, 2005). In summary, there is no known standard which defines how to obtain a "representative sample" of a natural gas supply having entrained hydrocarbon in any form.

Therefore, to fully comply with the current industry standards, membrane-tipped probes such as the A+ Corporation LLC of Gonzales, La., GENIE brand Probe (see assignee U.S. Pat. Nos. 6,357,304, 6,701,794, 6,904,816, 7,004,041, and 7,134,318) have been used for many years to shed entrained liquids inside pressurized pipelines. Other companies such as Valtronics, Inc/Mustang Sampling have bolted enclosures to the A+ Corporation LLC membrane-tipped probes themselves, and power the additional electrically powered heater blocks and cartridge type heated regulators for the enclosure from the electrical heat trace (See Hess U.S. Pat. No. 4,821,905, www.pentairthermal.com, and GB2199451A), and then place A+ Corporation LLC GENIE brand membrane separators (U.S. Pat. No. 7,555, 964) in a second enclosure mounted closer to the analyzer (See Mayeaux U.S. Pat. No. 6,357,304, Thompson U.S. Pat. No. 7,162,933, and Thompson US 2012/0325694 A1 as well as Thompson D674,052). Other companies, such as Welker Engineering of Sugar Land Tex., use non-membrane probes and bring the liquids outside the pipeline to reject them, hanging a hinged enclosure onto the probe (see Welker SCHS data sheet). Welker and other companies such as PGI install sample pumps and composite samplers and bolt enclosures to the pipeline (see Welker U.S. Pat. No. 5,531, 130 and Nimberger U.S. Pat. No. 5,109,709).

Each of these enclosure systems are engineered for one specific configuration, and once the probe housing or pump is installed, it cannot be removed without shutting down and depressurizing the process.

In Thompson U.S. Pat. No. 7,162,933, an enclosure is provided with a Mayeaux U.S. Pat. No. 6,357,304 type probe, provided by A+ Corporation LLC of Gonzales, La., and diagonal enclosure such as Hess U.S. Pat. No. 4,821,905 along with a heat trace splice kit such as Raychem S150-ML and Tyco Electronics Raychem GB 2199451A.

Welker has a similar, two half-horizontal enclosure in U.S. Pat. No. 5,531,130 as does Hess U.S. Pat. No. 5,581,033A.

The Welker SCHS brochure depicts a vertical version of the two-half enclosure with a hinged door. Nimberger U.S. Pat. No. 5,109,709 utilizes a hinged door as well. Thompson US2012/0325694 A1 attempts to increase access to the probe inside the enclosure from using one like Hess U.S. Pat. No. 5,581,033A by using a diagonal-half approach like Hess U.S. Pat. No. 4,821,905. While this change may increase accessibility by 20%-30%, it still leaves much to be desired for component access. Further, the pipeline must be shut down and depressurized to install and remove the probe with all prior art.

All the existing art relies on power being readily available for electrical heater devices and electrical heater blocks to provide heat for the sample systems.

Many of the sample points where the sample installations are present are in small diameter pipelines with limited electrical power available or only low wattage close proximity solar power available. Solar power has been traditionally used in natural gas sampling for decades. See U.S. Pat. No. 5,501,080A, McManus et al, with 1994 Priority date as well as vendors such as ABB, web site www.new.abb.com/solar which pre-dates Thompson U.S. Pat. Nos. 9,459,185 and 9,733,224. Also see Mayeaux U.S. Pat. No. 7,051,604 wherein the second embodiment teaches the use of vacuum jacketed means for a fluid sample system from a pipeline. Some of the sample points will only have solar power available for the short distance of self-limited heat trace tubing.

GENERAL SUMMARY DISCUSSION OF THE INVENTION

The present invention provides a unique system designed to solve the prior art problems relating to access, ease of use, and flexibility as it relates to source mounted sample systems.

More specifically, unlike prior art, the present invention is modular. It is uniquely designed with a common substrate to accommodate various diverse and different configurations. This modular approach allows common inventory that facilitates lean manufacturing techniques.

The system substrate has a common coupling that facilitates a common bracket which utilizes a common enclosure with a common array of pre-drilled holes. This modular platform substrate allows components or modules to be put in different flow path order, deleted or added, or changed without affecting the probe or the size of the enclosure and all using the same substrate coupling. The probe or pump is independent of the modular sample system.

Another benefit of the present invention is the fact that a spare module may be kept in stock and replaced in the field. So, should extensive maintenance be necessary, the entire sample system module could be replaced (without shutting down the process and without removing the probe) by a less skilled technician, and then the troubled system could be returned to a central facility where more experienced technicians can trouble shoot and repair it or just clean if it necessary.

Further, unlike prior art, the present invention facilitates 100% access to all components. It accomplishes this objective without the need for hinges or diagonal cuts. The system is designed so that the enclosure is independent of the probe or pump and the components. The enclosure can be easily and completely removed without disturbing the probe or any other components of the system. The modular system is independent of the probe and the enclosure.

Finally, although the present invention is modular and an assemblage of several components, namely the substrate coupling (forming a base), mounting bracket, modular sample components, and enclosure components, the present system is configured so that the assemblage is structurally integrated to increase rigidity in the overall structure, providing a stable docking platform able to receive a diverse selection of components such as electronic, electrical, flow control, sample conditioning, monitoring, etc, while allowing the components to be easily mounted in customized fashion with environmental protection, but exterior visibility and control access as desired.

Components typically used in analyzer sample conditioning that technicians need visibility may comprise the pressure gauge, temperature gauge, outlet fitting, relief valve, conduit wiring connection, and others. The technician needs to be able to read (visually access) the pressure and temperature gauges, and physically access the outlet fitting, and inspect the conduit wiring, as well as inspect the relief valve to verify that it is not activated. Other components such as tubing and fittings and valves only need to be infrequently accessed for service or maintenance, and therefore not be visible exterior the housing, while the previously listed components need to be visible by the technician. The present invention allows the visibility of those components without having to open or disassemble the enclosure (housing).

In addition, the housing/enclosure of the present system provides protection from the environment with the aforementioned exterior access/visibility of desired components, as well as all components AND tubing when the enclosure is removed. All the while, the support system (i.e., substrate coupling and bracket(s) and supports) maintains its system rigidity, and access to the interior of the housing requires no breaking of fittings or connection or disassembly of the system, and, once the housing is removed, all components therein are readily accessible.

The housing formed in the present invention can include environmental isolation features, wherein the housing is insulated so as to allow control of temperature therein and can be heated and even powered from an existing heat trace tubing bundle associated with an analyzer, which may be located exterior (upstream as well as downstream the analyzer) or interior the housing. The housing/enclosure of the present system may be utilized for various applications with the design particularly suitable for enclosing modular conditioning components, analyzers and the like flowing from a sample probe, which may be an insertion probe or fixed installation. The probes in the preferred embodiment of the present system may or may not, depending on the application, utilize a membrane or the like to reject entrained liquids, while the insulated enclosure/housing is designed to maintain the sample system temperature above the sample dew point to prevent further condensation.

Unlike the prior art, the present system, being completely modular, allows a technician to remove the entire sample system (modular components mounted to a support bracket) and replace it with a spare while using the same enclosure and substrate coupling. In such a retrofit, the substrate coupling need not be removed from the process isolation valve or other support. Further, the probe need not be removed from the process pipe, because the probe is also independent of the substrate coupling and the enclosure, as designed.

The preferred embodiment of the present invention (FIGS. 1-11B) teaches a system wherein the modular sample system is mounted at the source of the sample (in situ).

A second embodiment would be (FIGS. 12A-12B) contemplates the modular sample system situated downstream of the source, but before an analyzer.

A third embodiment discloses the modular sample system 5 at the analyzer A, or configured into the analyzer. (FIG. 13).

A fourth embodiment could include sample conditioning systems situated upstream the analyzer A' (FIGS. 14-15).

A fifth embodiment includes the analyzer and modular sample system mounted together at the source of the sample, which could include the analyzer and conditioning system sharing the same support bracket and housing.

A sixth embodiment comprises a flexible housing formed of insulating material, as opposed to the housing shown in other embodiments, which may be rigid or semi-rigid. The flexible insulated enclosure is easily removed providing 100% access to all components when the enclosure is removed, while maintaining the rigidity of the system, and without the necessity of having to break any fittings or connection, or interfere with the operation of any extraction device present, or otherwise require the disassembly of the flow system for general maintenance/inspection, and offers ease of installation over a rigid housing, allowing for installation/removal where space is tight and a rigid housing might prove difficult to use.

The sixth embodiment preferred embodiment of the flexible housing, being insulated, does not require the use of a heater block, and can use an existing heat trace instead. Further, the flexible enclosure of the sixth embodiment allows for the utilization of various probe configurations, including less expensive options when compared to past systems. It maintains the docking platform or substrate configured to receive multiple, diverse sampling components customizable to various flow configurations coupled with engaging one or more of the mounted sampling components, so as to provide access exterior to the enclosure/housing for enhanced visibility and/or manual access of same, providing an easily installed and maintained, user-accessible, on-site modular sampling conditioning/monitoring system.

A seventh variation contemplates a hard or soft housing/enclosure wherein one of the half-enclosure components is split to facilitate use in close-spaced sample points on pipeline meter runs (approximately six inches, center-to-center), with many different types of instrumentation or other components installed. In these cases, the modular sample system should take the least amount of space. Sometimes, these thread-o-lets are as close as 6 inches apart. The standard configuration of this modular sample system has the outlet fluid connections and the incoming electrical connections protruding from the long side of the vertical enclosure. In closely spaced applications, it would be preferable to have the outlet connections and incoming electrical connections on the short side of the vertical enclosure. To solve this problem, a unique three-piece design incorporates the aforementioned modular sample system in-situ. As with the two-piece design, this design also allows all pieces of the enclosure to be removed without removing the probe or any of the sample system components for 100% access to all modular sample system components for troubleshooting or quick replacement.

An eight embodiment of the present invention contemplates a substrate bracket having at two or more vertical supports forming at least first and second module mounting areas. Said module mounting areas may be each oriented to support conditioning modules or the like to provide access exterior at more than one side panel forming the housing, or provide a module mounting area for mounting components so as to be fully enclosed by the housing components, allowing greater flexibility in the mounting and positioning of the components which is customizable to the requirements needed at each point of use. This would allow flexibility in the placement, as well as number of components contained in the housing. Further, the housing can be provided with openings along more than one side panel or junction of enclosure components to allow the partial pass-through and/or visibility of components, instrumentation, boots, or the like for access and/or visibility.

In summary, the present invention contemplates a unique, customizable modular sample system formed to receive a diverse selection of components such as electronic, electrical, flow control, etc, each mounted to a non-customized substrate and enclosure (housing). The mount of the present system is configured for easy mounting of a diverse array of components into a customizable configuration, while providing effective protection from the environment with exterior visibility and control of certain components, with a variation of the present invention particularly suitable for use in an install to accommodate closely-spaced thread-o-lets.

Finally, the system as configured provides an enclosure which is easily disassembled, providing 100% access to all components when the enclosure is removed, while maintaining the rigidity of the system, and without the necessity of having to break any fittings or connections, or interfere with the operation of any extraction device present, or otherwise require the disassembly of the flow system for general maintenance/inspection.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 1A is a partially cut-away, isometric view of a pressurized source contained in a pipeline or conduit C, with an isolation valve mounted thereto.

FIG. 1B is a partially cut-away, side view of the invention of FIG. 1A.

FIG. 1C is a partially cut-away, end view of the invention of FIGS. 1A-1B.

FIG. 2A is an partially cut-away, isometric view of the device of FIGS. 1A-1C, showing isolation valve 2 with the substrate coupling 3 mounted thereto.

FIG. 2B is a partially cut-away, side view of the invention of FIG. 2A.

FIG. 2C is a partially cut-away, end view of the invention of FIG. 2B.

FIG. 4A is a perspective, upwardly oriented view of an exemplary modular sample conditioning system of the present invention, illustrating of various exemplary components (alternatively referenced as modular components or modular sample components) forming the modular sample conditioning system 5, the components mounted to a substrate bracket or, alternatively referenced, mounting bracket; some of the components in the illustrated embodiment are configured to receive sample fluid flow therethrough for treatment (such as pressure regulator or heater), or providing a visual readout on indication (such as a gauge), or control (such as a valve) or support (such as an electrical connection), or the like.

FIG. 8B is an end view of the housing/enclosure of FIG. 8A, illustrating the configuration of the unit including the holes or apertures formed therethrough for external access to modular components (along the side wall edge of housing enclosure 20) as well as a mounting aperture mounting the housing situated at the bottom or end of the unit (in the preferred embodiment of the present invention).

FIG. 10A is a partial, frontal, close-up view of the housing for the modular sample conditioning components of FIGS. 9A-9C, with user viewable and control components accessible via openings in said housing/enclosure, as well as pins 17 used for alignment of the enclosure components with gaskets 18 therebetween and held in place via clasps 15, as well as retaining of the enclosure component(s) when same is opened for access.

FIG. 10B is a perspective, close-up view of the invention of FIG. 10A, providing a perspective view of various mounted modular components from exterior the housing.

FIG. 10C is a perspective, close-up view of the edge of one of the enclosure components, illustrating pre-formed openings for portions of the modular mounted component(s) to pass therethrough.

FIG. 16 is an end, partially exploded view of the invention of FIGS. 3A-3C.

FIG. 17 is a perspective, partially exploded view of the invention of FIG. 16

FIG. 18 is an end, exploded view of the invention of FIGS. 7A-7C.

FIG. 19 is a side, partial, cut-away view of the system of FIGS. 3A-3C.

FIG. 20 is a side, perspective close-up, cut-away view, of the invention of FIG. 3A.

FIG. 21 is an isometric, cut-away, close-up, view of the substrate coupling mounted to the isolation valve.

FIG. 21A is a cross-sectional view of the device of FIG. 21.

FIG. 22 is a side view of an alternative embodiment of the invention, having the substrate coupling 3, substrate bracket 6, isolation valve 2 mounted to conduit C or pipe, and extraction device 4 (shown as insertion probe) provided as in earlier embodiments, but utilizing a heat trace 37 instead of a heater block and power cable (for example, as shown in FIG. 7A-C), the present embodiment providing heat to one or more mounted modular conditioning components M' or the like, and without the necessity of a power cable.

FIG. 23 is a frontal, partially cut-away view of the system of FIG. 22 utilizing a flexible insulation housing 38 with a releaseable fastener such as hook and loop (i.e., VELCRO brand) straps to retain the unit in place (as further disclosed herein) and to anchor same about protruding portions of modular conditioning components 5 situated therein while allowing heat trace 37 to pass therethrough.

FIG. 23A is a side, partial, close-up, cross-sectional view of the layers of material forming the flexible, insulated housing 38 of the exemplary embodiment of the present invention.

FIG. 25 is a side view of the invention of FIGS. 24A-24B, with substrate coupling 3 having mounted thereto substrate bracket 6 supporting modular conditioning components M' and heat trace 37', which heat trace is formed to enter an enclosure or housing containing the modular sample system so as to heat the modular sample system, including probe 48 said probe formed to provide sample flow from conduit C.

FIG. 26A is a side view of an alternative configuration substrate coupling 51, in the form of a circular flange, that is more economical to manufacture than substrate coupling 3 shown in FIG. 25, the substrate coupling 51 of the present embodiment shown with probe assembly A passing therethrough (prior referenced GP2 membrane probe housing shown as an example).

FIG. 26B is a top view of the invention of FIG. 26A.

FIG. 27A is a side view of the substrate coupling 51 of FIGS. 26A and 26B having mounted thereto substrate bracket 6' (with base plate 6a') supporting modular conditioning components M" and heat trace 37', which heat trace engages probe 48.

FIG. 27B is a frontal view of the invention of FIG. 27A.

FIG. 28A is a side view of the substrate coupling 51 with substrate bracket 6' (having base plate 6a') supporting modular components 5" and heat trace 37' engaging probe 74, mounted to conduit C or pipeline.

FIG. 28B is a frontal view of the invention of FIG. 28A.

FIG. 29 is a side view of the flexible insulated housing/enclosure 38 of the present invention mounted to the modular sample conditioning system of FIG. 25, with portions of the modular sample conditioning components M' and heat trace 37 passing and thereby exteriorly accessible.

FIG. 29A is a frontal view of the invention of FIG. 29, illustrating the insulated housing/enclosure 38 mounted to the modular sample conditioning system of FIG. 25 situated on pipeline or conduit C, and fastener strips 43, 43', 43" for retaining the opposing edges 41, 41' of the enclosure in place and covering the spaces 44, 44', 44" between the conditioning components passing therethrough.

FIG. 30A is a perspective view of the flexible insulated housing 38 of the present invention, showing the raised 45 edges 41, 41' upon which are provided a plurality of straps 43, 43', 43" which are releasably adhered such as via hook and loop fastener (although belts, cinches, buttons, snaps, clips, clamps, zippers, pins and other means of fastening/retaining may be similarly utilized), providing flexibility in accommodating modular conditioning components, heat trace, power cables, sample conduits and other components or the like which protrude or pass therethrough, while filling any open spaces thereabout.

FIG. 31 is a frontal view of an alternative flexible insulated housing/enclosure 38' utilizing belts 52, 52' with buckles 53, 53' or cinches to secure the housing, the belts, 52, 52' positioned to fit around the components 47, 47' which pass through space 54 between the edges 55, 55', the housing/enclosure 38' having a top 5, the belts tightening about the housing to draw the edges 55, 55' together to engage any protruding modular components therebetween, and being flexible, the edges can be made to deform so as to lessen or eliminate the space 54 therebetween.

FIG. 31A is a side view of the invention of FIG. 31, illustrating the protruding modular components therebetween 47, 47'.

FIG. 32A is a perspective, side view of an alternative substrate bracket 80 to the bracket of FIG. 5, wherein, in addition to the module mounting area 81 provided at the front end of the unit, there is further provided a side mounting panel 82 situated orthogonally to the module mounting area 81, the side mounting panel 82 for having mounted thereto and supporting analyzers (such as the optical analyzer as shown, as well as gas chromatographs, spectrometers, etc), as well as other modular components, calibration cylinders, transceivers, and other devices.

FIG. 32B is a perspective view of the substrate bracket 80 of FIG. 32 mounted to the substrate coupling 3 of the present invention mounted to a conduit C or pipeline, illustrating a probe emanating from the coupling flowing a fluid sample to a regulator and various modular components mounted to the side mounting panel 82 and module mounting area 81 of substrate bracket 80.

FIG. 33 is an isometric view of an alternative embodiment to the inventions of FIGS. 11A and 32D, the present invention contemplating a modular sample system for closely spaced thread-o-lets mounted to the pressurized source contained in a pipeline or conduit with an isolation valve mounted thereto. The present invention includes a first and second housing components, the second housing component being bifurcated or split, comprising two sub-components which are easily joined to form the second housing component, or removed for access. Also provided in this embodiment is the option of providing more than one module mounting area emanating from the base of the substrate bracket. The present system is illustrated as mounted between two insertion probes situated in the adjacent thread-o-lets. Those adjacent thread-o-lets may accommodate simply the insertion valves so as to provide access to the fluid stream when required, the insertion probes as shown, other devices insert or otherwise fluidly connected, or be simply plugged via plugs or the like.

DETAILED DISCUSSION OF THE INVENTION

Figure 3A:
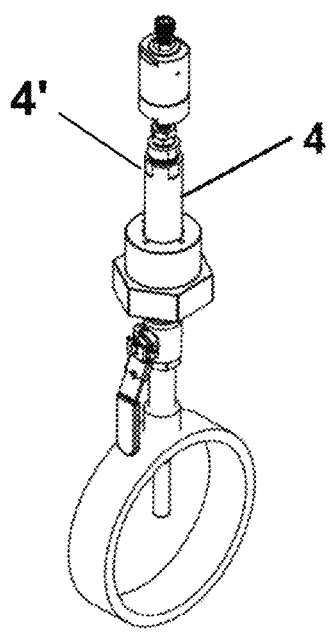
FIG. 3A is a partially cut-away, isometric views of the device of FIGS. 2A-2C, illustrating an exemplary extraction device 4 in the form of an insertion probe mounted to the substrate coupling.
Figure 3B:
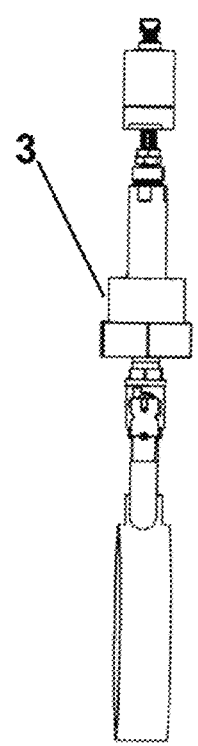
FIG. 3B is a partially cut-away, side view of the invention of FIG. 3A.
Figure 3C:
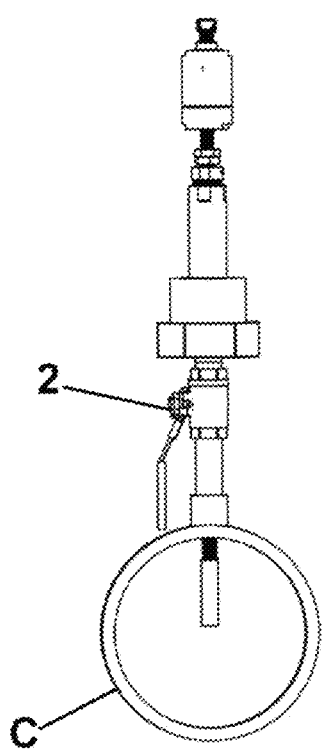
FIG. 3C is a partially cut-away, end view of the invention of FIG. 3B.

Referring to FIGS. 1A-11B and 18-21A, the first embodiment of the present invention contemplates unique and innovative housing configuration, with substrate coupling and separate bracket for use therewith, shown implemented in conjunction with a self-contained, modular sample/conditioning system mounted at the source of the sample, such as, for example, a pressurized source 1 comprising a pipe or conduit C having mounted thereto a process isolation valve 2 (FIGS. 1A-1C).

A substrate coupling 3 (FIGS. 2A-2C) is mounted to the process isolation valve 2. The coupling 3 connects the process source 1 to the modular sample system of the present invention (discussed in detail infra) while also allowing for the installation/utilization of an independent, insertable extraction device such as Mayeaux U.S. Pat. No. 8,522,630 probe, the contents of which are incorporated herein by reference thereto.

As shown in the figures, the substrate coupling 3 comprises a body B having first 31 and second 31' ends providing first and second mounting surfaces, respectively, and a length 31", with an axial bore or passage 33 formed longitudinally therethrough, said passage 33 having an internal diameter (ID) 33' sized for the positioning, i.e. insertion and retrieval, of the extraction device 4 (shown in the form of an insertion probe) therethrough. As shown, the tooling flat 3" of the substrate coupling 3 provides a surface for engaging via wrench or the like while inserting/retrieving the insertion probe (extraction device 4), which itself includes tooling flat 4' for tool engagement via insertion/retrieval. The second end 31' of substrate coupling 3 has a cylindrical socket 32 formed medially therein having an inner diameter (ID) 32' formed to receive insertion assembly 34 of extraction device 4, the passage 33 having a threaded connection 32" at the base 32b where it opens into socket 32. The second 31' end of substrate coupling 3 has formed about the opening of socket 32 a substrate coupling bracket mounting area 27, comprising threaded apertures 3a, 3b, or slots formed to secure the base 6a of substrate bracket thereto. The cylindrical sidewall 27' of substrate coupling forms the housing engagement area 28, having an outer diameter 28' (OD) formed to facilitate close association, abutting contact, or other engagement with the inner diameter/perimeter of the mounting aperture formed in the housing/enclosure, as further described herein. Situated below the housing engagement area 28 is substrate coupling base 3' (shown having a hexagonal face providing the aforementioned tooling flat 3" forming engaging notches for engagement via a wrench or the like for mounting), the base 3' having a width 28" greater than the diameter 28' of housing engagement area, said base orthogonally emanating from said sidewall of said substrate coupling so as to provide an extension 29 or support area, which could be used to support a housing resting thereupon, as will be further discussed herein. As shown, the first 31 end of body B has a nip 33' emanating therefrom, thereby providing an extension of passage 33, which, when combined with socket 32 provides a coaxially aligned feedbore along a common axis through the length of the substrate adapter (also referenced as an insertion probe adapter), for receiving the insertion probe therethrough.

In the present system, the modular sample/conditioning system cooperatively engages the isolation valve so as to allow for the passthrough of an extraction device 4 (FIGS. 3A-3C), and allows both components to operate independently of one another. An enclosure (14a and 14B in FIGS. 9A-11B) is provided to house the modular components (as further discussed herein), but does not require direct connection or engagement to extraction device 4, as is the case with prior art.

FIGS. 3A-3C and FIGS. 16-21A illustrate the extraction device 4 passthrough ability through the substrate coupling 3 and threaded connection thereto, through open isolation valve 2, to conduit C.

Figure 4A:
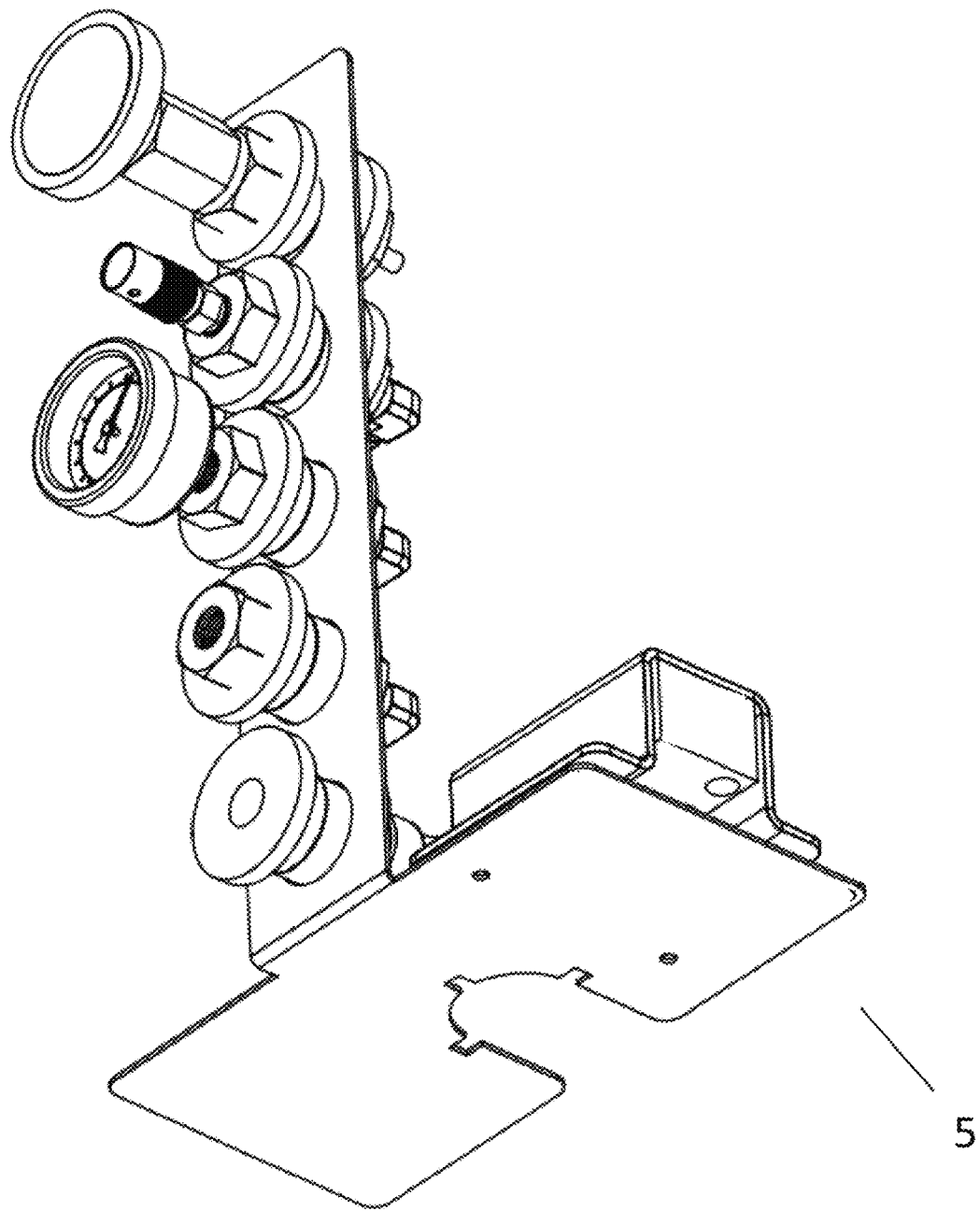
Figure 4B:
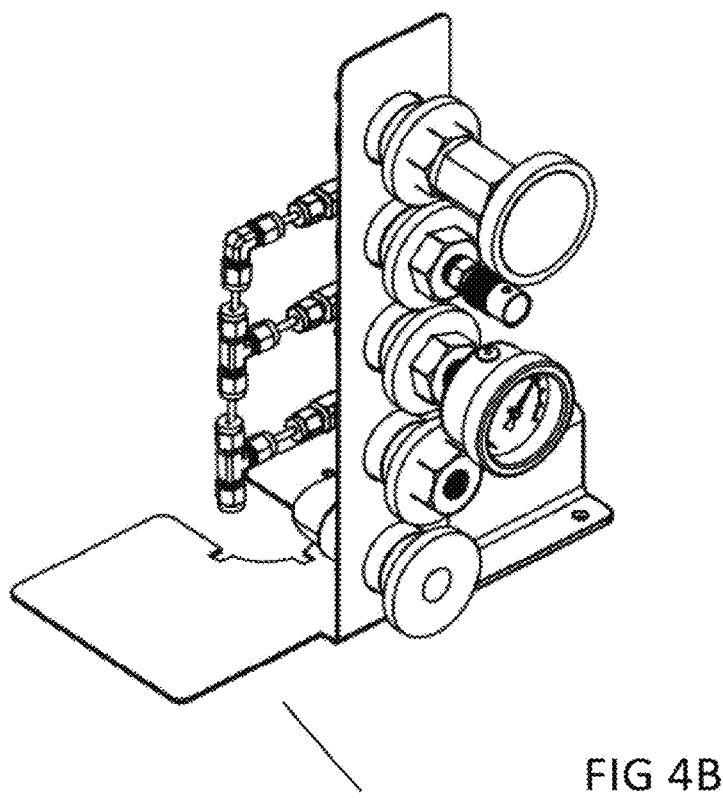
FIG. 4B is a perspective, downwardly-oriented view of the invention of FIG. 4A.

FIGS. 4A-4B illustrate an exemplary application of the modular sample system 5, comprising multiple diverse sampling and/or conditioning components mounted to a mounting bracket, also referenced as the substrate bracket. The modular sample system 5 can be pre-configured independent of the operation of the extraction device 4, and also independent of the enclosure 14a and 14B, on-site, as required.

Figure 5:
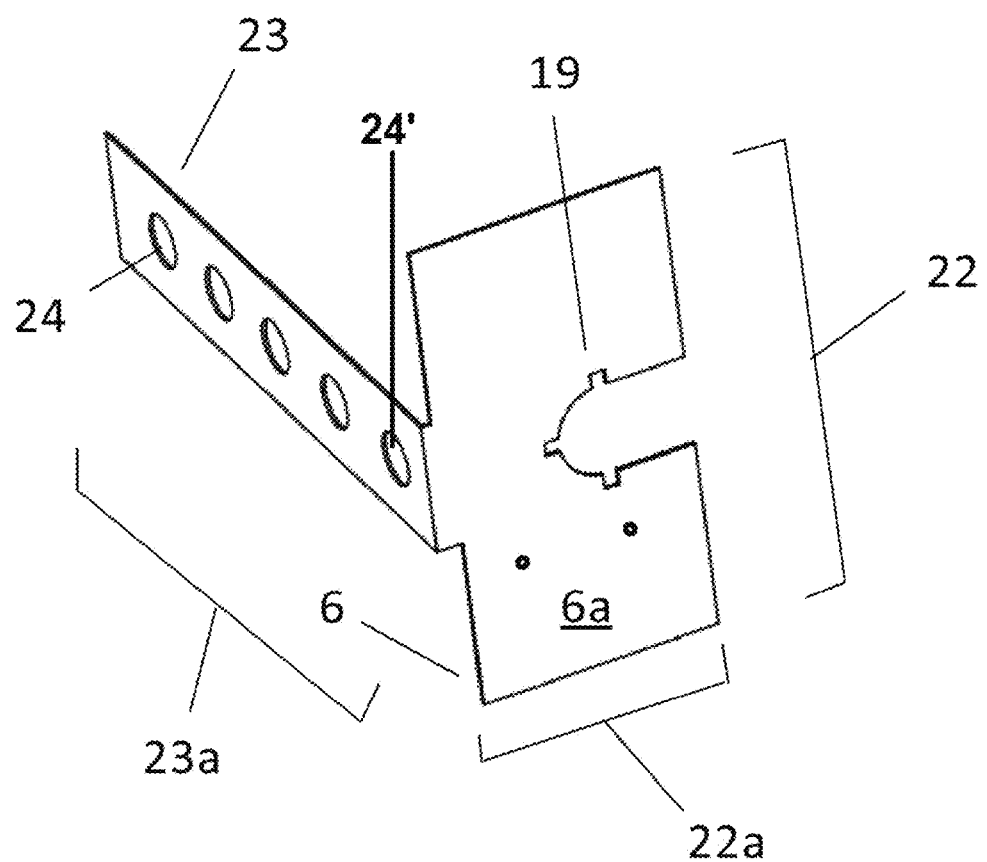
FIG. 5 is an upper, isometric view of the substrate bracket 6 (a/k/a mounting bracket) of the present system.

FIG. 5 illustrates the substrate bracket 6 before the individual modular sample system components are attached and configured on it. The bracket is configured to allow multiple, diverse components to be installed thereto for cooperative flow therebetween, or otherwise, as required. The bracket holes of the substrate bracket 6 are shown as spaced evenly so that sample system components can be placed and configured in any desired order.

Figure 6A:
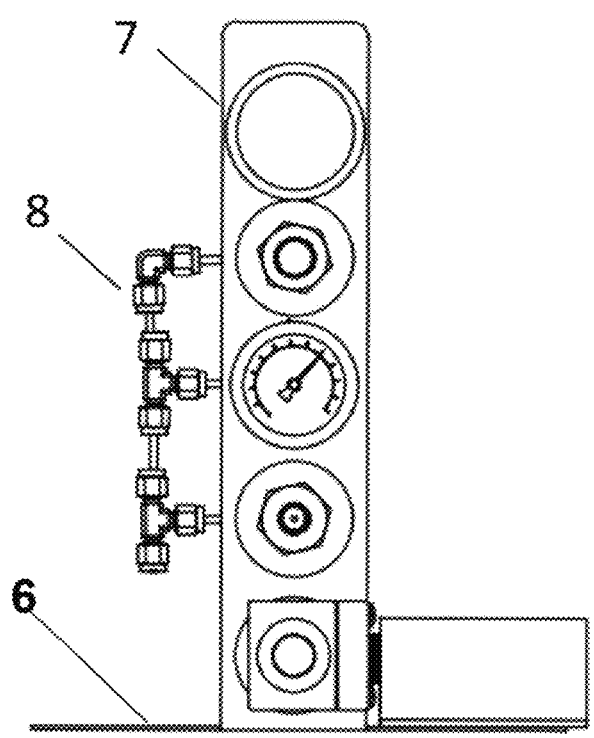
FIG. 6A is a front view of the first, preferred embodiment of the present invention, illustrating various exemplary modular sample components forming an exemplary modular sample conditioning system using the substrate bracket 6 or mounting bracket of FIG. 5.
Figure 6B:
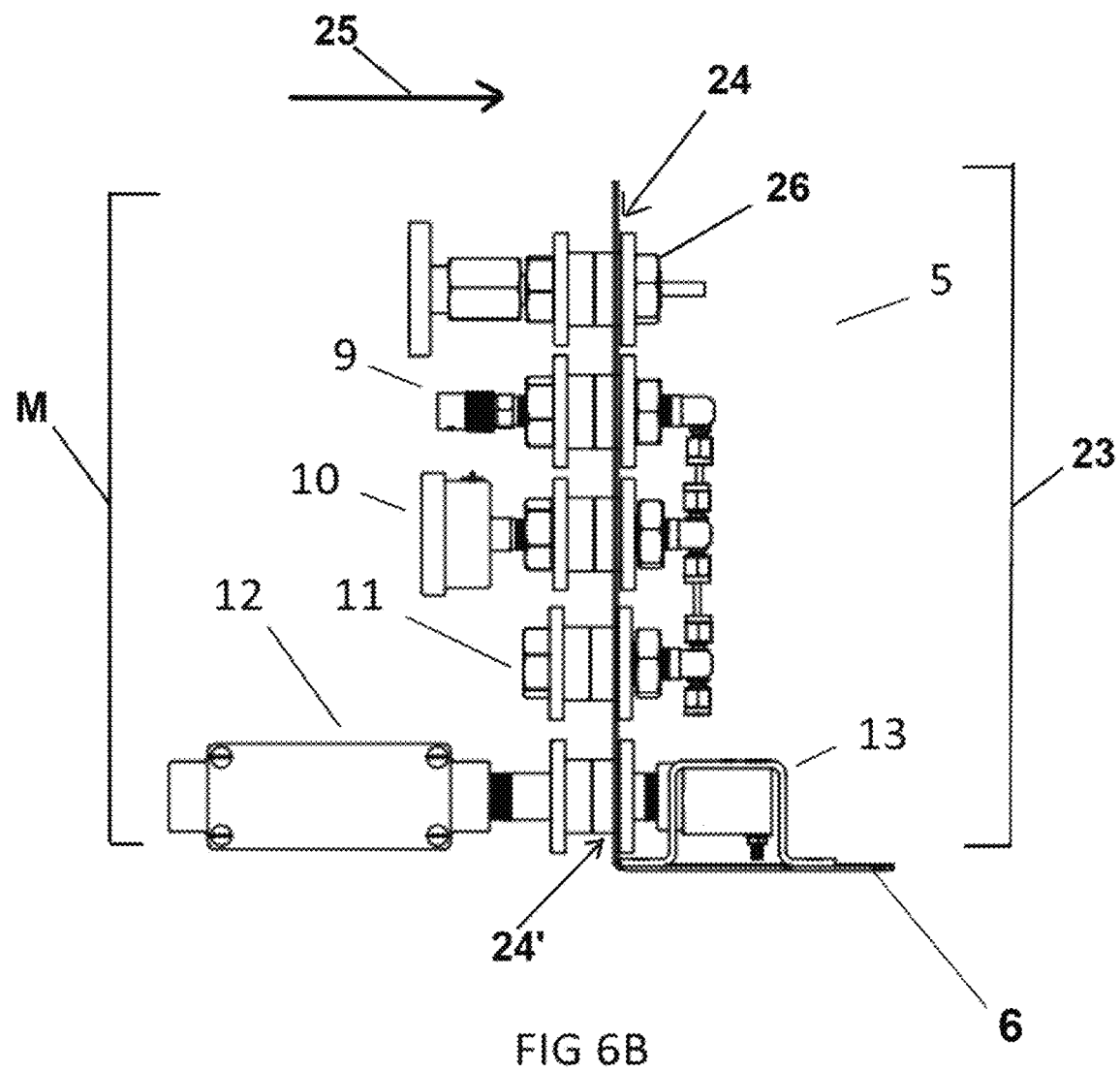
FIG. 6B is a side view of the invention of FIG. 6A.

The substrate bracket 6 is formed to readily attach, for example, via threaded mounting apertures 3a, 3b, at the free end of the substrate coupling 3 (FIG. 2C), which forms the substrate bracket mounting area 27 (FIGS. 2A-2C, 21, 21A) of substrate coupling 3. A typical modular sample system 5 configuration is shown in FIGS. 6A-6B. This exemplary system is shown incorporating various modular components M, including a temperature indicator 7, with tubing and fittings 8 connecting the various other components in the desired configuration, in the present example a serial flow comprising relief valve 9, a pressure gauge 10, an outlet NPT connection 11, a conduit junction box 12, and a self-limiting heater block 13, as shown. For purposes of discussion, those modular components M mounted to the substrate bracket mounting area 27 will be referred to as "mounted modular components"

Figure 7C:
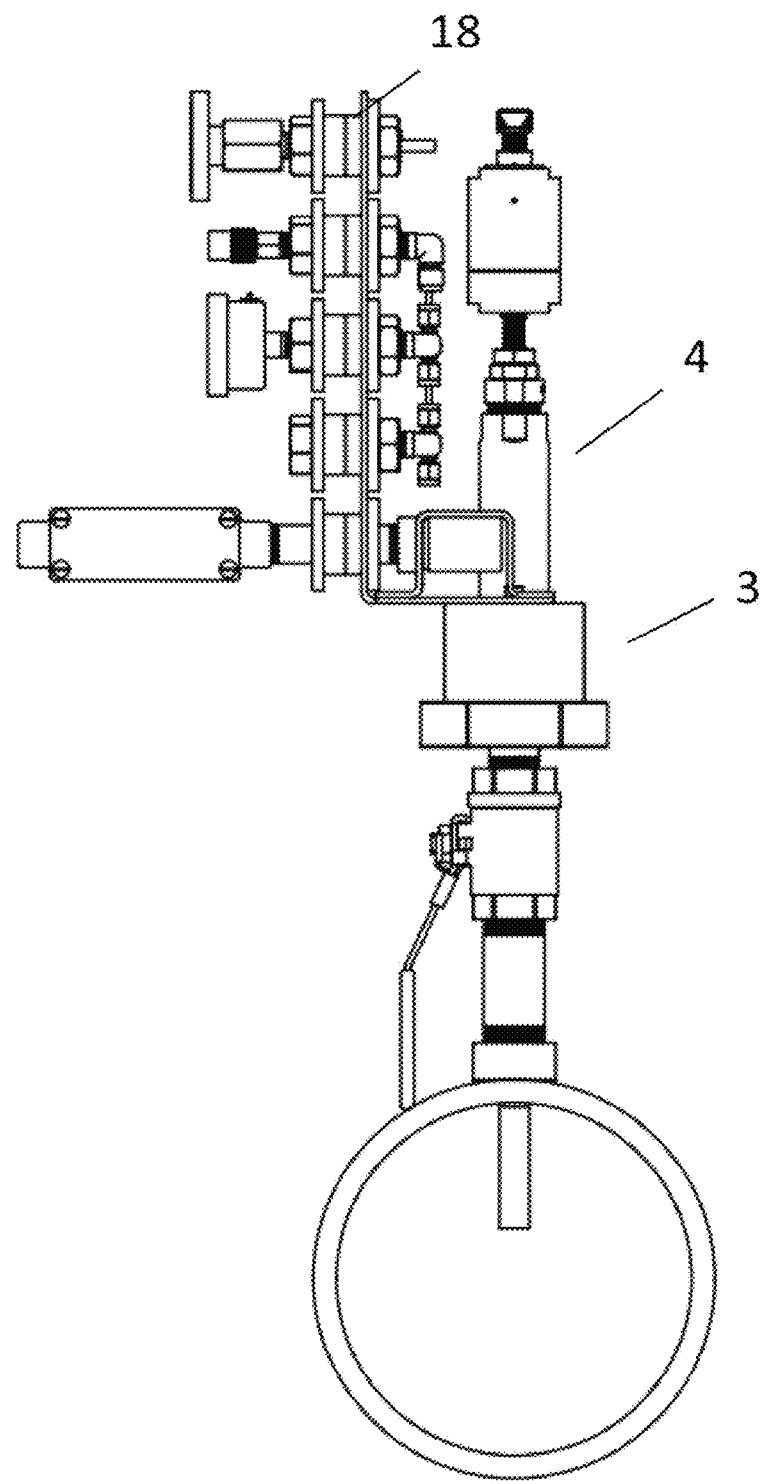
FIG. 7C is an end view of the invention of FIG. 7A.
Figure 8A:
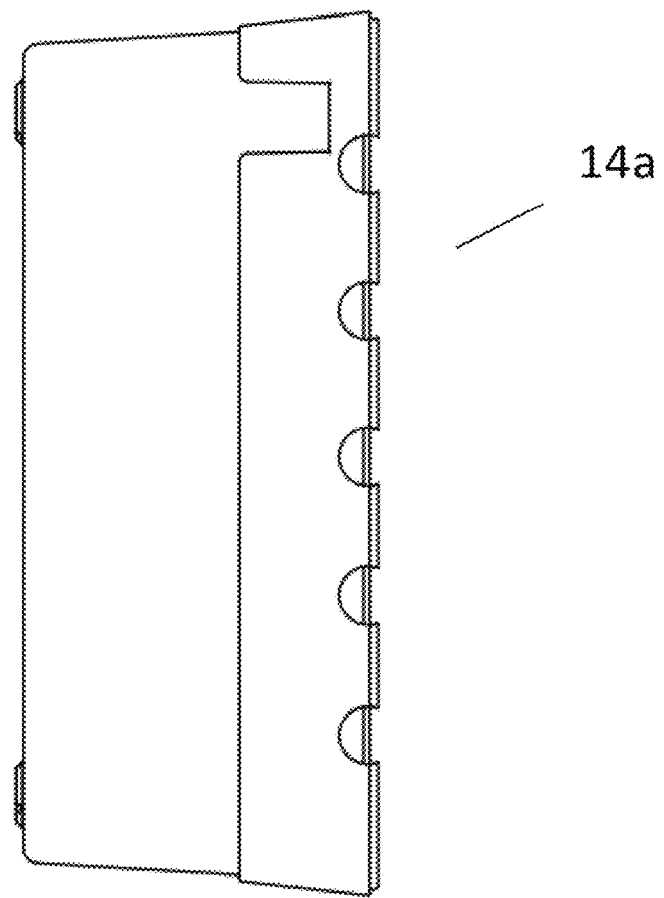
FIG. 8A is a side view of one of the two enclosure components of the components which are combined to form the housing of the present invention, the illustrated enclosure shown comprising the housing (approximately split in half along its length) with pre-drilled holes formed therethrough for component access and mounting of the unit.
Figure 11A:
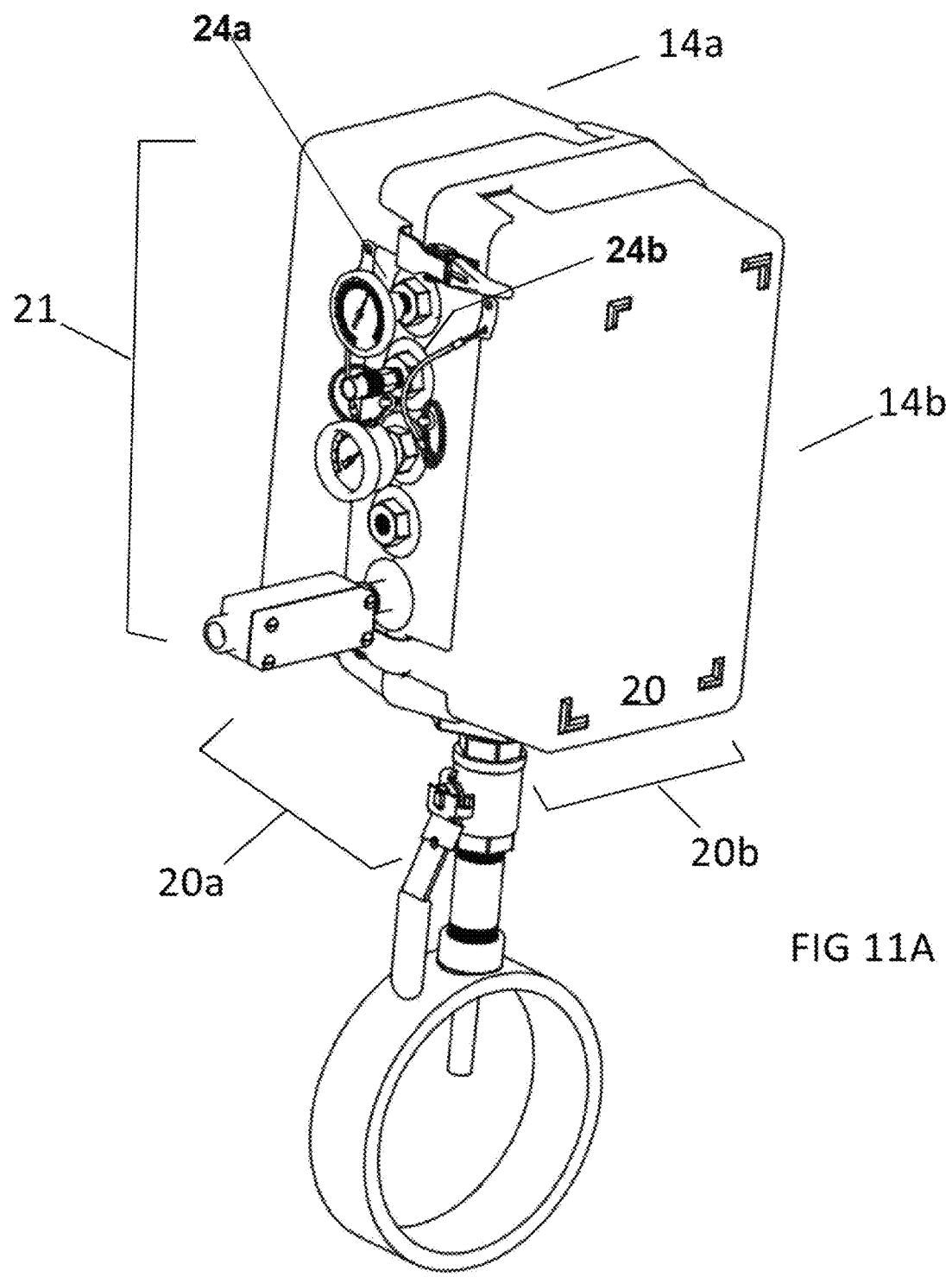
FIG. 11A is a perspective view, of the housing enclosure of the present invention enclosing the modular sample system of FIGS. 10A-10C, in a completed installation.

Each of these components are attached to the substrate bracket 6 (FIG. 5) and operate independent of the extraction device 4 (FIG. 7C) and the enclosure 14a and 14b (FIGS. 8A, 8B, and 11A).

Continuing with FIGS. 1-11B, the module mounting area 23 of substrate bracket 6 with sample components mounted thereto is orthogonally oriented relative to base 6A so as to be enveloped by while interfacing, supporting, and/or engaging 160 the housing formed by enclosure 14a, 14b components, to provide a modular sample system which is 100% accessible for service or replacement, with the exteriorly accessible components (visible portions of the components as well as those parts of the components for manual control) configured to pass through the housing or otherwise be selectively exposed or accessible by one or more opening(s) or apertures formed to receive same, as will be further discussed herein.

Figure 7A:
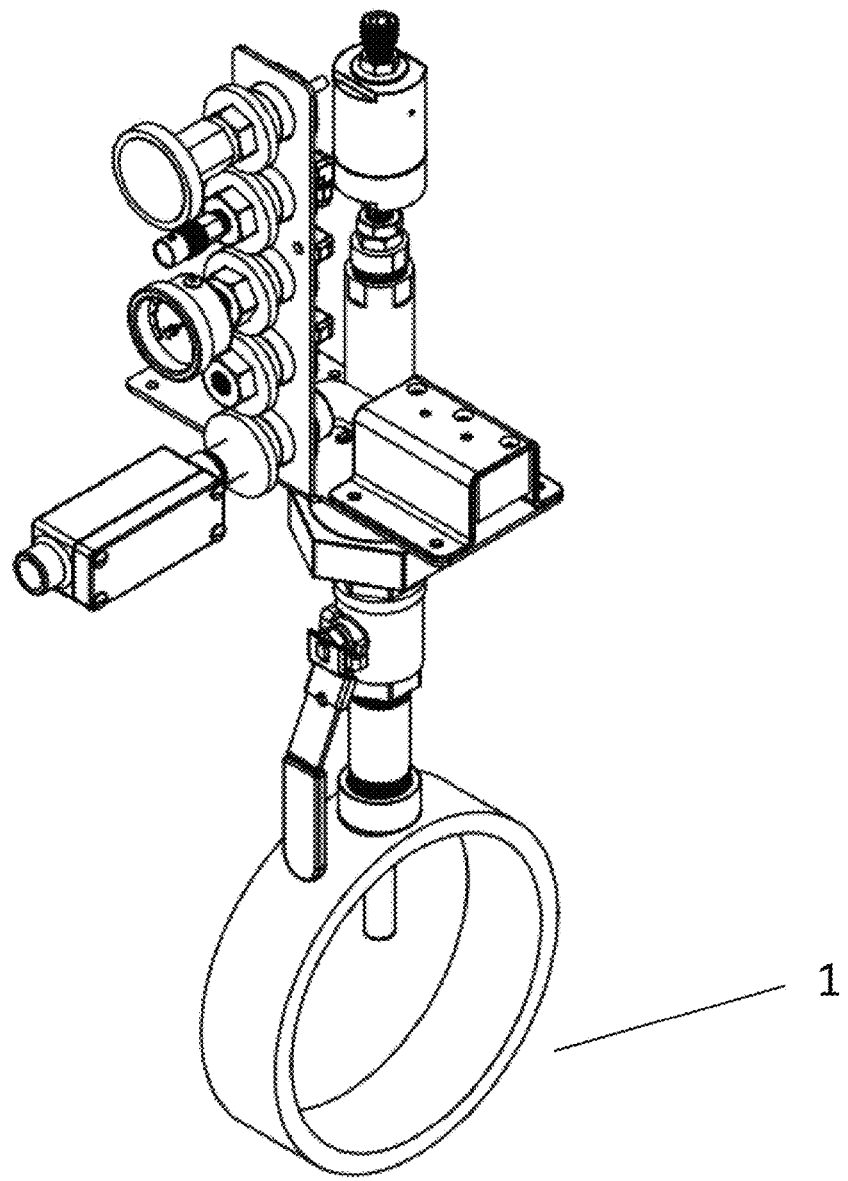
FIG. 7A is an isometric view of the exemplary modular sample conditioning system of FIGS. 6A-6B, with the substrate bracket 6 or mounting bracket mounted to the substrate coupling 3 of FIGS. 2A-2C with the extraction device as shown in FIGS. 3A-3C.
Figure 7B:
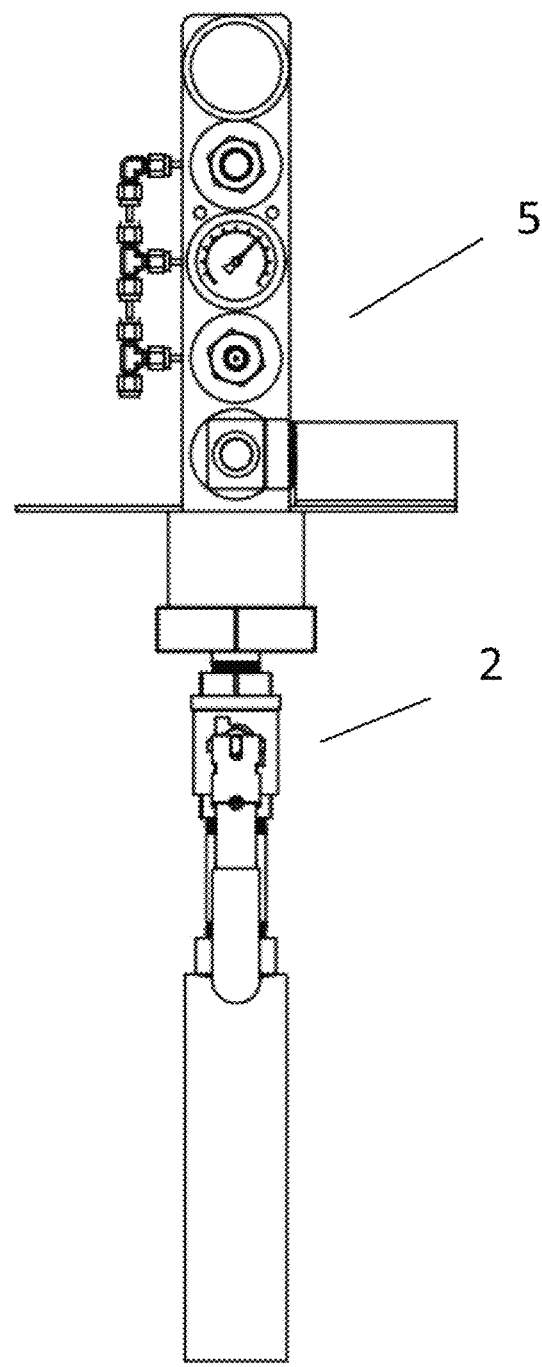
FIG. 7B is a side view of the invention of FIG. 7A.

FIGS. 7A-7C shows the pressurized source 1 with the process isolation valve 2 and the substrate coupling 3 and the extraction device 4 and the modular sample system 5. Also shown are the rubber gaskets 18 situated on the components to engage each hole of the bracket. The rubber gaskets 18 ("rubber" is an exemplary material, others may likewise be used), are positioned to engage the edges of one or both enclosures 14A, 14B when brought together at the housing component apertures, and are formed to seal the enclosure 14A, 14B about the components upon which the subject gaskets 18 are mounted, allowing a portion to pass through or otherwise be visible/accessible outside of the housing, as well as to help the enclosure slide onto and off of the substrate bracket.

Figure 9A:
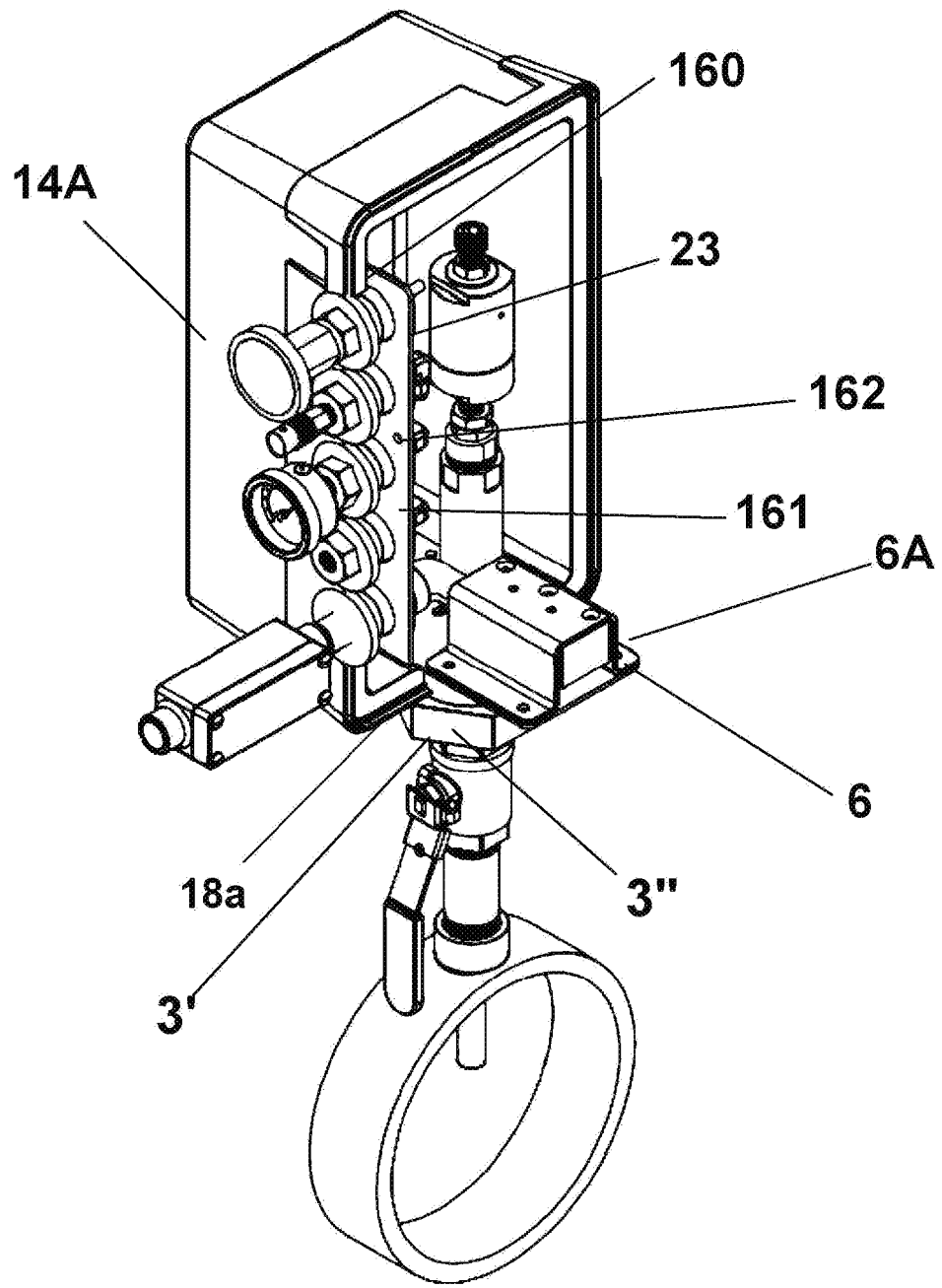
FIG. 9A is an isometric view, of the mounted sample conditioning system of the present invention comprising modular sample conditioning components substrate bracket 6 or mounting bracket of FIGS. 7A-7C, with the bracket housing/enclosure of FIGS. 8A-8B mounted thereto.
Figure 9B:
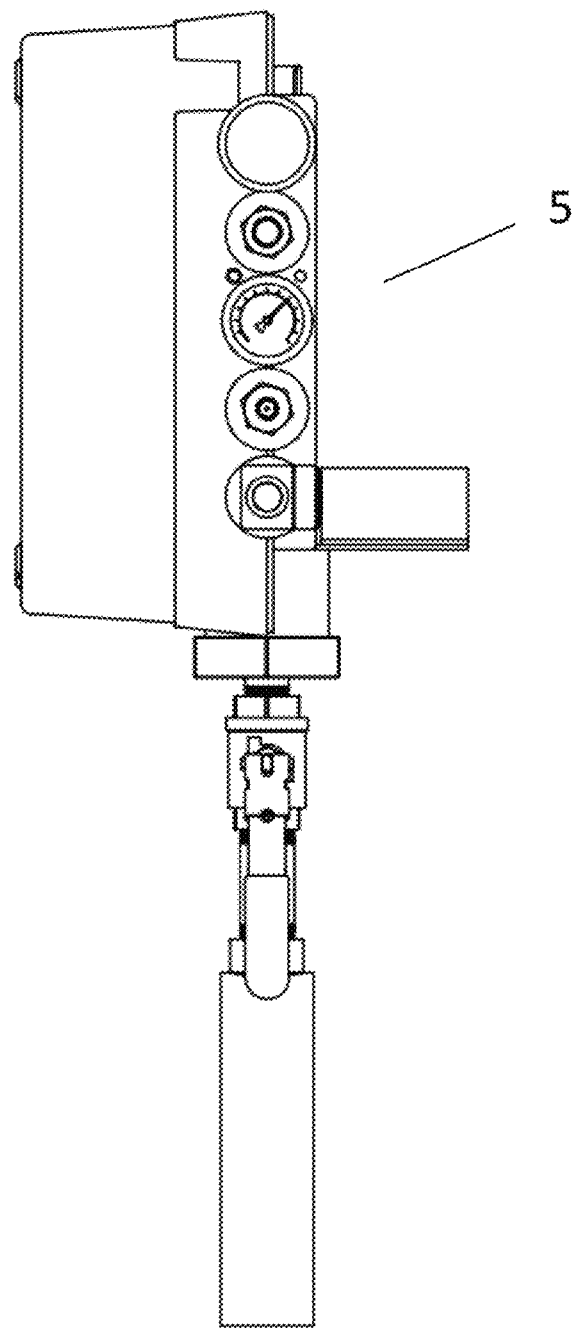
FIG. 9B is a side view of the invention of FIG. 9A.
Figure 9C:
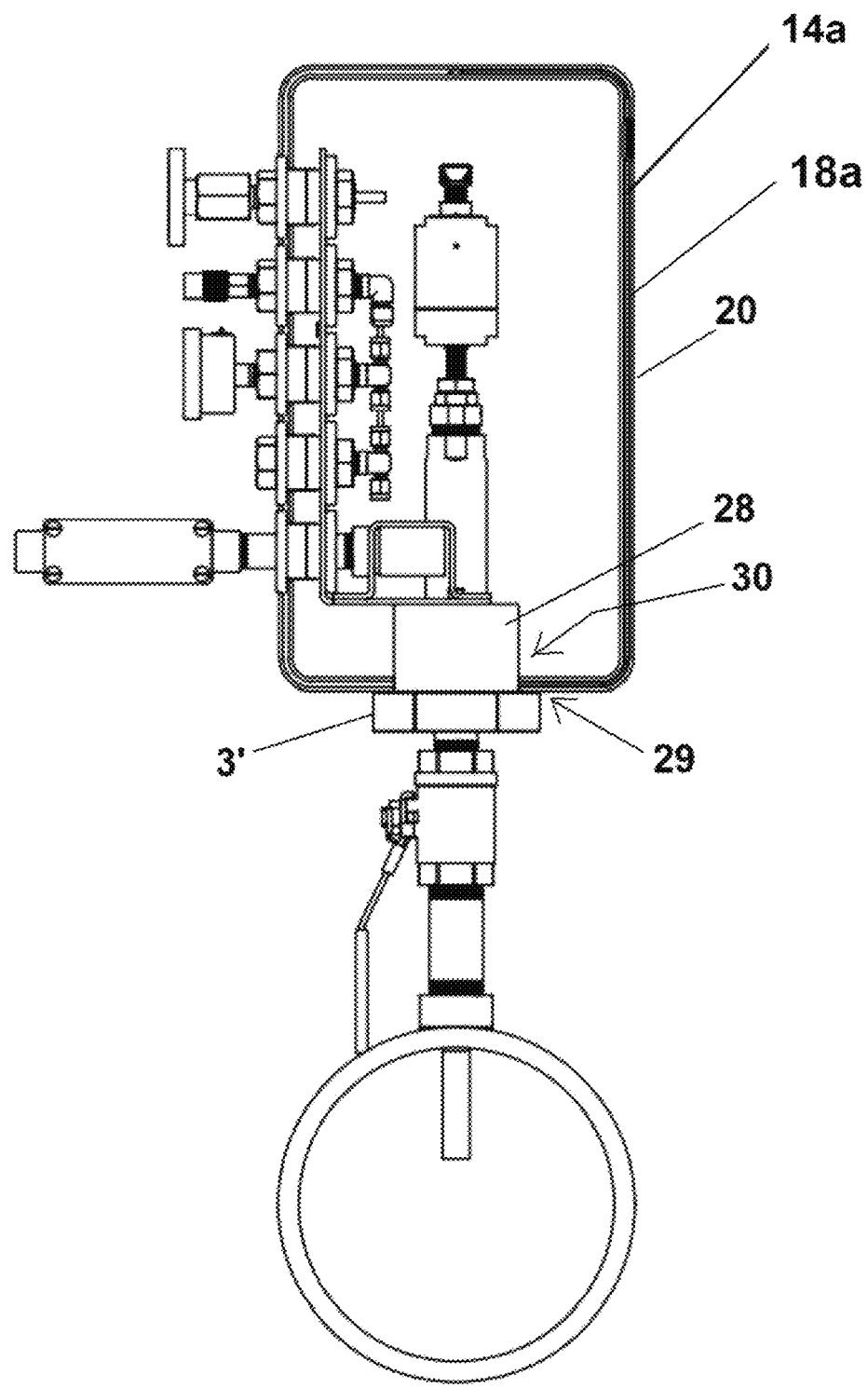
FIG. 9C is a frontal view of the invention of FIG. 9A.
Figure 10D:
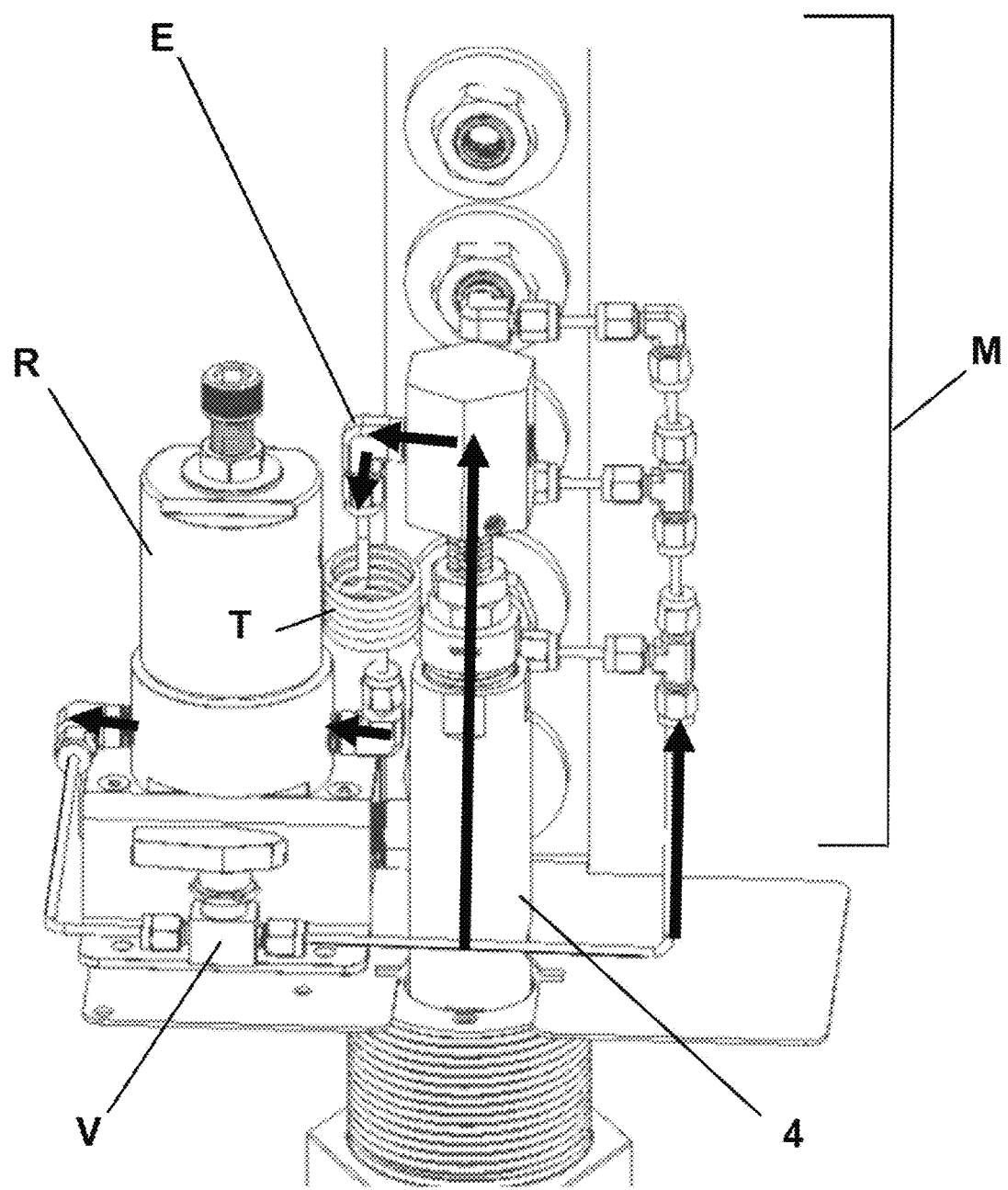
FIG. 10D illustrates a rear view of the modular sample conditioning components of FIG. 10A, illustrating the flow path of the pressurized fluid out of the extraction device 4, through an elbow to a tube T (coiled to allow positioning) leading to a regulator R, then out through a valve V to the modular components M.

FIGS. 8A, 8B, 10a-10c, and 12B shows a side 36' of first enclosure half 14a and second enclosure half 14b (also referred to as enclosure components) having formed or pre-drilled therethrough passages or holes forming module component access apertures 24a, 24b which, when the first 14a and second 14b enclosure halves are combined, forms a housing 20 having a series of holes or passages formed to encircle a portion of respective mounted modular components partially protruding therethrough for user access or monitoring, as well as providing a free-floating mounting of the housing to the modular conditioning system (i.e., a housing enveloping the substrate coupling, substrate bracket, and modular components mounted thereto, without the need for fasteners or the like to directly secure the housing to the enclosed system) while stabilizing same, as will be further discussed herein. The module component access apertures 24a are evenly spaced so that sample components can be arranged in various different orders or configurations. The holes formed in the side walls of the housing preferably align or coincide with those formed along the substrate bracket and the mounted modular components associated therewith. The enclosure slides onto and off of the rubber gaskets 18 at the substrate bracket. The enclosure is shown using alignment pins 17 to align the two enclosure halves 14a, 14b so that the module component access apertures 24a, 24b formed in the assembled housing 20 align with the module component mounting apertures 24, 24' situated on substrate bracket, and said enclosure halves 14a, 14b forming housing 20 are held in place with clasps 15, as shown in FIGS. 10A-10C. FIGS. 9A-9C shows one half of the enclosure 14a engaging 160 the module mounting area 23 of substrate bracket 6, modular components and substrate coupling 3, with the other enclosure 14b not yet installed, revealing the system being half enclosed. The module mounting area 23 of bracket forms a backplate 161 to facilitate a barrier and support behind the exposed modular components as well as engage, support and stabilize the enclosure halves forming the housing mounted thereabout. Alternatively, a separate backplate can be mounted to the module mounting area 23 via mounting aperture 162. Each half of the enclosure is completely independent and is held in alignment with the substrate bracket, for example, using the pin 17 for that half, which pin engages a separate mounting aperture (such as aperture 162) on module mounting area (or backplate), thereby affixing the respective enclosure half in position via and relative to the mounting area or backplate of the substrate bracket, while allowing easy disengagement therefrom, when access is required. Each half of the enclosure is completely independent and is held in alignment using the pin 17 for that half. The other half of the enclosure 14b can hang from the substrate bracket using its pin 17 (via cable 16) as shown in FIG. 10C. As shown in the figures, the base 3' of substrate coupling 3 has provided at least one tool engaging notch 3" disposed along its outer edge for receiving a tool, and facilitate engagement of same.

Continuing with FIGS. 2A-2C, 8A, 8B, 11B, 12B and 19-21A, the first 14a and second 14b enclosure halves forming housing 20 are formed to provide a mounting aperture 30 at the lower, centered, end 36 of the housing formed to allow the passage therethrough of the substrate coupling 3 in the vicinity of the substrate housing engagement area 28 of substrate coupling. In the first embodiment of the present invention as shown, the mounting aperture 30 has a diameter 30' formed to encircle or engage the housing engagement area 28 of substrate coupling, as well as utilize the edge forming the mounting aperture 30 of the housing, or gasket 18a associated with said edge of the housing, to rest upon the extended edge or extension 29 formed by the greater OD of base 3', utilizing same as a support surface, as well as a means of further stabilizing and anchoring the housing to the system.

The pins 17 are used for alignment when the enclosure is in place or to hold the enclosure temporarily as shown in FIGS. 10A-10C, when service or maintenance is required. Both halves of the enclosure 14a and 14b may be removed at the same time or installed at the same time or used one at a time independently, thereby allowing 100% access to the modular sample system for service or replacement.

The modular sample system can be completely replaced with a spare unit (another modular sample system 5) in the field as required or worked on at a component level with the component being repaired or replaced. This innovation allows a less skilled technician to operate in the field and a more skilled technician to operate back at the company home base or central service location.

FIGS. 10A-10C shows the enclosure halves 14a and 14b on the substrate bracket fitting around the gaskets 18 aligned to the substrate bracket with pins 17 and held in place with clasps 15. As shown, pins 17a, 17b are attached to enclosure halves (14a and 14b) with cables 16 to align and retain the enclosure halves forming the housing 20 or enclosure.

Figure 11B:
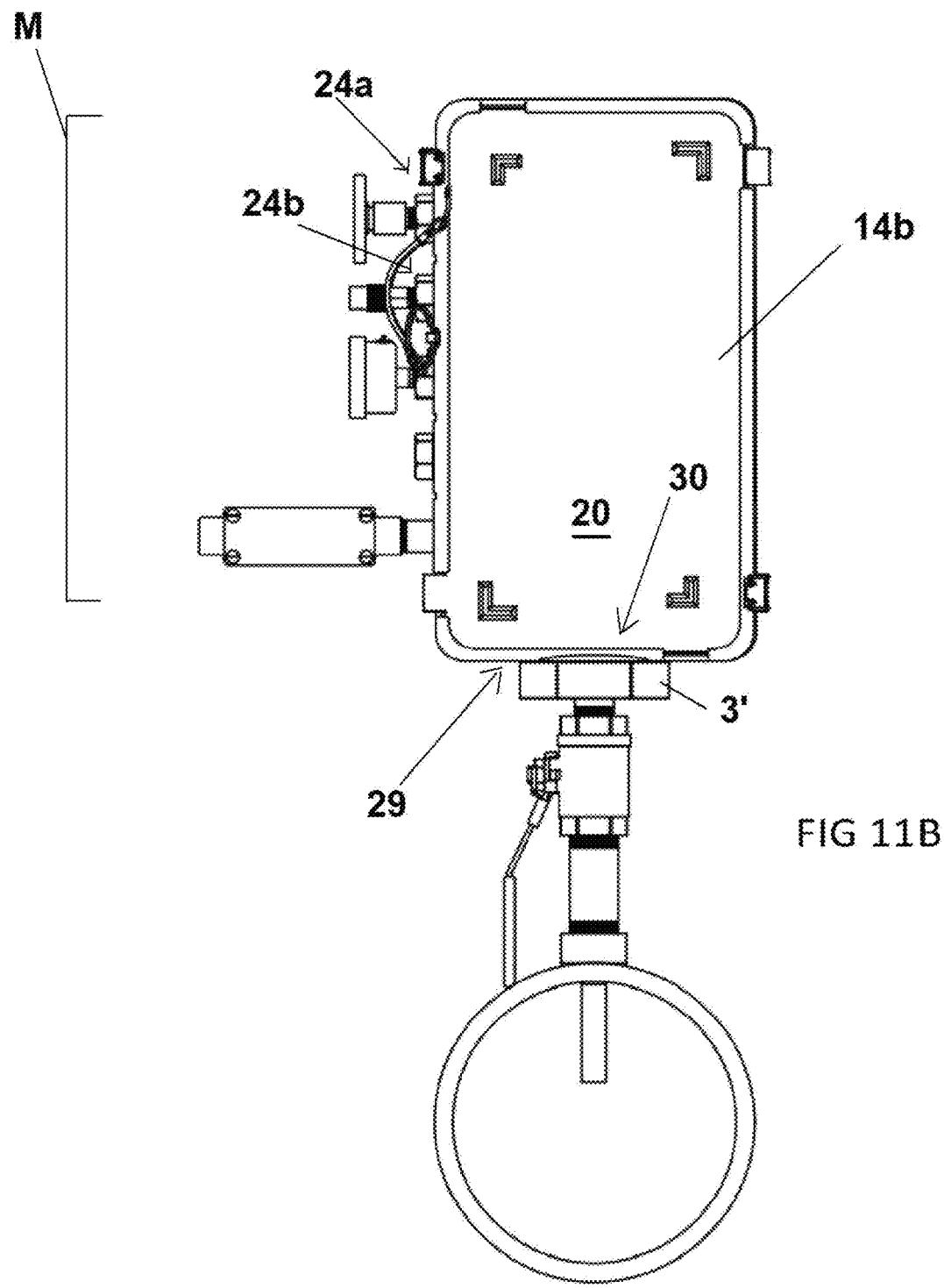
FIG. 11B is an end view of the invention of FIG. 11A.

FIGS. 11A, 11B show the completed modular sample system in the first embodiment, at the site of the pressurized gas source. The alignment pins (FIGS. 10A-10C) ensure that each housing or enclosure half 14a, 14b, is properly aligned with the docking platform. This feature also helps to ensure that the enclosure halves will not move due to pipeline vibrations. The same alignment pins are also used to hang the enclosure halves when service or maintenance is performed (FIG. 10C). This feature is useful to keep the enclosure half handy (within reach) and off the ground but also out of the technicians' way.

The housing formed by the joined enclosure halves (14A, 14B) with the openings are positioned and formed to engage the modular components where access outside the housing of parts of the modular components is desirable, providing visible components. Most components utilized in analyzer sample conditioning applications may be adapted for exterior use, even those not necessarily specific to natural gas or gas chromatography.

The visible components can be placed in any order that the application would require. The hole spacing (the holes formed in the housing by enclosures (14A, 14B) are preferably evenly spaced so the visible components may be placed in any order that makes sense for the particular application.

Exemplary modular components MC wherein visibility or other access exterior the housing would be advantageous for analyzer sample conditioning, for example, might comprise (in no particular order), pressure gauge(s), temperature gauge(s), outlet fitting(s), relief valve(s), and conduit connection(s), and the present system allows technician/operator access the exposed modular components external the enclosure or housing without having to open/disassemble same.

By allowing visibility access exterior the housing, the technician is able to read the pressure gauge, temperature gauge and other important data readings, as well as access the outlet fitting and inspect the conduit wiring and know that the relief valve is not activated. Other components such as tubing, fittings, valves, and any other conditioning components needed are not visible, remaining in the housing formed by enclosure components 14a, 14b, since they only need to be accessed for service or maintenance.

The present invention thereby provides visibility of components such as pressure gauge, temperature gauge, relief valve, outlet fitting, and conduit fitting without having to open or disassemble the enclosure (housing). This feature is in contrast with the prior art, which teaches a housing enclosure with pressure gauge and sight glass inside the enclosure as previously discussed. Unlike the prior art, the modular components in the present case can be arranged on the mounting bracket in any order using the substrate bracket design and matching enclosure design (housing) of the first embodiment of the invention.

Accordingly, with the housing formed by the enclosure components 14a, 14b (FIG. 11A) the first embodiment of the present invention, the modular sample system 5 (FIG. 9) is protected from the environment (via the housing) and can be temperature regulated or controlled, and yet the gasketed openings of the housing are formed to engage the periphery of desired components to provide exterior access/visibility of said components that require said access for operation.

This arrangement can accommodate a diverse selection of components such as electronic, electrical, flow control, etc. mounted into a non-customized substrate (the substrate bracket or mounting bracket) and housing (formed via enclosure components 14a, 14b), while allowing the components to be easily mounted into a customizable configuration along with protection from the environment and visibility of certain components, while providing 100% access to all components AND tubing when one or both enclosure components 14a, 14b forming housing are removed, while maintaining the rigidity of the system and not having to break any fittings or connection, or disassemble the system.

The present design is unique in that the substrate/mounting bracket is designed to structurally integrate with the two enclosure halves forming the housing and the mounted modular components so that, when assembled together, the structure integrated to substantially enhance rigidity, allowing mounting to the pressurized source via the unique substrate coupling 3, while allowing the extraction device 4 to pass through, in a stable overall structure.

To accomplish this enhanced structural rigidity, the configuration of the substrate bracket 6 is formed to have base 6a width 22 and depth 22a dimensions (FIG. 5) to closely approximate the interior width 20a and depth 20b of the base 20 of the enclosure formed by the combining of enclosure components 14a, 14b (FIG. 11A).

Further continuing with FIGS. 4-5, 11A, and 8A-9C, laterally emanating from the base 6a of the substrate bracket is module mounting area 23, which has formed therethrough multiple module component mounting apertures 24, 24', shown in generally uniform spacing along its length, said module mounting area having a length 23a formed to generally span the longitudinal length 21 (in the present example, along a sidewall) of the interior of the housing formed by assembled enclosure components 14a, 14b, so that the module component mounting apertures 24 are aligned with the module component access apertures 24*a*, 24*b* formed by the joined enclosure halves 14*a*, 14*b*.

When assembled, substrate coupling 3 is mounted to process isolation valve. Insertion probe 4 is then mounted to substrate coupling 3 via threaded connection, then a portion of its length passes through substrate coupling passage, through open isolation valve 2. Substrate bracket 6, which can have the modular components already mounted thereon forming the sample system 4, is mounted to substrate coupling 3. Referring to FIGS. 5, 6A-6B, 9A-9*c*, 11A, and 12C, modular components, which can vary depending on the application but might comprise, such as previously discussed, for example, a block heater 13, conduit junction box 12, NPT connection, 11, pressure gauge 10, relief valve 9, temperature indicator 7, or the like, each having a role in the conditioning, monitoring, or control of the sample, pass through 25 and engage via threaded connectors 26 or the like, the module component mounting apertures 24, 24'. Module component access apertures 24*a*, 24*b*, are formed about the respective modular components when the enclosure halves 14*a*, 14*b* are joined to form the housing with the access aperture 24*a*, 24*b* as they are positioned to encircle the respective mounted modular components.

Accordingly, external access to various mounted modular components is provided upon the joining of enclosure halves 14*a*,14*b*, to form housing 20. Simultaneously, the mounting aperture 30 at the lower end of the enclosure halves 14*a*, 14*b* forming housing are positioned to engage the cylindrical outer wall of the substrate housing engagement area 28 with said enclosure halves 14*a*, 14*b* being joined. The combined engagement of the engaged enclosure halves forming housing with the exposed modular components (which components are mounted to the substrate bracket) via component access apertures 24*a*, 24*b* and the engagement of the mounting aperture 39 about substrate coupling 3 thereby provides a structural integration with the mounting of the enclosure or housing to the system which enhances stability as well as the rigidity of the mount, while providing a "floating" case which envelopes and protects the modular sample system 5 without the need to affix the housing rigidly thereto, as the present system does not use or require fasteners to affix the housing structure directly to the system which it encloses, instead utilizing the housing configuration itself to engage said mounted modular components (via said modular component apertures) as well as the substrate coupling (via mounting aperture 30) to engage the lower wall of said housing about said substrate coupling.

While the housing 20 of the present invention may be formed to two relatively rigid enclosure halves 14*a*, 14*b*, it is emphasized that said halves may be fabricated of a flexible material and provide similar functionality, so the present system is not intended to be limited to rigid housing(s).

The present system thereby provides easy and full open access to the interior of the housing/enclosure and associated modular components or the like sheltered therein (components shown mounted to substrate bracket), by simply separating and removing enclosure halves 14, 14*b*.

The base 6*a* of substrate bracket 6 (FIG. 5) mounts to the substrate coupling 3 via substrate coupling engagement slots 19, which are formed to align with threaded passage 3*b* formed in base 3*a* of substrate coupling 3.

Accordingly, in the preferred embodiment of the invention, the horizontal portion of the base 6*a* of substrate bracket 6 (rectangular base) has dimensions that approximate the interior base of the enclosure. Also, the vertical portion of the base substrate spans the length of the enclosure. This design makes the sample system rigid and independent of the enclosure (i.e. able to "stand alone") allowing 100% access to all components and tubing for service, maintenance, and replacement.

Conversely, the prior art has used a backplane or panel that was fastened to the back of the enclosure. Components were fastened to the panel and were only accessible if the cover was unbolted or opened. The present invention overcomes these issues.

Figure 12A:
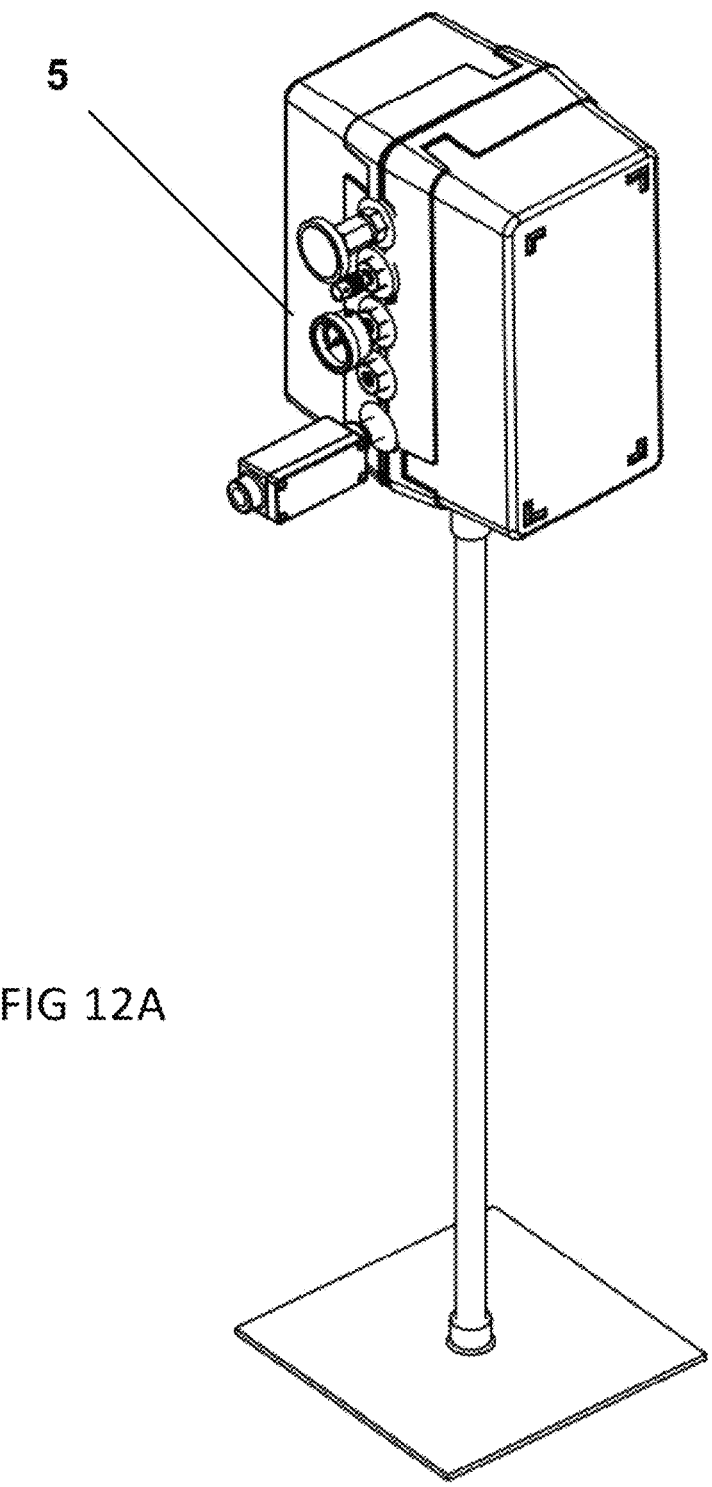
FIG. 12A is a perspective view of a second, alternative embodiment of the present invention, illustrating the housing enclosure enclosing the modular sample system as a stand-alone location situated between the source and the analyzer.
Figure 12B:
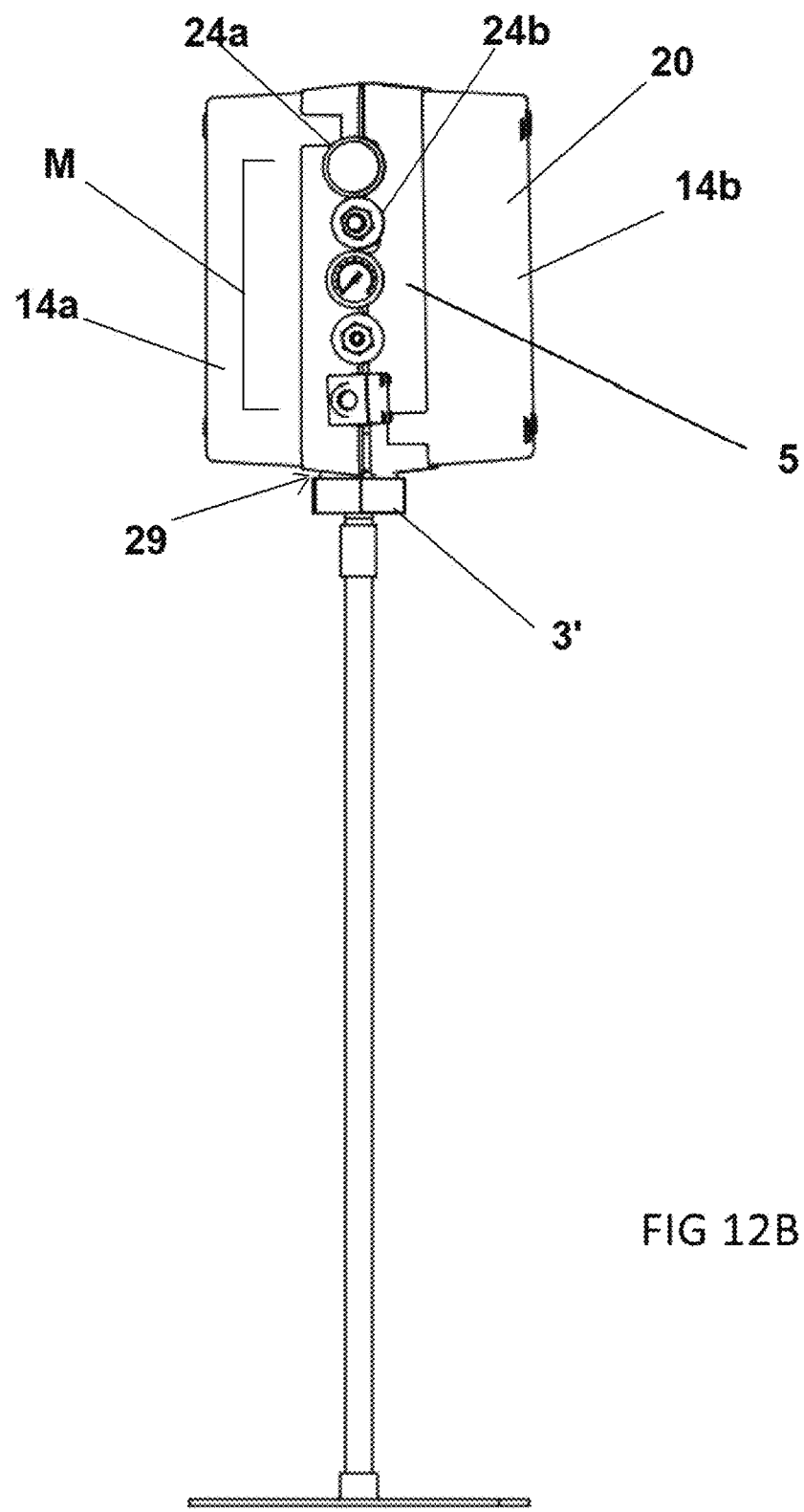
FIG. 12B is a frontal view of the invention of FIG. 12A.

A second embodiment is shown in FIGS. 12A-12B, where the modular sample system 5 is not required to be situated at the pressurized source but is instead at a stand-alone location between the source and the analyzer. All of the benefits and features described above would apply to this location as well. It may be desirable to have one modular sample system at the pressurized source with one configuration and a second modular sample system with a different configuration between the source and the analyzer.

Figure 13:
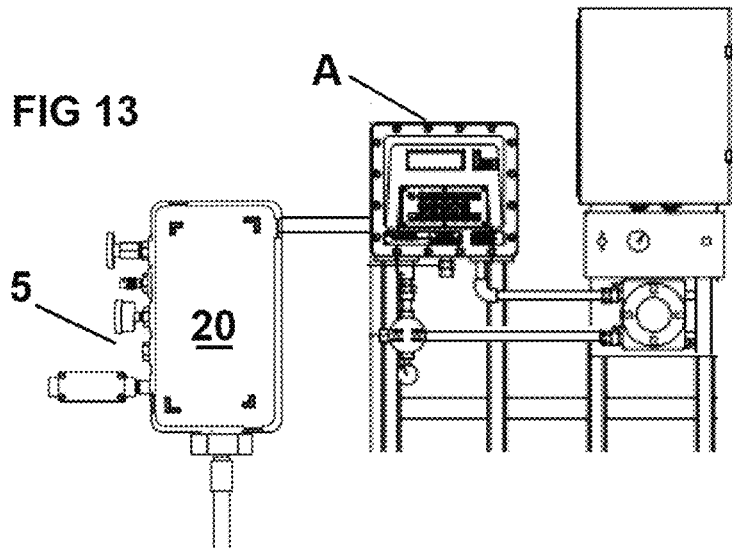
FIG. 13 is a frontal view of a third, alternative embodiment of the present invention, wherein the modular conditioning mounted on the substrate bracket/mounting bracket and enclosed by the housing/enclosure, at the location of and just prior to a stationary analyzer.

A third embodiment is shown in FIG. 13, where the modular sample system is used at the same location as the stationary analyzer A, or configured into the analyzer.

Figure 14:
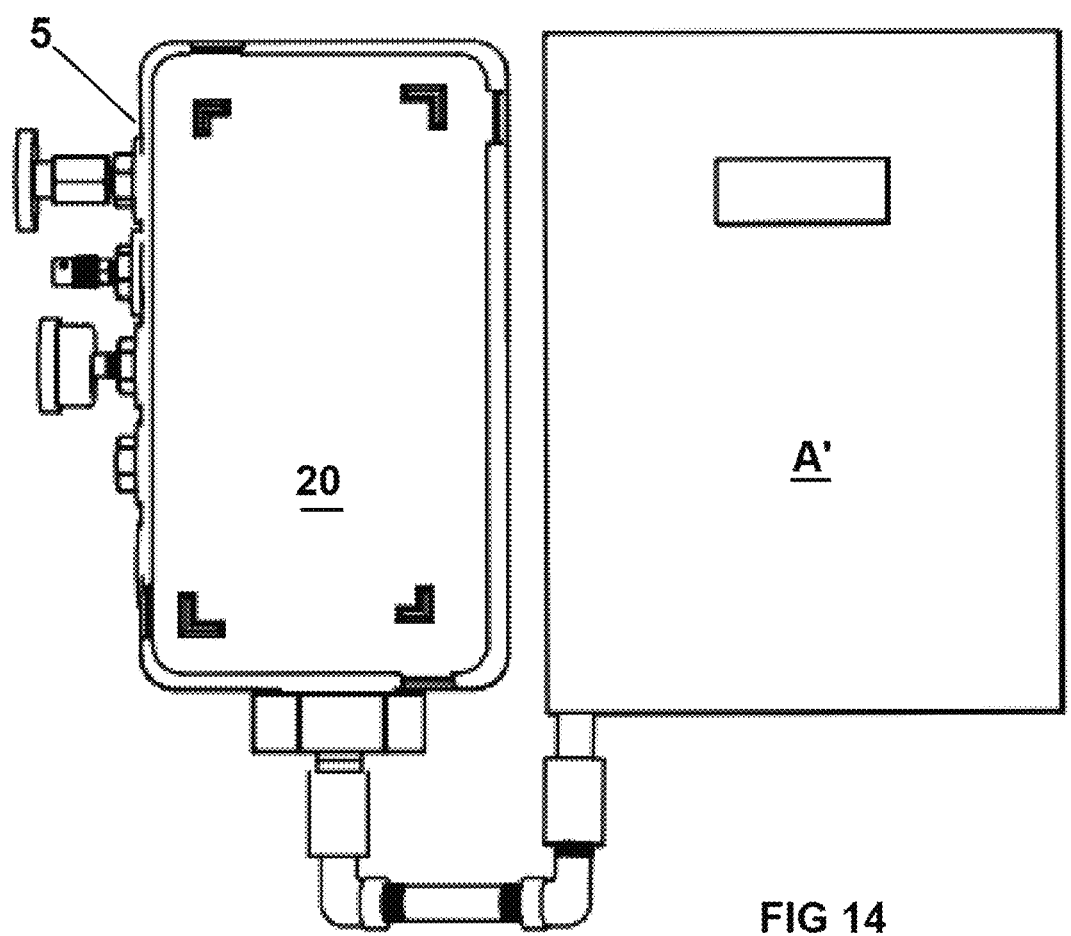
FIG. 14 illustrates a side view of still other embodiments of the present invention illustrating the modular sample system of the present invention integrated with a portable analyzer.
Figure 15:
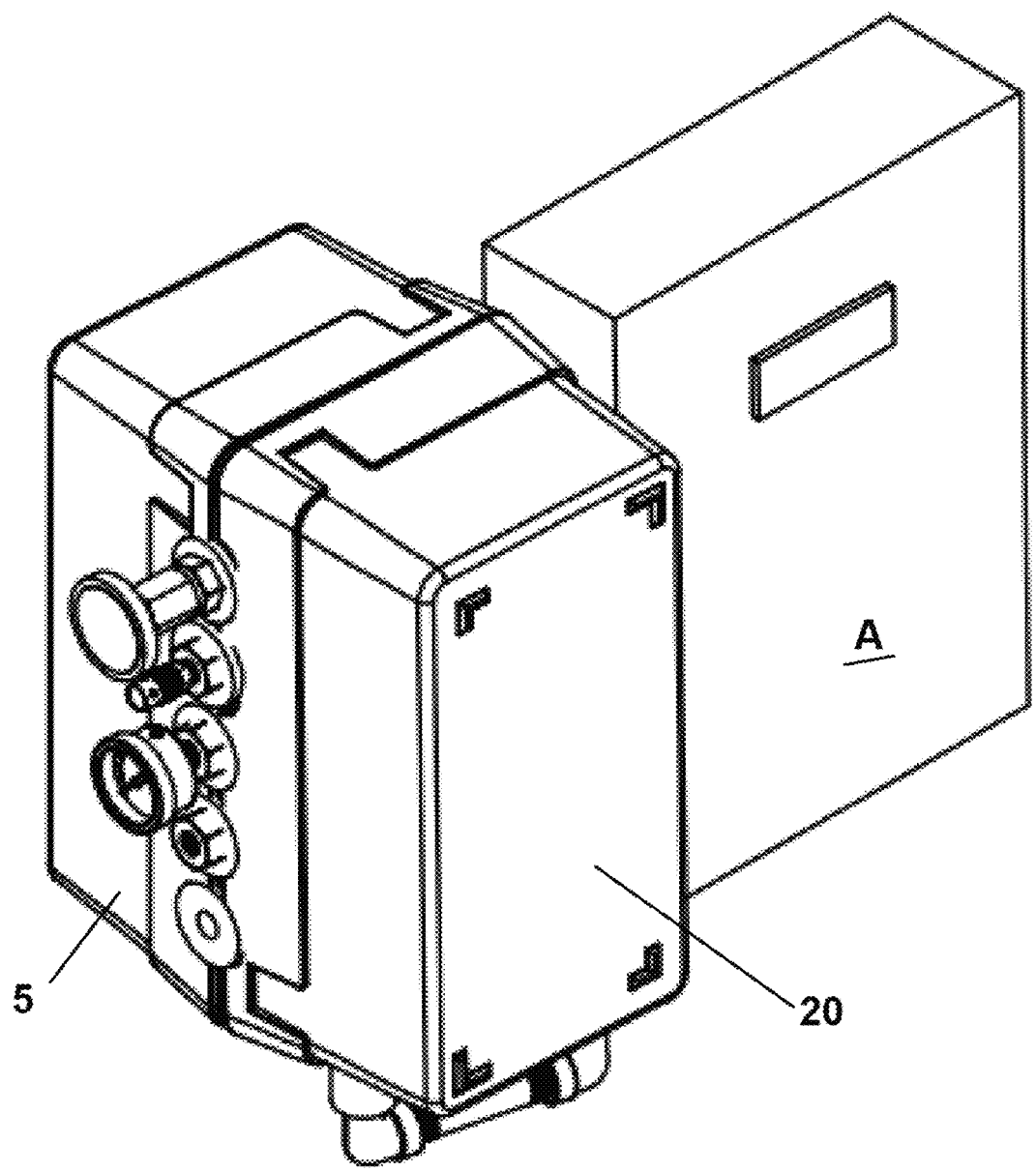
FIG. 15 is an isometric view of the invention of FIG. 14.

A fourth embodiment could include sample conditioning systems situated upstream the analyzer A' (FIGS. 14-15).

A fifth embodiment includes the analyzer and modular sample system mounted together at the source of the sample, which could include the analyzer and conditioning system sharing the same support bracket and housing.

Flexible Insulated Housing Enclosure Embodiment

FIG. 22 is a side view of an alternative embodiment of the invention, having the substrate coupling 3, substrate bracket 6, isolation valve 2 mounted to conduit C or pipe, and/or extraction device 4 (shown as insertion probe), and can include a heat trace 37 instead of a heater block and power cable (for example, as shown in FIG. 7A-C), the present embodiment providing the heated sample to one or more mounted modular conditioning components M' or the like, and without the necessity of a power cable.

Referring to FIGS. 22, 23 and 23A, as opposed to a bifurcated, rigid or semi-rigid enclosure, the present illustrated embodiment provides flexible insulated housing 38, the housing shown retained in place by a releasable fastener such as hook and loop (i.e., VELCRO brand) (as further disclosed herein) and to anchor same about protruding portions of modular conditioning components 5 situated therein while allowing heat trace 37 to pass therethrough. As shown, the flexible, insulated housing 38 or enclosure in the exemplary embodiment illustrated is formed of, as an example, a weather resistant, exterior or outer layer of material 71 comprising about $\frac{1}{32}$" thick woven polyester with an acrylic coating, an interior layer 71' (the layer forming the inner wall of the housing 38) comprising $\frac{1}{32}$" 4 ply polyester, and an inner insulating layer 72 comprising about $\frac{3}{8}$" EPDM foam rubber or the like situated between the outer layer 71 and interior layer 71'.

In addition, one or more webbed straps can be provided which are easily trimmable to fit the application are provided for securing the unit, and while the straps can vary in length, typically they are provided at about 36" length, for example. The exemplary system would provide an R value of about 1.7R@ $\frac{1}{2}$". The materials would allow usage in as low as −50 degrees C., or as high as about 150 degrees C. The above specifications are for exemplary purposes only, and the material and the amount of insulation can vary depending on the environment and operational criteria.

The housing 38 has a top 39 or cover section and either an open bottom 39' (which can engage and be enclosed by either conduit C, or the base of substrate bracket 6' (6a' in FIG. 27B)), or a bottom panel can be provided having a slit or passage formed therein for allowing the passage of a supporting conduit or the like therethrough. The housing 38 further has a sidewall 40 joined along its upper edge 45" with top 39 or cover section, and defined corners 40', 40" can be provided to facilitate the illustrated, exemplary rectilinear configuration, although this shape is not intended to be limiting and can vary depending on the application. The sidewall 40 is longitudinally split in the front center to form first 58 and second 58' front panels having first 41 and second 41' edges, respectively, said edges joined by fastening straps or the like as further discussed herein, providing an insulated enclosure about the modular sample system M'.

Figure 24A:
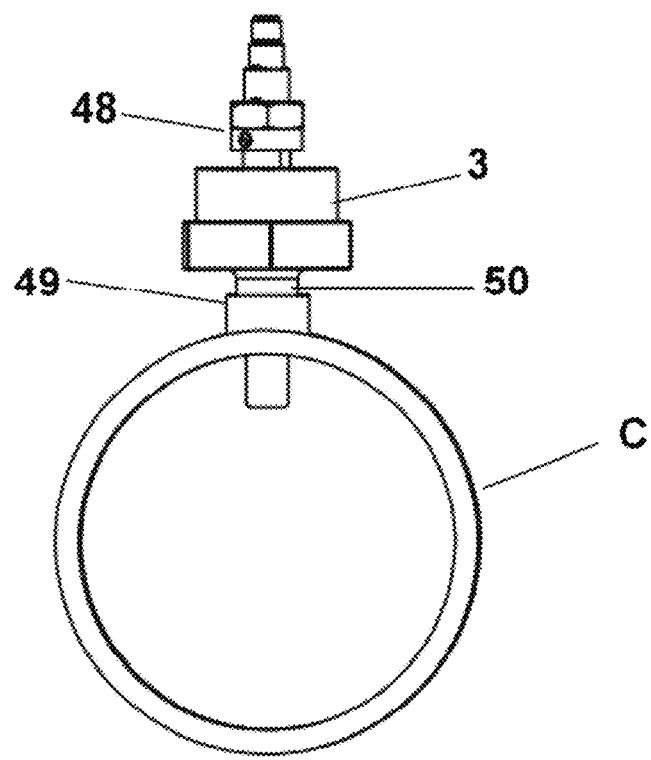
FIG. 24A is a side view of an embodiment of the present invention illustrating the substrate coupling 3 mounted directly to threaded conduit aperture 49 via threaded nipple 50, providing a passage to conduit C, having mounted thereto a fixed (non-insertable) probe such as the GENIE brand GP2 membrane probe 48 by A+ Corporation LLC of Gonzales, La.

FIG. 24A is a side view of still another embodiment of the present invention, wherein there is provided a substrate coupling 3 mounted directly to threaded conduit passage 49 via male threaded connection 50 emanating from underside of coupling 3, providing a passage to conduit C, having mounted thereto a fixed (non-insertable) probe assembly such as the GENIE brand GP2 membrane probe 48 by A+ Corporation LLC of Gonzales, La., as described in GENIE GP2 Membrane Probe product sheet SCC-GP2-PS_0016, the contents of which are incorporated herein by reference thereto. The present system may be utilized with a heat trace 37' mounted to probe 48, as shown in FIG. 24B.

Figure 24B:
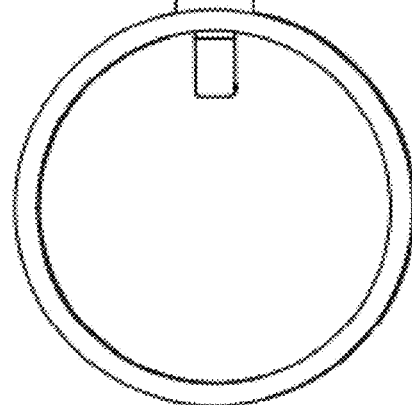
FIG. 24B is a side view of the invention of FIG. 24A, with heat trace 37' mounted to the probe 48.
Figure 26C:
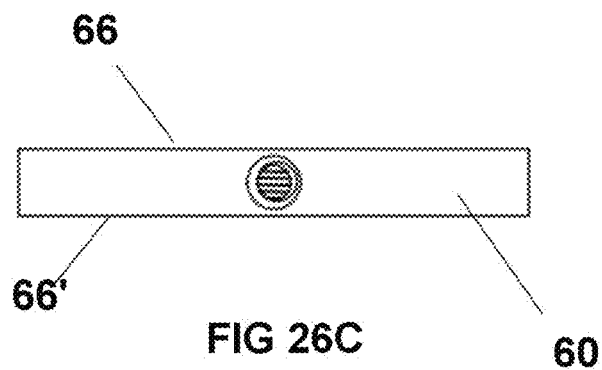
FIG. 26C is a side view of the flange forming the substrate coupling 51 of the invention of FIGS. 26A-26B.
Figure 26F:
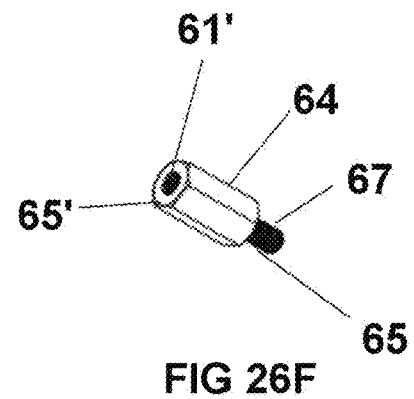
FIG. 26F is an isometric, side view of a spacer for use with the substrate coupling of the invention of FIGS. 26A-26C.
Figure 26D:
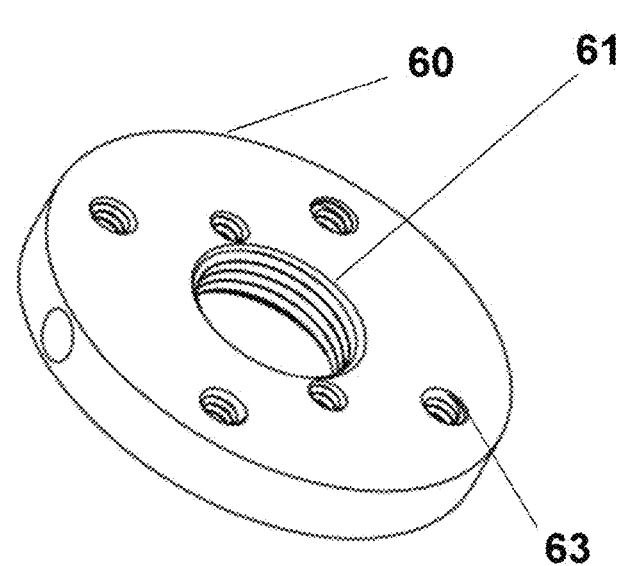
FIG. 26D is an isometric view of the flange forming the substrate coupling of the invention of FIGS. 26A-26C.
Figure 26E:
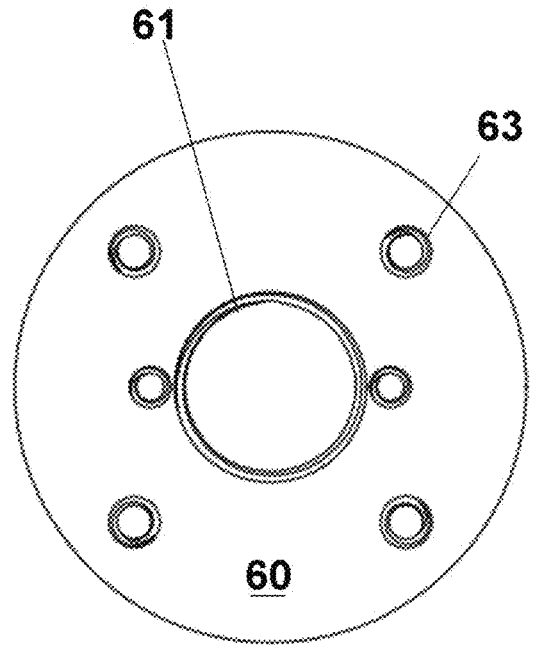
FIG. 26E is a top view of the invention of FIG. 26D.

FIG. 25 is a side view of the invention of FIGS. 24A-24B, with substrate coupling 3 having mounted thereto substrate bracket 6 supporting mounted modular conditioning components M' and heat trace 37', which heat trace engages probe 48 to provide a heated sample flowing to regulator R' from conduit C, and to modular conditioning components comprising the modular sample system. This system can likewise be enclosed by the insulated housing 38 (as shown in FIG. 23).

FIGS. 26A-26E illustrate an alternative configuration substrate coupling 51 that is more economical to manufacture, as well as providing a quicker and less complicated installation when compared to the substrate coupling 3 shown in FIG. 25.

The present embodiment is shown utilizing (as an example) the GENIE GP2 membrane probe assembly P, which comprises a probe housing 75 having first 76 and second 76' ends and a passage 76" therethrough for receiving insertion probe 74, in this case, a membrane tip probe. In the present exemplary embodiment, the second end 76' of the probe housing 75 has a foot valve 77 which is normally closed but which is formed to open when the membrane tip probe is inserted to engage the second end of housing, allowing the flow of pressurized fluid from the conduit C through the probe 74. The probe housing 75h as formed on its exterior length a threaded area 62 for engaging a threaded passage (in this case, the central threaded passage 61 in flange 60 forming substrate coupling 51 as discussed herein) providing a sealed passage through same. The probe housing 75 further includes a threaded area for threadingly engaging a threaded passage to the interior of the pipe or conduit C, providing sealed access to allow the second end 76' of housing to be placed therein.

Details on the features of the GENIE GP2 membrane probe 48 can be found in U.S. Pat. Nos. 6,357,304, 6,701,794, 6,904,816 and 7,004,041, the contents of which are incorporated herein by reference thereto.

As shown, substrate coupling 51 comprises a flange 60 (shown circular and formed of approximately 0.4" thick, number 316 stainless steel, although the configuration and material can vary) the flange 60 having first 66 and second 66' ends with a central threaded bore 61 (prior referenced GP2 membrane probe shown as an example) formed to engage and be supported by probe 48', via engagement of threaded area 62 of a probe 48'. Threaded passages 63, 63', 63" are situated about central bore 61 of flange, which are formed to engage threaded ends 67, 67',67", of spacers 64,64',64", respectively. Spacers 64, 64', 64" have first 65 and second 65' ends, the first end of spacers engaging the first end 66 of flange 60 via threaded ends 67, 67', 67", the second end 65' of spacers providing mounting surfaces 68, 68', 68' to engage and support (via threaded bore or the like) substrate bracket 6', respectively, as further illustrated in FIGS. 27A and 27B.

Referring to FIGS. 26A-28B, substrate bracket 6' (with base 6a' plate) is mounted to mounting surfaces 68, 68', 68" of alternative substrate coupling 51 via threaded fasteners or the like and has mounted thereto modular conditioning components M" and heat trace 37', which heat trace may engage probe 48 so as to heat said probe and any sample passing therethrough. Alternatively, the heat trace can be used to provide heat to a regulator (such as, for example, as provided by the GENIE brand GPR Probe Regulator by A+ Corporation LLC) for receiving fluid from said probe, so as to regulate and heat same, or other component(s) as required, or be situated within the enclosure so as to heat its contents (e.g., including the probe, lines, modular components, and other apparatus).

FIGS. 28A and 28B are side and frontal view, respectively, of the substrate coupling 51 with substrate bracket 6' (having base plate 6a') supporting mounted modular components M" and heat trace 37' engaging probe 48, mounted to conduit C or pipeline.

Accordingly, the probe housing can 75 be mounted 73 to the pipe or conduit C so that the second end 76' of housing is situated therein, with the foot valve 77 closed to prevent pressurized gas escaping until the insertion probe 74 is placed therein. The substrate coupling 51 can then be mounted to and supported by probe housing via the threaded area 61 of probe housing 75. The substrate bracket 6 can then be mounted to substrate coupling 6, then the modular components M", at which point the insertion probe 74 is placed into probe housing, with appropriate piping to facilitate flow from the fluid stream in pipe or conduit, through the insertion probe, to modular components M". As discussed, this may include use of a heat trace to provide heat to the system within the housing.

FIGS. 29 and 29a illustrate the flexible insulated housing/ enclosure 38 of the present invention mounted 69 to the conditioning components M' forming the modular sample conditioning system of FIG. 25 enveloping the substrate bracket and coupling (not shown), with portions of the mounted modular conditioning components M' and heat trace 37 passing and thereby exteriorly accessible, with the bottom of the housing/enclosure resting on the pipe or conduit C As shown, the housing/enclosure 38 is mounted to the modular sample conditioning system, enveloping and containing the mounted conditioning components, the substrate bracket and substrate coupling (not shown as contained within housing/enclosure 38). The housing is anchored in place via fastener strips 43, 43', 43" provided to engage and retain the opposing edges 41, 41' of the housing/enclosure 38 in place as well as securing the housing to the conditioning components, the strips covering the spaces 44, 44', 44" between the conditioning components passing therethrough for exterior access/visibility as well as securing the flexible housing/enclosure 38 in place via the protruding mounted modular conditioning components M' as well as any other items passing therethrough including heat trace 37, with no other means of anchoring same generally required.

FIG. 30A shows the flexible insulated housing 38 having provided raised 45 first and second edges 41, 41', respectively, each said edge having a fastener strip situated thereupon along its length. A plurality of straps 43, 43', 43" are releasably adhered to said edges 41, 41' such as via hook and loop fastener (although belts, cinches, buttons, snaps, clips, clamps, zippers, pins and other means of fastening/retaining may be similarly utilized), providing flexibility in accommodating modular conditioning components, heat trace, power cables, sample conduits and other components or the like which protrude or pass therethrough, while filling any open spaces thereabout/therebetween.

Figure 30B:
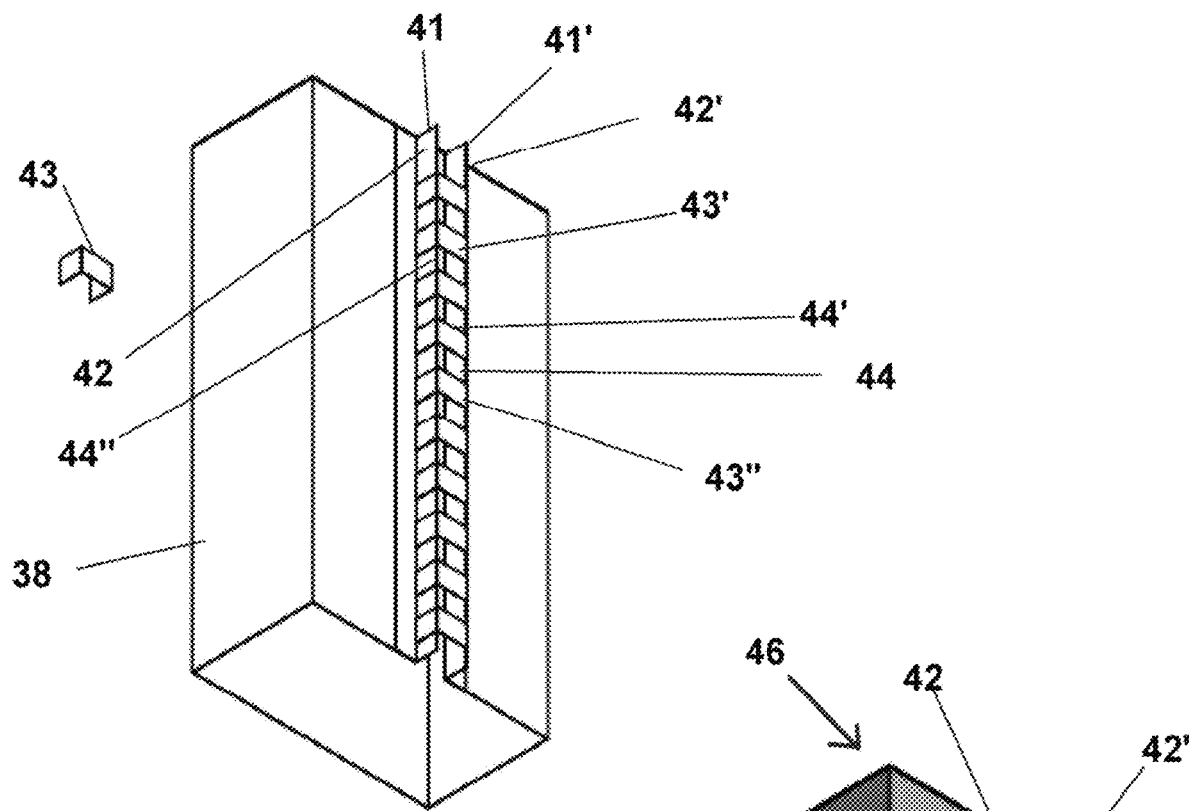
FIG. 30B is an upwardly oriented, perspective line drawing illustrating the flexible insulated housing 38 of FIG. 30A, showing the raised 45 edges 41, 41' having in the present example fastener strips 42, 42' along their length, for example loop strips for engaging hook fasteners situated on fastener straps 43, 43', 43", or visa-versa, and positioning of the straps to form spaces 44, 44', 44" for the passages of components therebetween, as well as the open bottom 46' formed to pass over and about the area to be enclosed, and engage the base 6a or 6a' of substrate bracket 6 or 6' respectively (as shown in FIGS. 5 and 27A, respectively), as well as a top joining the upper, back, sidewalls, and front panels (as further discussed herein).
Figure 30C:
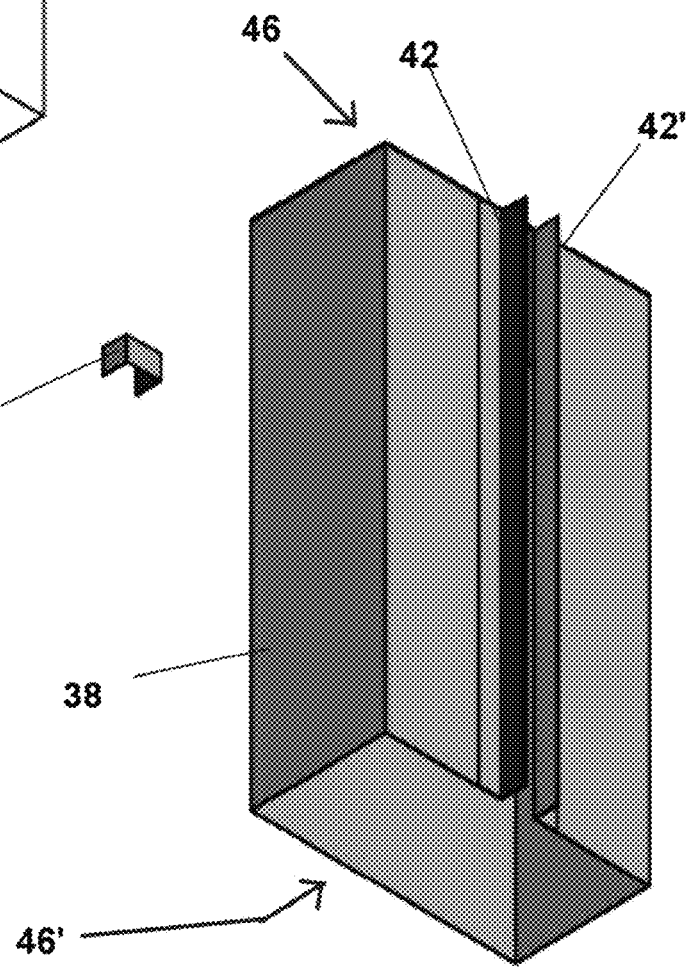
FIG. 30C is a greyscale view of the flexible insulated housing 38 of FIG. 30B, further showing top 46.
Figure 30D:
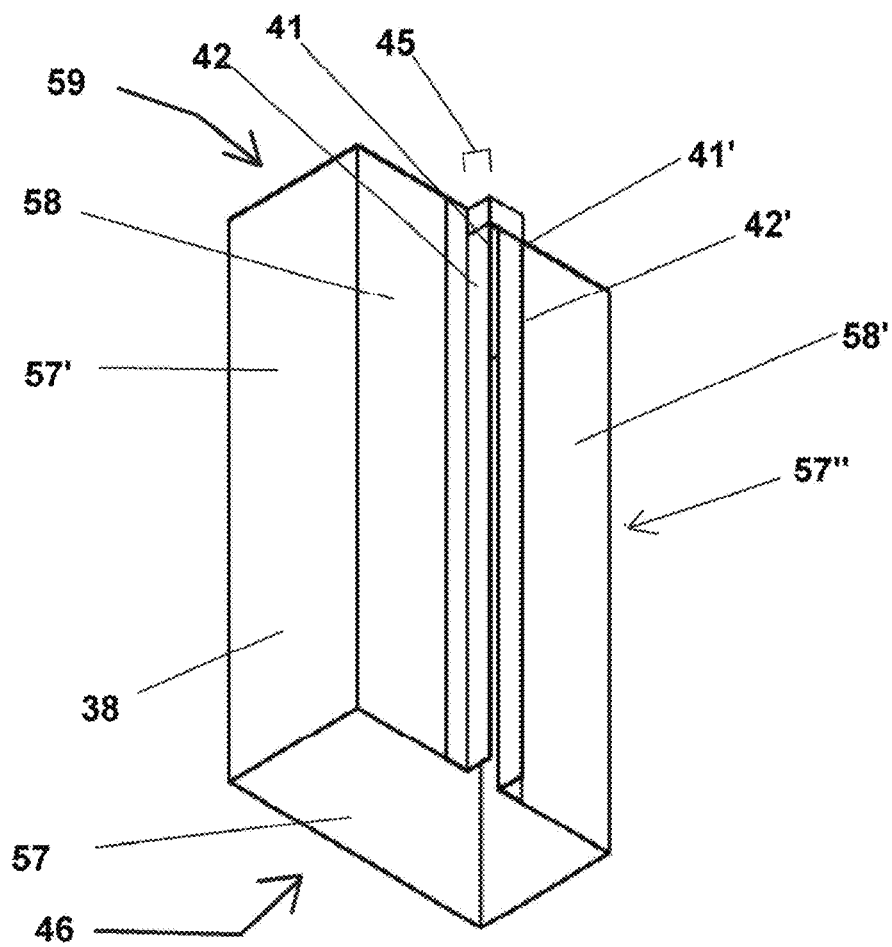
FIG. 30D is an upwardly oriented line drawing of the inventions of FIGS. 30A-30C, without the fastener straps shown, further showing upper 59 back 57, sidewalls 57', 57" and front panels 58, 58'.
Figure 30E:
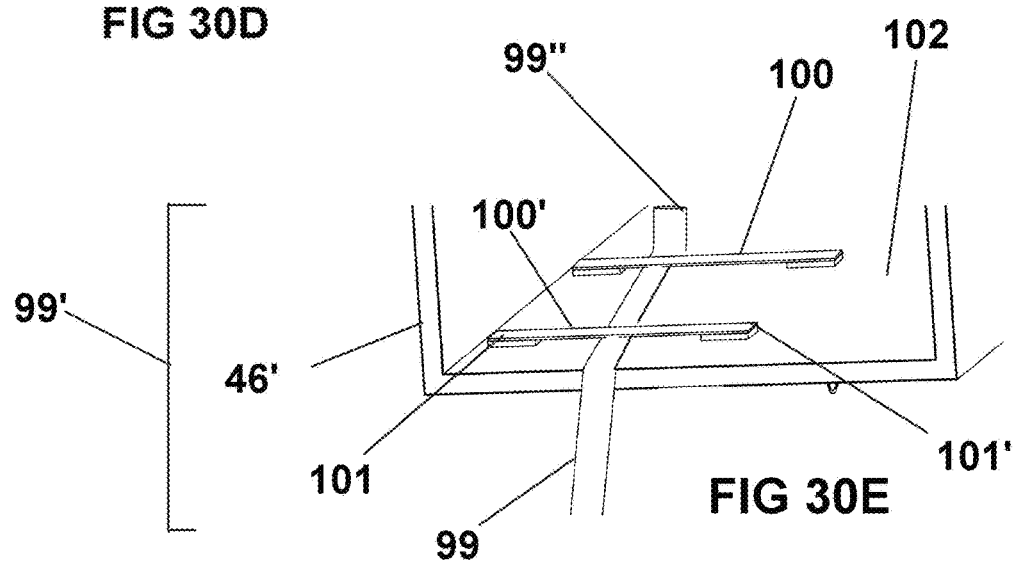
FIG. 30E is a perspective view of the underside of the flexible insulated housing of the present invention, illustrating an alternative mounting of the heat trace 99, which is shown passing into the open bottom 46' of the housing, and between retaining straps 100, 100' and the inner surface 102 of housing, so as to provide heat to the enclosure and items situated therein.

FIGS. 30B-30D illustrate the flexible insulated housing 38 of FIG. 30, showing the raised 45 edges 41, 41' having (in the present example) fastener strips 42, 42' along their length, for example loop strips for engaging hook fasteners situated on fastener straps 43, 43', 43", or visa-versa. The figures further illustrate an exemplary positioning of the straps 43, 43', 43" to form spaces 44, 44', 44" therebetween to provide passages for the passing of a portion of conditioning components therebetween. Further shown is the bottom 46' of housing/enclosure 38, the bottom may be open to provide space to pass over and about the area to be enclosed, and engage the base 6a or 6a' of substrate bracket 6 or 6' respectively (as shown in FIGS. 5 and 27B, respectively), as well as a top 46 joining the upper 59 back 57, sidewalls, 57',57" and front panels 58, 58', forming an enclosure therein. Alternatively, there may be provided bottom flap or separate panel which is formed to enclose the bottom portion of the housing/enclosure 38, and which may be retained in place via straps, hook and loop, buttons, snaps, zipper, etc. Said bottom flap or separate panel may include separation lines or cut-outs to accommodate supports, conduits, wires, or other items passing through the bottom as would be found in various installations.

FIG. 30 E is a perspective view of the underside of the flexible insulated housing of the present invention, illustrating an alternative mounting of the heat trace 99 which has a length 99' and end 99", which is shown passing into the open bottom 46' of the housing, and between retaining straps 100, 100' and the inner surface 102 of housing, so as to provide heat to the enclosure and items situated therein. As shown, the retaining straps 100, 100' have opposing ends affixed 101, 101' to the inner surface 102 of housing, with the length therebetween unattached, allowing passage of the heat trace 99 therebetween.

FIGS. 31 and 31A are front and side views, respectively of an alternative flexible insulated housing/enclosure 38' utilizing belts 52, 52' with buckles 53, 53' or cinches to secure the housing, the belts, 52, 52' positioned to fit around the components 47, 47' which pass through space 54 between the edges 55, 55', the housing/enclosure 38' having a top 5. By tightening 70 the straps, the edges 55, 55' are brought closer together, while the flexible material forming the housing/enclosure 38' gathers at the components 47, 47' passing therebetween. In addition, an insulating strip can be provided which can have passages in pre-cut punch out, or pre-formed weakened tear lines, so as to allow the user to customize the strip to accommodate the particular configuration, or the strip can be formed of a material allowing one to form the slits required so that the components to pass therethrough, while blocking any spaces between the components so as to provide complete enclosure of at least the sides and top of the system.

Analyzer Enclosure Embodiment

Figure 32C:
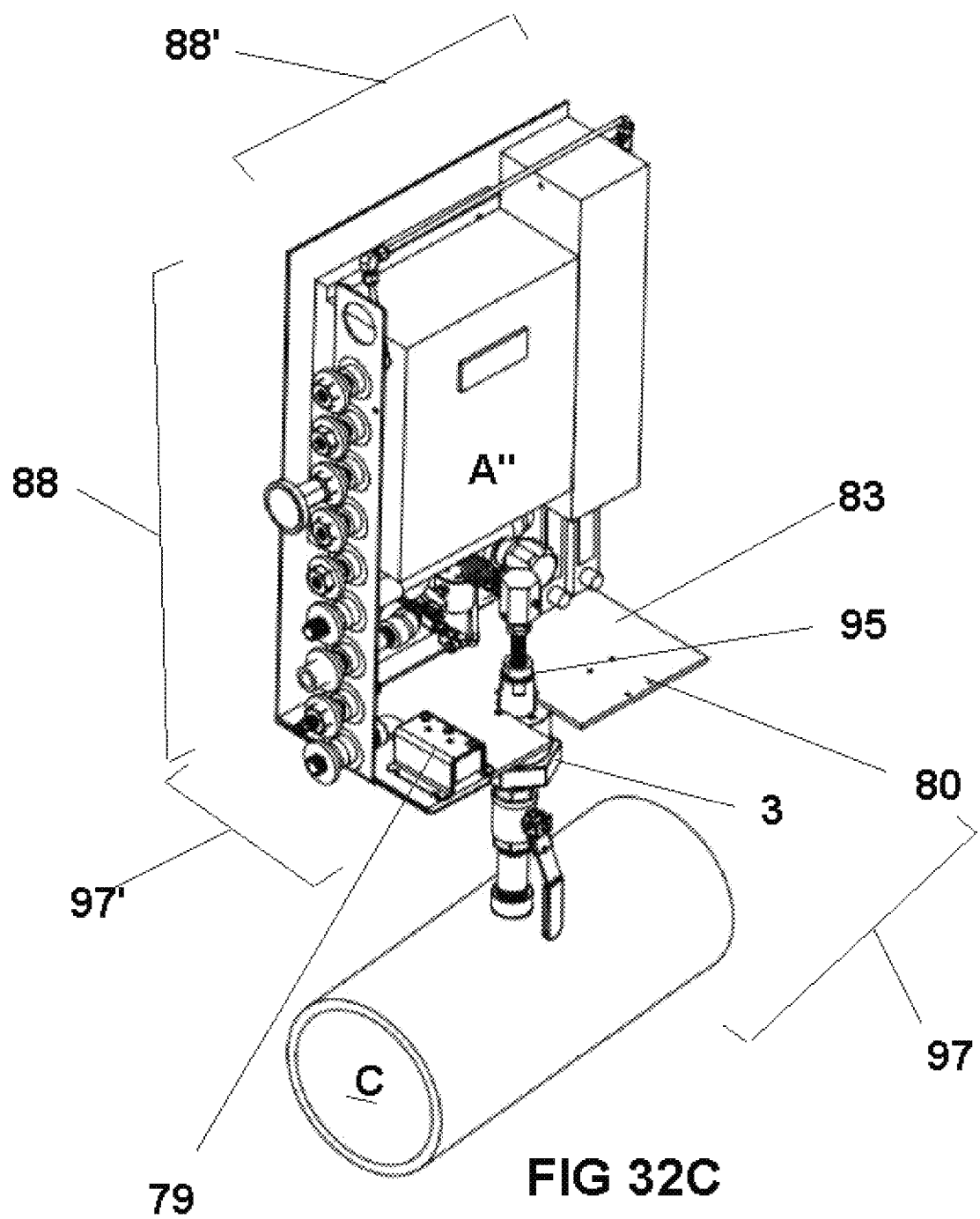
FIG. 32C is a perspective view of the invention of FIG. 32B, wherein there is further provided an analyzer for receiving conditioned fluid from the mounted modular components M", said analyzer mounted to side panel 82.

FIGS. 32A-32C illustrate an alternative substrate bracket 80 to the previously described substrate bracket 6 of FIG. 5, the present substrate bracket 80 further comprising a side mounting panel 82 situated in orthogonal orientation relative to the module mounting area 81 as well as the base 83, the module mounting area 81, side mounting panel 82 and base 83 formed to receive and have mounted thereto modular components 78, 78' (along module mounting area 81), components 87, 87', 87" (along side mounting panel 82) and one or more components 79 on base 83. As with the earlier embodiment of FIG. 5, base 83 of the present alternative substrate bracket 80 has a width 97 and depth 97' forming the base of the modular conditioning system, and has a substrate coupling engagement slot 85 formed in base 83, which, like the earlier embodiment is formed to engage the substrate couplings (3 or 51) and support configurations as described hereabove.

The side mounting panel 82 is formed to receive, support, and have mounted thereto additional components including, for example, one or more analyzers A" (for example, including but not limited to an optical analyzer(s), gas chromatograph, spectrometer, etc), as well as other modular components 87, 87', 87", regulators, transceivers, and other devices within a housing 94, which can have a construction and operative functionality as shown, for example, in the bifurcated enclosure 20 (FIGS. 11A-B, 12B, 13-15, etc) or alternatively the flexible insulated housing enclosure 38 (FIGS. 23, 29-30D) or alternative 38' flexible insulated housing enclosure (FIGS. 31-31A).

As shown, the substrate bracket 80 in the present embodiment is mounted to substrate coupling 3, which in turn (as shown the embodiment of FIG. 7A and elsewhere herein) is mounted to a conduit C or pipeline (although the system can also be mounted to an independent support or various other configuration mounts, depending upon the circumstances of use). The embodiment of FIG. 32B illustrates the system in use with an insertion probe 95, for example, the GENIE brand GP2 membrane probe 48 by A+ Corporation LLC of Gonzales, La. the first end of the probe shown emanating from the substrate coupling 3, the second end of probe inserted into and receiving fluid from the conduit C or pipe so as to facilitate the flow 96 of a fluid sample to a regulator and/or various modular components mounted to the side mounting panel 82 and/or module mounting area 81 of substrate bracket 80.

A shown, analyzer A receives conditioned fluid from the mounted modular components M", said analyzer mounted to side panel 82.

Figure 32D:
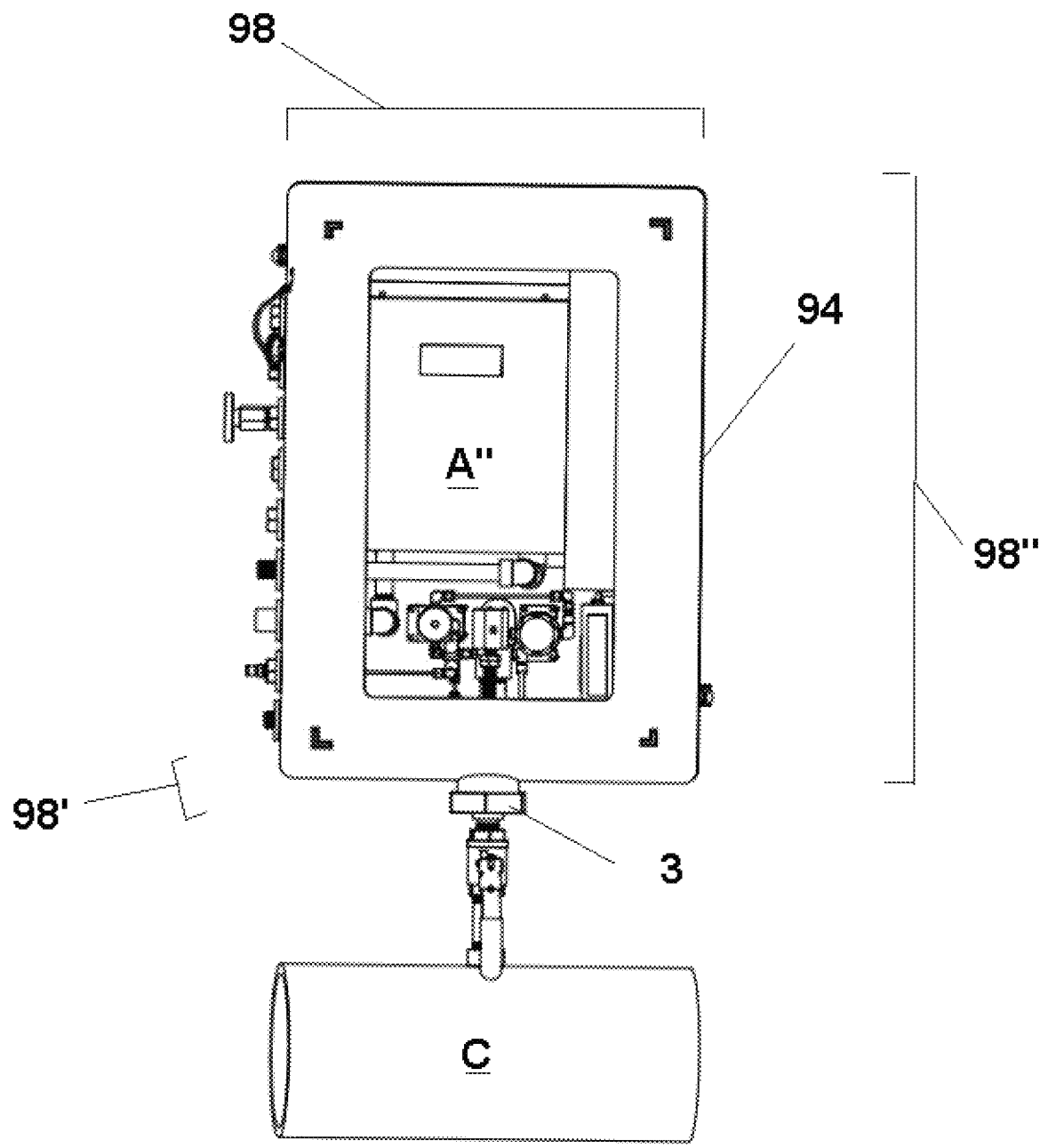
FIG. 32D is a side view of the invention of FIG. 32C, illustrating an appropriately sized and configured bifurcated housing of the invention of 8A-15 mounted thereto.

FIG. 32D is a side view of the invention of FIG. 32C, illustrating an appropriately sized and configured bifurcated housing of the invention of 8A-15 mounted thereto. As shown, the housing, like the earlier embodiment, comprises two pieces joined together in the matter taught in the invention of FIGS. 8A-15, the present embodiment of FIG. 32A-D having a length 98, depth 98' and height 98" formed to house, envelope and protect the substrate bracket 83 and anything mounted to the module mounting area 81, side mounting panel 82 and base 83, including components, analyzer(s) and other devices mounted thereto, while allowing select mounted modular components 78, 78' partial sealed exposure to the exterior to of the housing for exterior access.

It is further noted that not only components may be stored within the mounted enclosure and supported by bracket 81, but also other support items including, for example, calibration gas tanks or the like, or other components or analyzers which may be mounted to any available space on substrate bracket 80, including simply supported by or resting on the base 83. In addition, the substrate bracket 80 (as well as the earlier embodiment substrate bracket 6 of FIG. 5) or housings of the present application may be supported by vertical supports as required, depending on the load and environmental conditions.

Split Housing Utilizing Sub-Components

Figure 33:
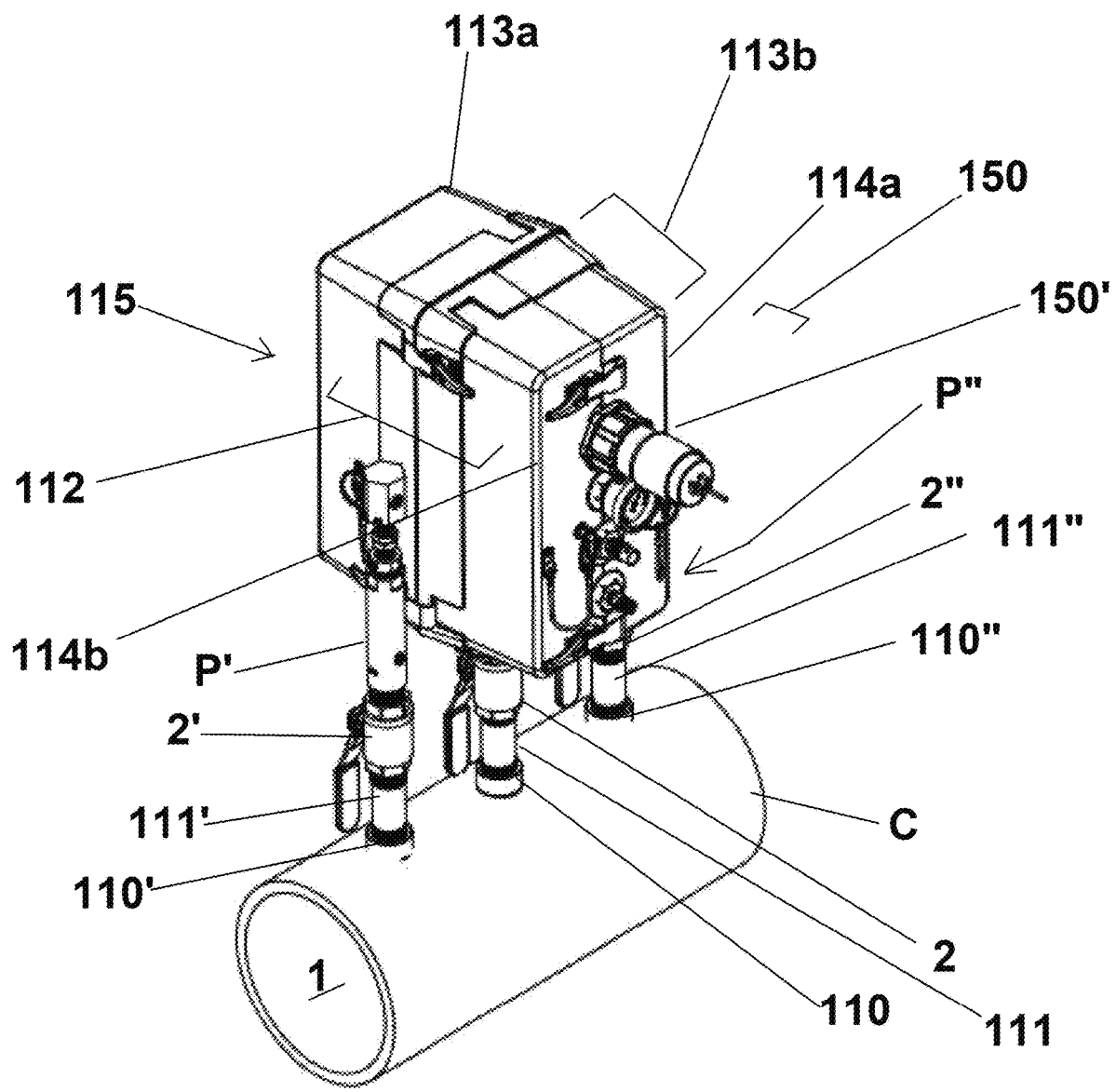
Figure 33A:
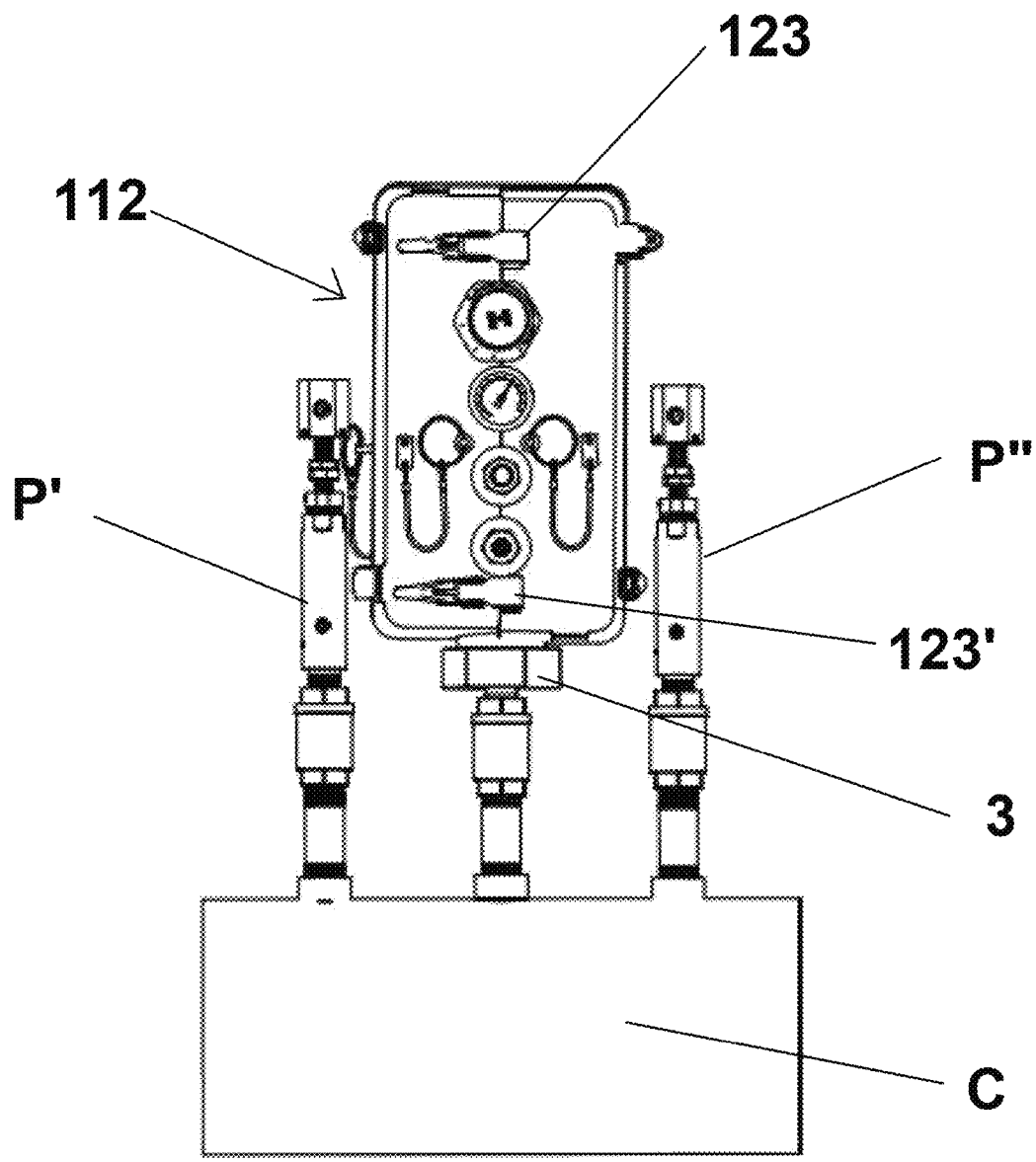
FIG. 33A is front view of the invention of FIG. 33.
Figure 34A:
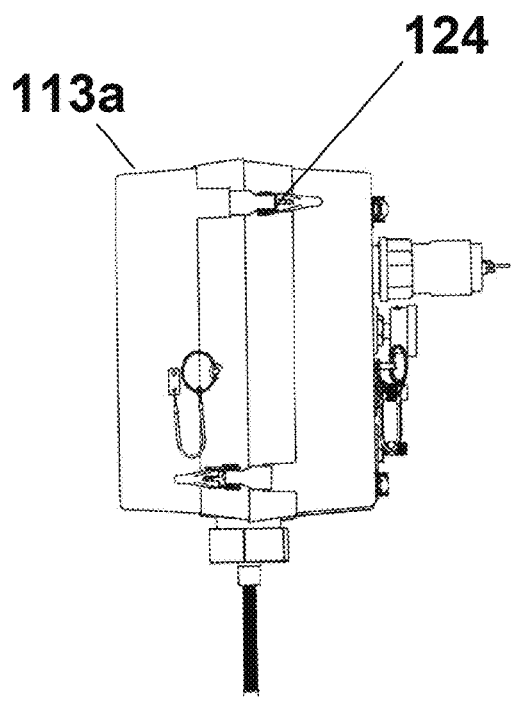
FIG. 34A is a left side view of the invention of FIG. 34.
Figure 34B:
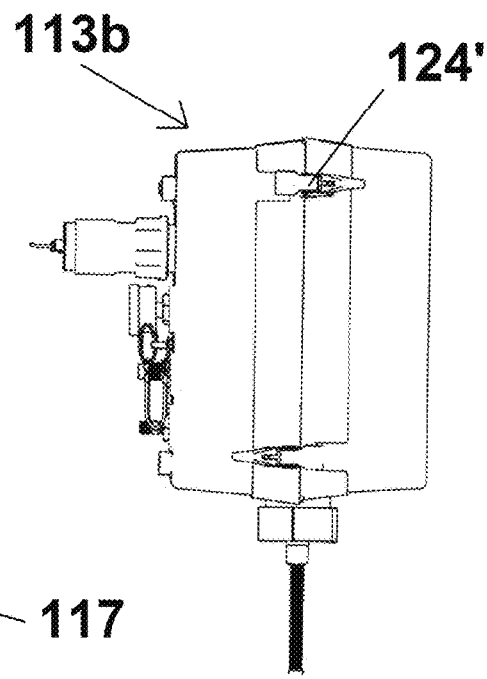
FIG. 34B is a right-side view of the invention of FIG. 34A.
Figure 34:
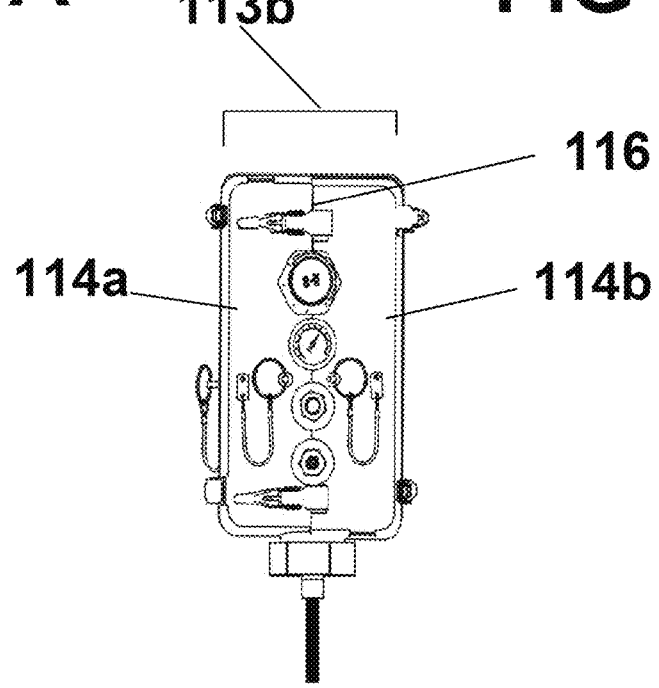
FIG. 34 is a front view of the invention of FIG. 33 A without the pipeline and thread-o-lets.
Figure 34C:
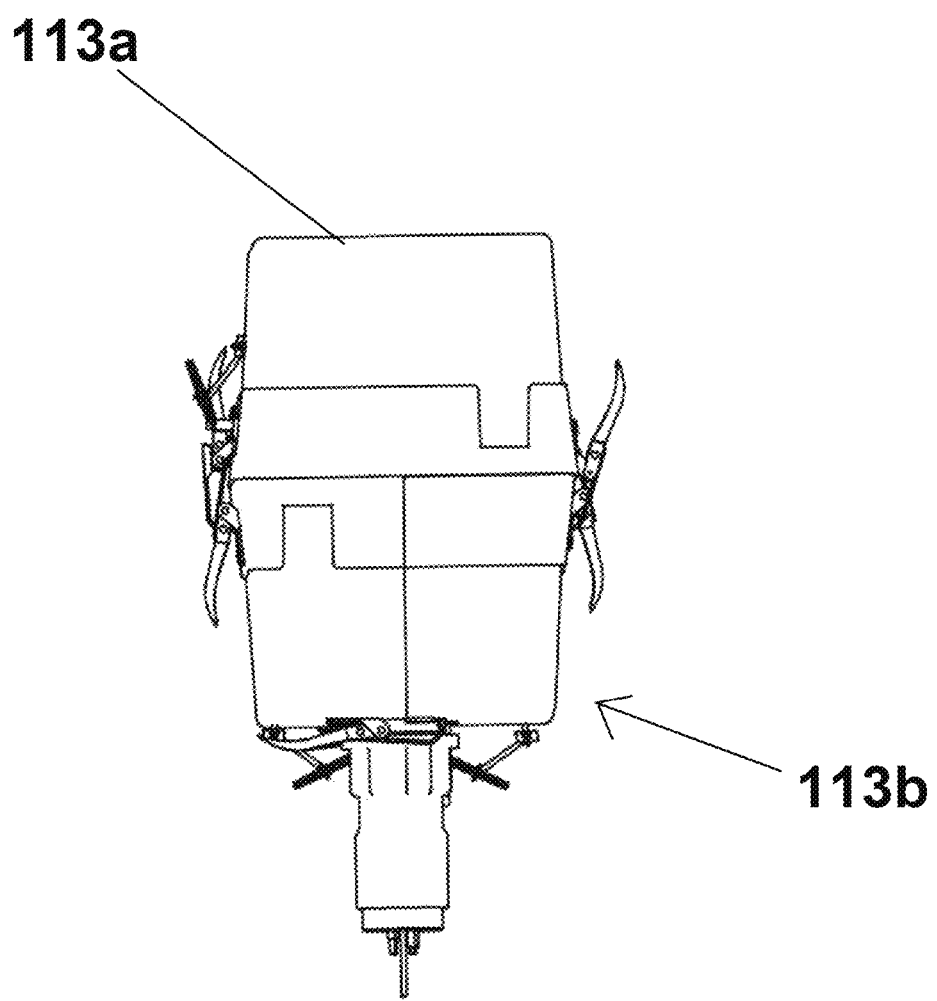
FIG. 34C is a top view of the invention of FIG. 34B.
Figure 35:
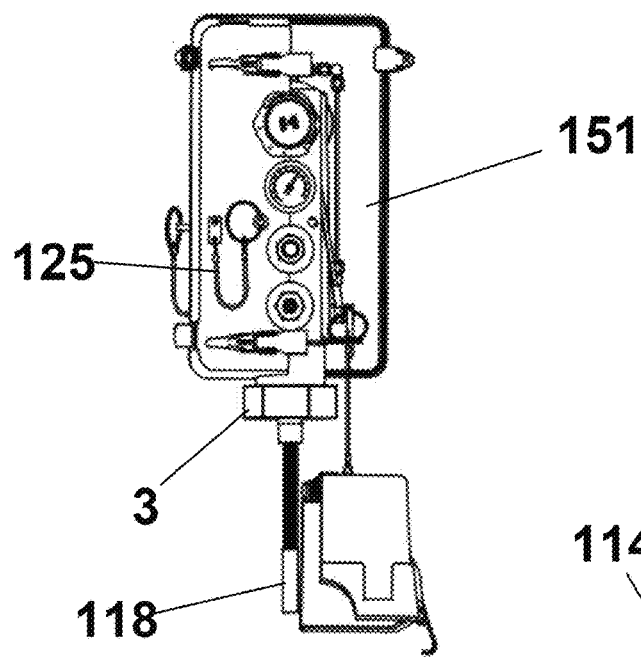
FIG. 35 is a front view of the invention of FIG. 34 shown with one of the two bifurcated, front enclosure sub-components removed for servicing the modular sample system enclosed therein.

FIGS. 33-35 E illustrate an alternative housing 112 when compared to the invention embodiments earlier detailed in this application, for example, in FIGS. 11A and 32D. Unlike the prior embodiments, the present embodiment provides a profile specifically configured for use in space constricted areas, such as between closely-spaced thread-o-lets 110', 110" (the thread-o-lets shown each engaging a nipple 111', 111" providing flow to a respective isolation valve 2', 2", with insertion probes P', P'" engaged thereto, respectively), so any housing situated therebetween would have to fit between any insertion probes emanating from adjacent installations, such as shown in the present figures.

The present system is illustrated as mounted between the two aforementioned insertion probes situated in the adjacent thread-o-lets. Those adjacent thread-o-lets may accommodate simply the insertion valves so as to provide access to the fluid stream when required, the insertion probes as shown, other devices insert or otherwise fluidly connected, or be simply plugged via plugs or the like.

As with the previous embodiments, the housing 112 of the present embodiment provides an enclosure for a modular conditioning system 115, which in the present exemplary embodiment is configured to receive and process fluid flow from a pressurized source 1 (such as a pipeline or conduit C) via an insertion probe P or the like, the probe in the present example having a tip 117 passing through a thread-o-let 110 (via insolation valve or the like) into the source. The thread-o-let illustrated in the present embodiment has threadingly mounted thereto a nipple 111 providing flow to isolation valve 2, which threadingly engages substrate coupling 3, the same coupling shown and described above in earlier embodiments of the invention (Such as FIGS. 2A-2C), and is formed to receive threadingly engage the insertion probe and provide passage for insertion of the probe tip leading to the pressurized source. Although the thread-o-lets in the present example discuss an exemplary configuration, it is noted they may be otherwise configured, depending on the circumstances of use.

Returning to the figures, substrate coupling 3 has mounted thereto, likewise similar to the earlier disclosed embodiments, a substrate bracket 6' fastened or otherwise affixed to the substrate bracket mounting area 27 of substrate coupling 3, via threaded fasteners or the like.

As with previous embodiments disclosed in the present application, the present embodiment utilizes first 113a and second 113b housing components (joined, for example, via latches 124, 124') to form an enclosure having modular component access apertures 120 to facilitate the passage of select modular conditioning components 119 at least partially therethrough or otherwise accessible from the exterior of the housing. As in the previous embodiments, the modular conditioning components 119 engage and are supported by substrate bracket 6' at a substrate bracket mounting area (via modular component mounting apertures 121) Likewise, the enclosure formed by joining the first and second housing components is configured to form a mounting aperture 122 at its base for encircling or be situated about the sidewall of substrate coupling 3 at or about substrate coupling housing engagement area 28 or the like.

Figure 35A:
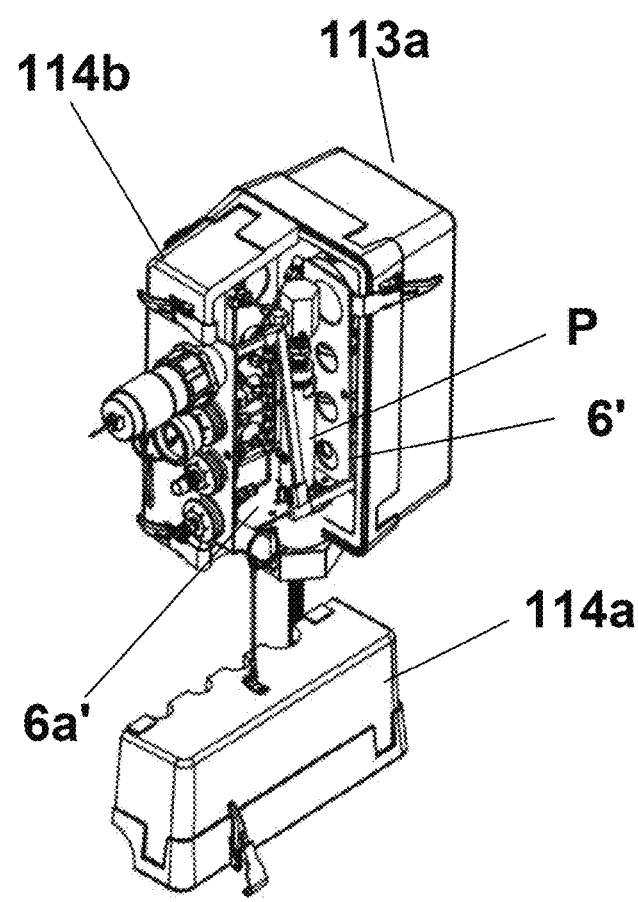
FIG. 35A is a perspective view of the invention of FIG. 35.
Figure 35B:
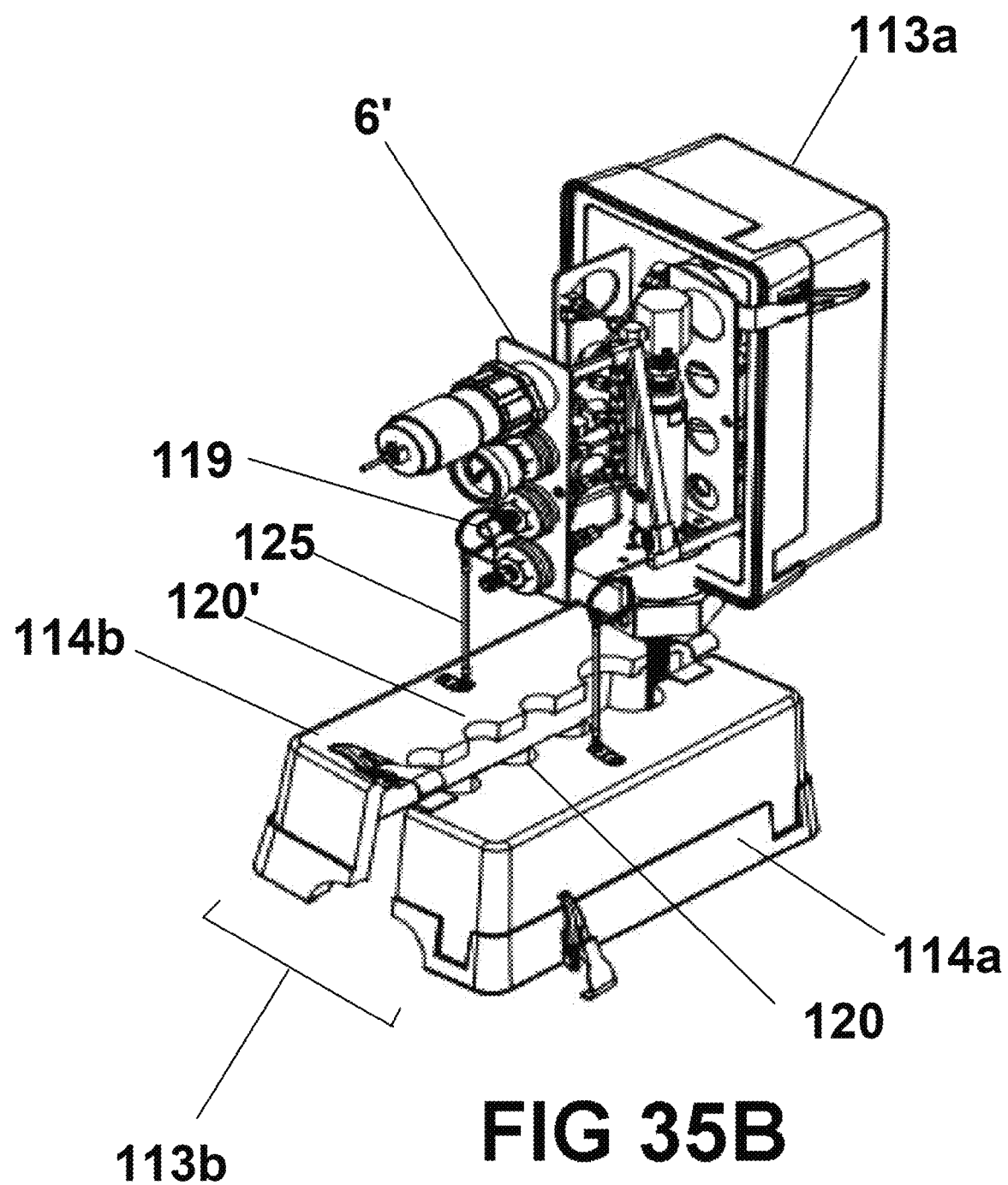
FIG. 35B is a perspective view of the invention of FIG. 35A, showing both first and second bifurcated, front enclosure sub-components removed to access the modular sample components and system enclosed therein.
Figure 35C:
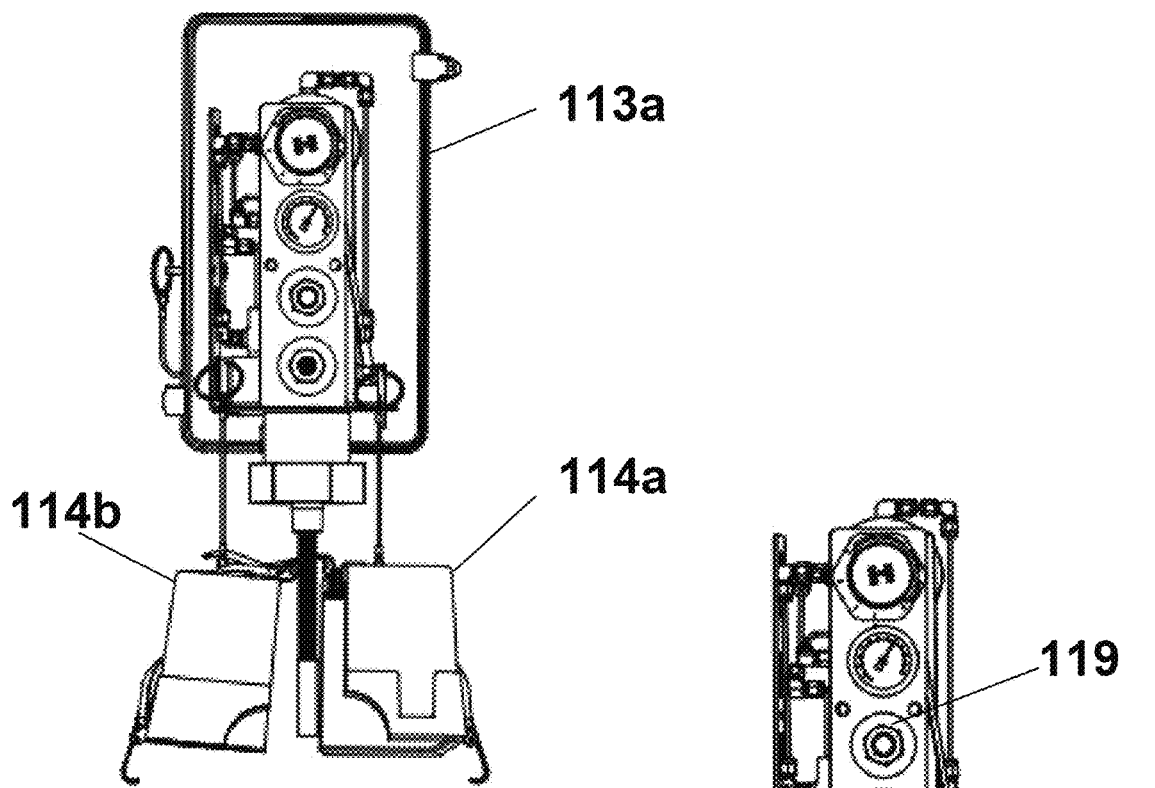
FIG. 35C is a front view of the invention of FIG. 35B.
Figure 35D:
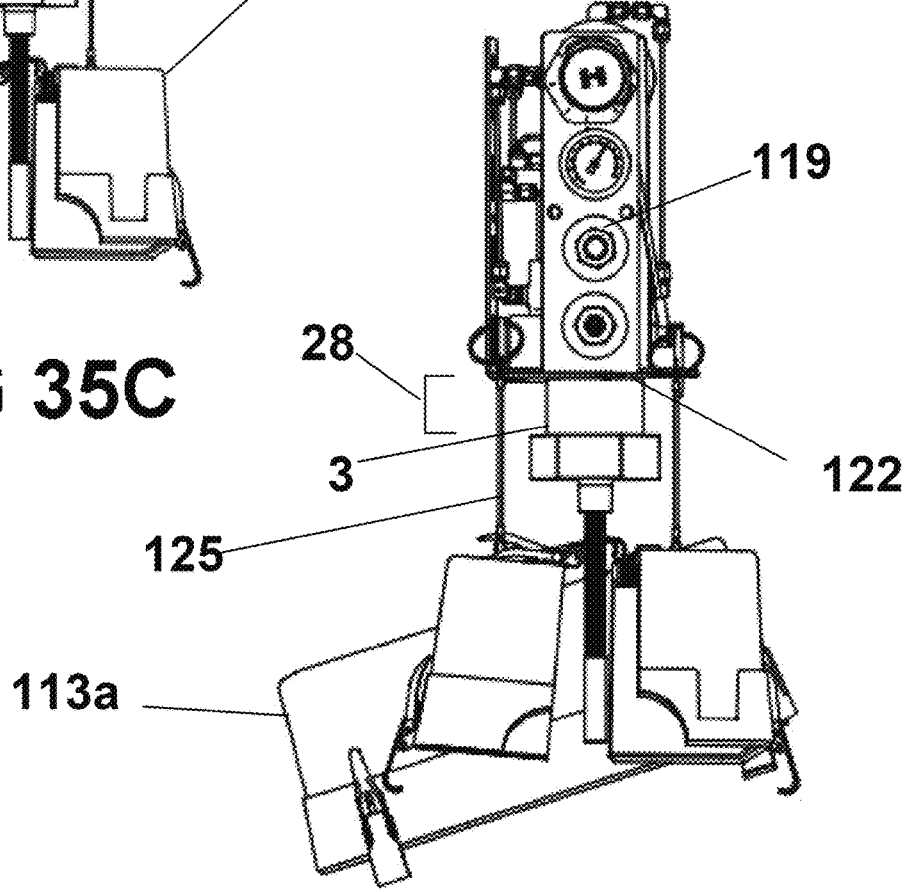
FIG. 35D is a front view of the invention of 35B, further illustrating the rearwardly situated enclosure component removed and suspended from the support bracket via cable, providing full access to the system enclosed therein.
Figure 35E:
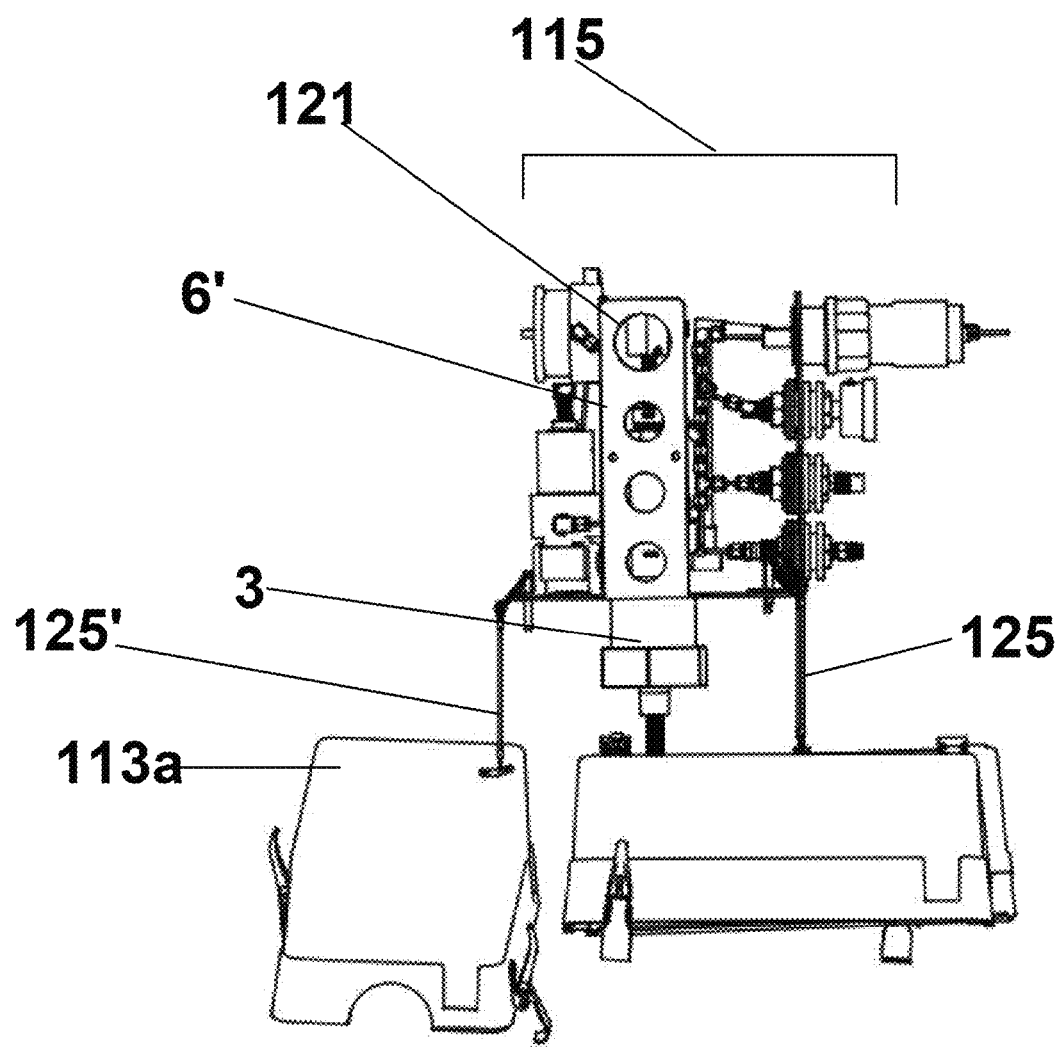
FIG. 35E is a left side view of the invention of FIG. 35D, further illustrating the rear and front situated enclosure components removed so as to provide full access to the system enclosed therein.
Figure 36:
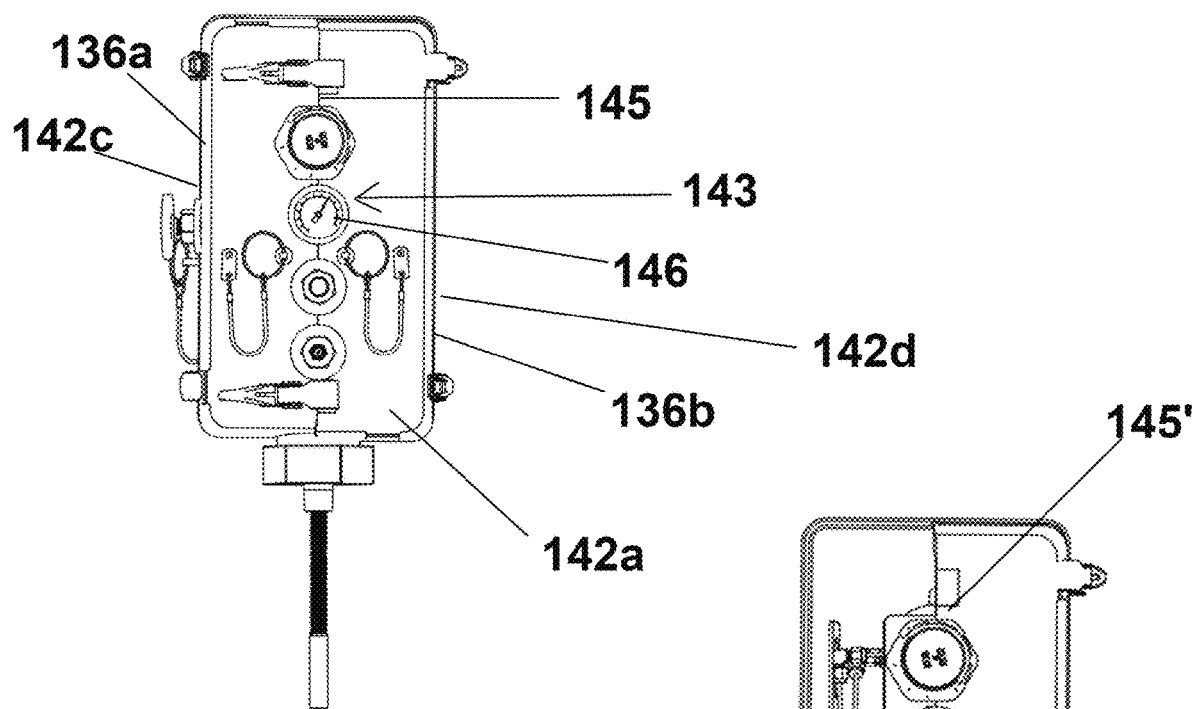
FIG. 36 is a frontal view of a variation of the invention of FIG. 33, wherein there is provided modular conditioning components or the like mounted to more than one module mounting areas provided on the substrate bracket, the present figure illustrating the bifurcated, front enclosure component having emanating therefrom modular components for access and viewing, and a modular component is seen emanating from the right side of the enclosure.
Figure 36A:
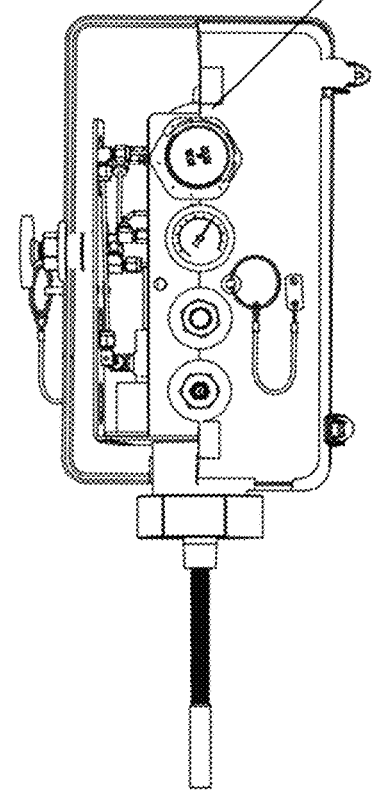
FIG. 36A is a frontal view of the invention of FIG. 33, wherein one (the left) of said two bifurcated, front enclosure sub-components are removed for access therein.

However, unlike the prior embodiments, wherein the first and second housing components each were illustrated as half the housing and joined to form the housing enclosure, in the present embodiment, the second housing component 113b is bifurcated or split 116 (shown split medially along its longitudinal axis 117) so as to provide separate first 114a and second 114b sub-components (one for each corner 150' forming the enclosure, as shown in FIGS. 35-35A) which are easily and releasably joined along their length, for example, via latches 123, 123' or the like, to form the second housing component 114a, and can be selectively removed in various configurations to provide various and diverse access options, as needed, and as illustrated in the aforementioned figures, providing access, for example to a quarter section 150 to provide partial access 151 to the desired modular sample components and system enclosed therein (e.g., FIGS. 35-35A showing front right quarter access to the interior provided by removal of housing sub-component 114a), or provide open access to half of the otherwise enclosed system (FIGS. 35B-35C) or full access of the entire modular conditioning system (e.g., all housing components removed as shown in FIGS. 35D-35E), the removed housing components or sub-components supported by cables 125, 125' or the like.

As shown in previous embodiments of the present invention (see, for example FIGS. 32A-32D and 35-35E, and the written description thereof), the substrate bracket may include more than one module mounting area emanating from the base of the substrate bracket, so as to provide flexibility in placement, configuration and size of the various modular components, instruments, boots/connections, other implements and the like provided in a modular sample conditioning system.

Housing Having Multi-Side Exterior Component Visibility/Access

The embodiment of the invention of FIGS. 36-42 illustrates still a further variation of the above disclosed embodiments, providing a substrate bracket 130 having emanating from its base 131 more than one module mounting area (each having modular component mounting apertures 144, 144', 144" formed therein) emanating from the base 131 of the substrate bracket. The base 131 of the present substrate bracket 130 is engaged to the substrate coupling 3 as described in the prior embodiments.

Referring to FIGS. 36-41, as in the previous embodiment, the housing 134 comprises first 134a and second 135b housing components, the second 135b housing component formed by first 136a and second 136b sub-components which are releasably retained to one-another via latches 142a, 142b, straps, snaps, or the like.

The housing 134 of the present embodiment as shown, when assembled, provides front, rear, and first and second sidewalls 142a-142d, respectively, which sidewalls can be formed from a single integrated portion of a housing component (as in the back wall 142b), or can comprise side formed by the joining of first and second housing components (as in side walls 142*c*-142*d*), or joined sub-components (such as front wall 142*a*).

The terms "front, rear, and side" as used in the present example are for discussion purposes only, and which said walls comprise "front, rear, and side", if any, can vary depending on placement, orientation, the operating environment, circumstances of use, design of the conditioning system, etc, and the use of said terms are not intended to be limiting.

With the installed housing/enclosure of FIGS. 33-35E, component mounting apertures (for example, 144, 144') in the respective module mounting areas 132, 132', 132" of substrate bracket 130 can be aligned with modular component access apertures 143, 143' formed in the housing component(s) (or visa-versa) so as to allow mounted modular components 146, to partially pass through or be otherwise accessible via said aligned access apertures, respectively, for access and/or visibility). Thus, the system of the present invention provides the unparalleled flexibility providing the ability to mount in various orientations components and other items associated with the modular conditioning system, providing the ability to easily and effectively position one or more components or the like via the substrate bracket mounting areas within the enclosure as well as to orient same to emanate or otherwise be accessible via apertures formed through one or more aligned sidewall(s) associated with the installed housing (which can include apertures formed along the edge(s) 145, 145' where the components or subcomponents are joined, respectively). Said component(s) or other items mounted to the substrate bracket can further be positioned to be accessible via removal of a chosen housing component or sub-component, which could be required for areas with limited space and/or access.

In addition, to facilitate a field installation of modular components in the system, preformed access apertures (preferably aligned with modular component mounting apertures in adjacent module mounting areas installed therein or installable, as required) can be provided with a plug or removable cover, or be formed with a weakened or frangible periphery in the enclosure wall(s) itself to allow one to "pop out" the weakened area with applied force to provide ready availability of an access/component pass-through aperture formed in the housing wall (or the edges of the housing component where the aperture is formed by joining the two edges) to receive or provide access to a component mounted to an underlying mounting area or backplate of a substrate bracket. Alternatively, indicia can be provided on the housing to indicate where access apertures can be formed in the housing, allow ready forming of an access aperture, such as via hole drill or the like, to facilitate installation as desired.

Alternatively, one or more module mounting areas 132" emanating from the base 131 of the substrate bracket 130 can be recessed 133 or otherwise positioned so that a mounted conditioning component 146" is fully situated within the mounted housing 134 or enclosure (i.e., not aligned with an access aperture in the housing and thus not accessible from outside of the enclosure).

FIGS. 36-40 illustrate a the present embodiment of the invention wherein there is provided modular conditioning components or the like mounted to more than one module mounting areas 132-132" provided on the substrate bracket, the present figures illustrating the bifurcated second housing component 135*b* formed of sub components 136*a*, 136*b* joined to form the front wall 142*a* of the present exemplary installation, the front wall 142*a* having emanating therefrom modular components 146 for access and viewing, and a modular component 145 is provided emanating from the right side of the enclosure. As with earlier embodiments, the module mounting areas effectively form a backplate to facilitate a barrier and support behind the exposed modular components, and, as discussed herein, can be used to engage, support and stabilize the enclosure halves forming the housing mounted thereabout. Further, as with earlier embodiments, a separate backplate can be mounted respective module mounting areas, for example, via mounting aperture formed therein, although separate backplates may not be required when the module mounting area 132" is situated in a recessed 133 position or otherwise fully enclosed relative to the housing.

Figures 37, 37A:
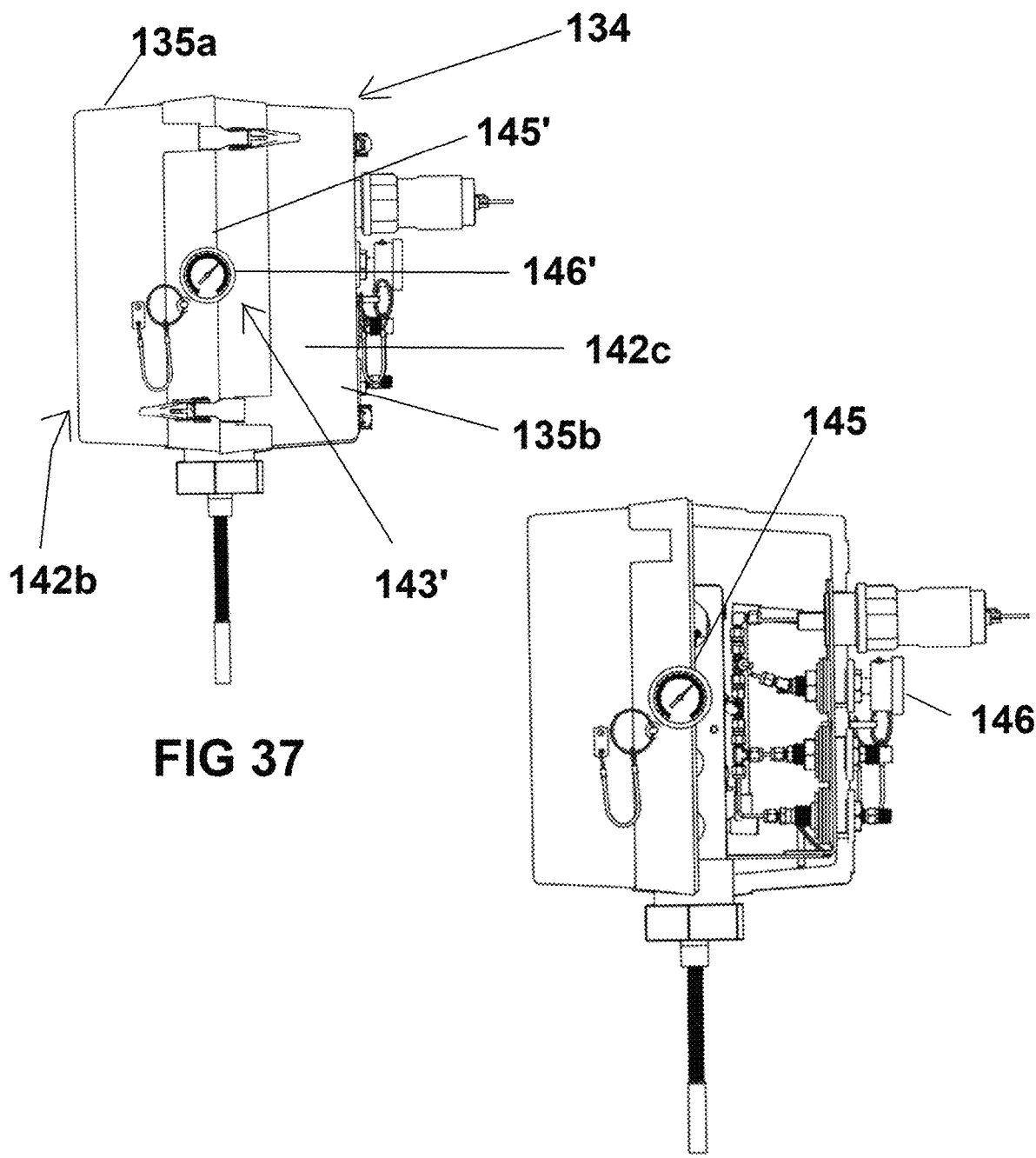
FIG. 37 is a right, side view of the invention of FIG. 36, illustrating a modular component emanating from said right side of the enclosure between the front and rear enclosure components, and supported by a second module mount emanating at a ninety degree angle from the first module mount, from the base of the substrate bracket.
FIG. 37A is the same view of the invention of FIG. 37, but with the left bifurcated front enclosure component is removed to provide access/viewing therein.
Figures 38, 38A:
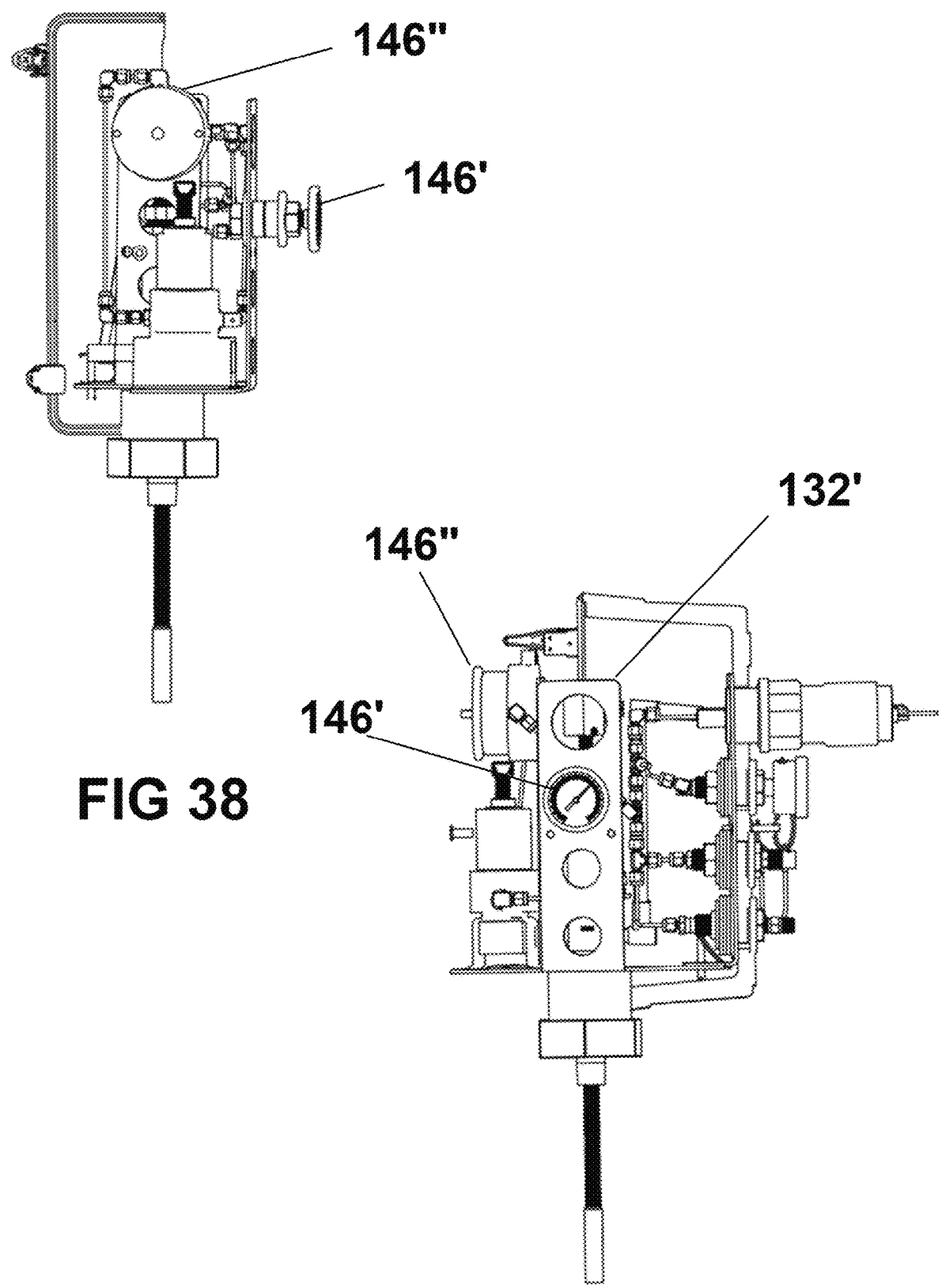
FIG. 38 is a rear view of the invention of FIG. 37A, with the rear enclosure component removed as well as the left bifurcated front enclosure component, to provide access, viewing therein, including viewing/access of modular conditioning components mounted therein including a heated regulator mounted to the substrate base.
FIG. 38A is a left side view of the invention of FIG. 38.
Figure 39:
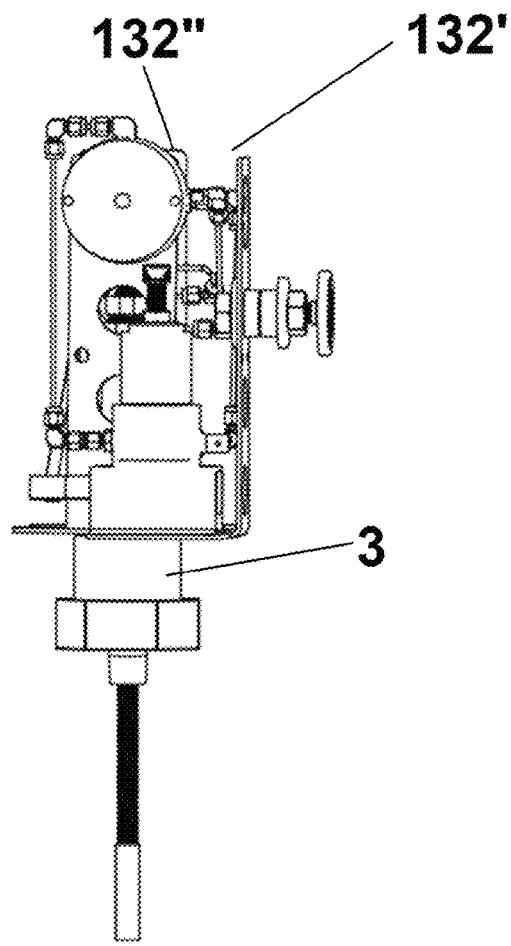
FIG. 39 is a rear view of the invention of FIG. 38, with both front and rear enclosure components removed.
Figure 39A:
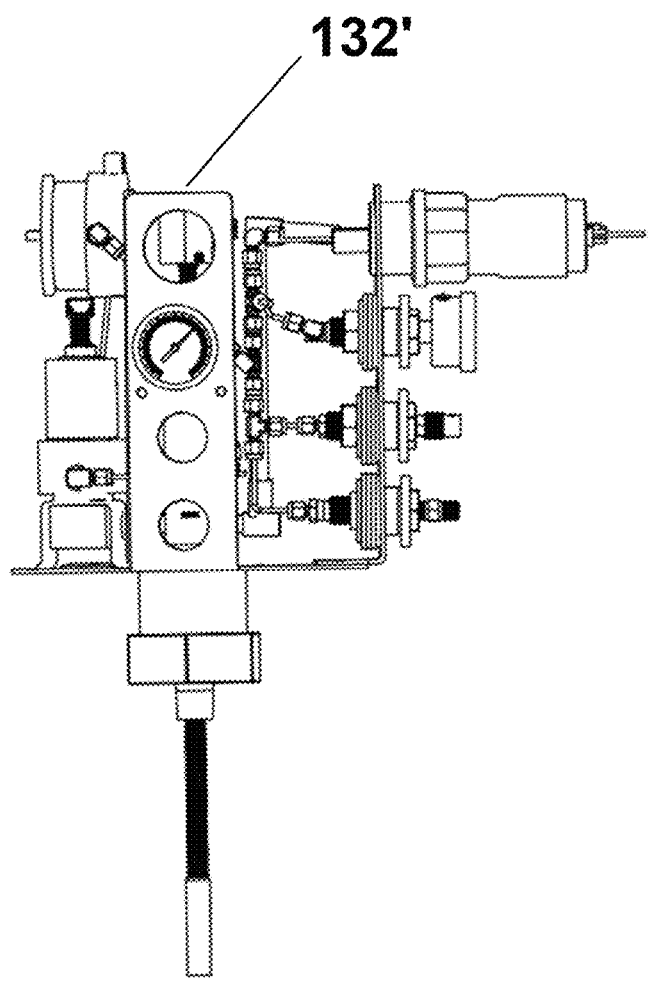
FIG. 39A is a left side view of the invention of FIG. 39.
Figure 40:
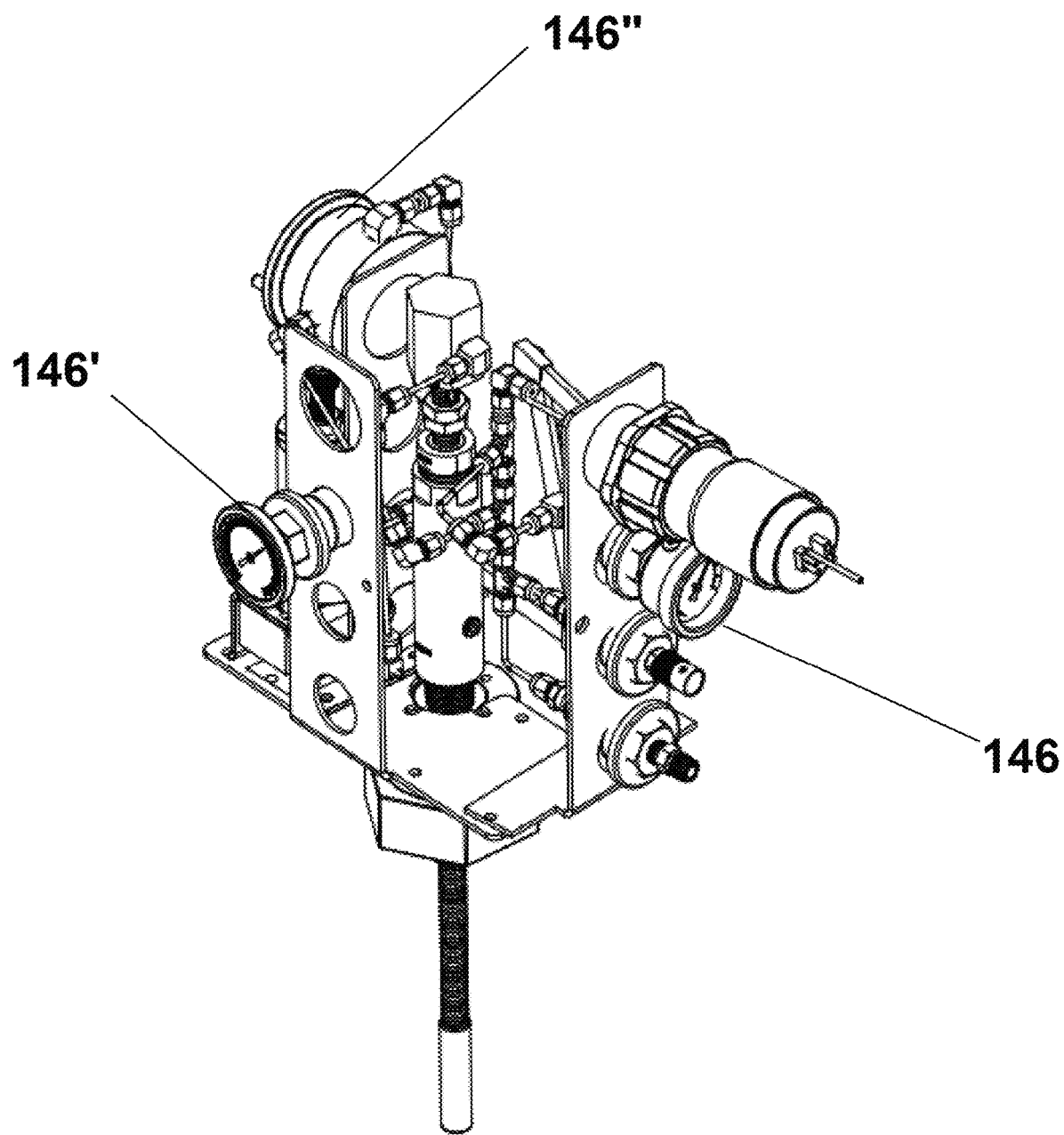
FIG. 40 is a perspective, view of the invention of FIG. 39A, showing the left and frontal areas of the system.
Figure 41:
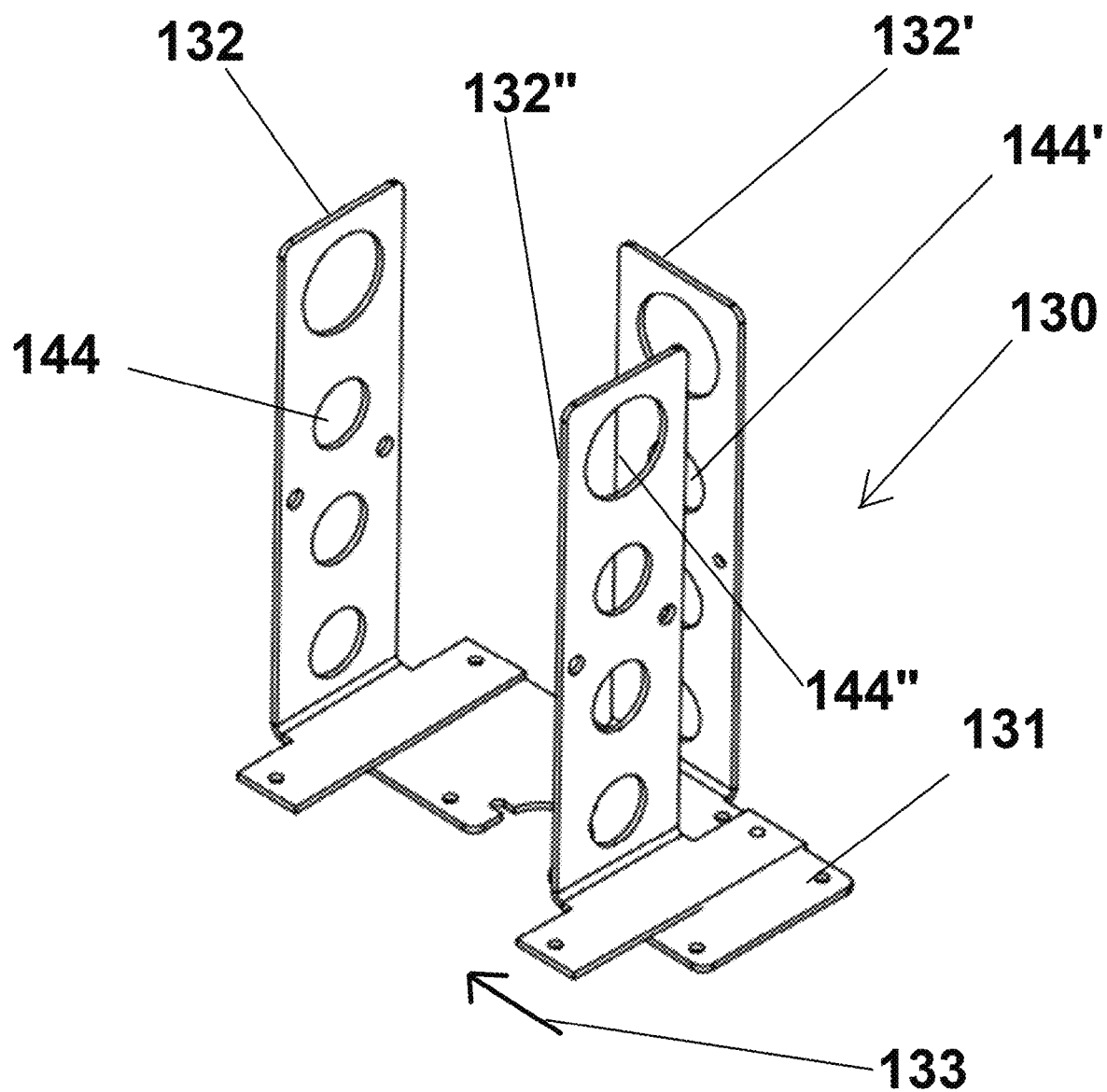
FIG. 41 is a perspective view of the substrate bracket utilized in the invention of FIG. 40, showing the rear and left sides of the bracket as installed in the present system.
Figure 41A:
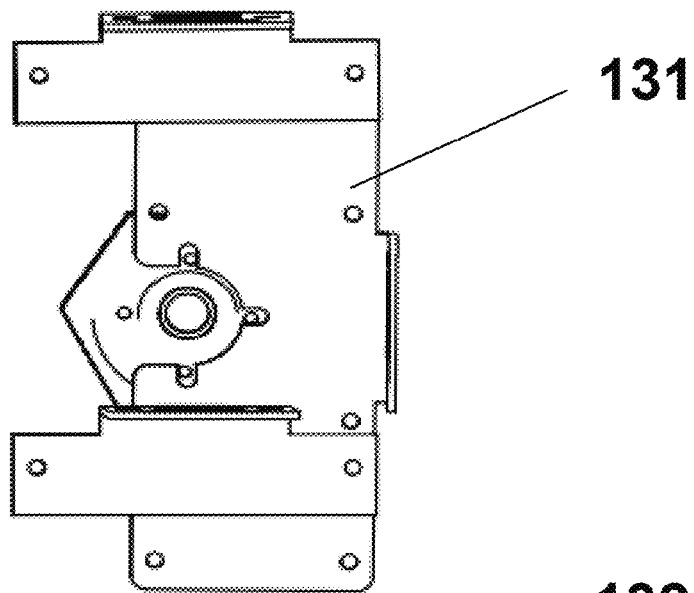
FIG. 41A is a top view of the bracket of FIG. 41, further illustrating the substrate coupling situated thereunder with fastener apertures aligned therewith for mounting.
Figure 41B:
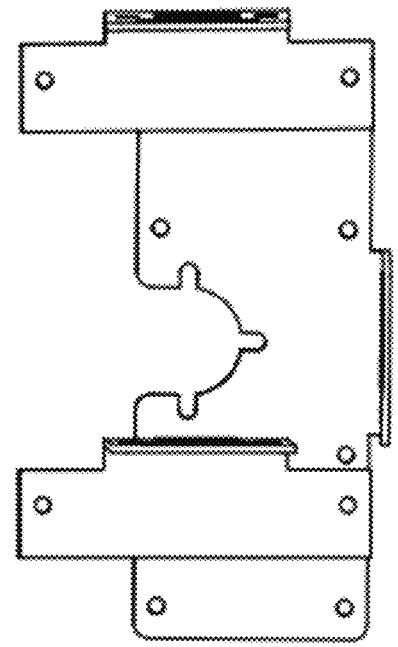
FIG. 41B is a top view of the substrate bracket only of the invention of FIG. 41A.
Figure 41C:
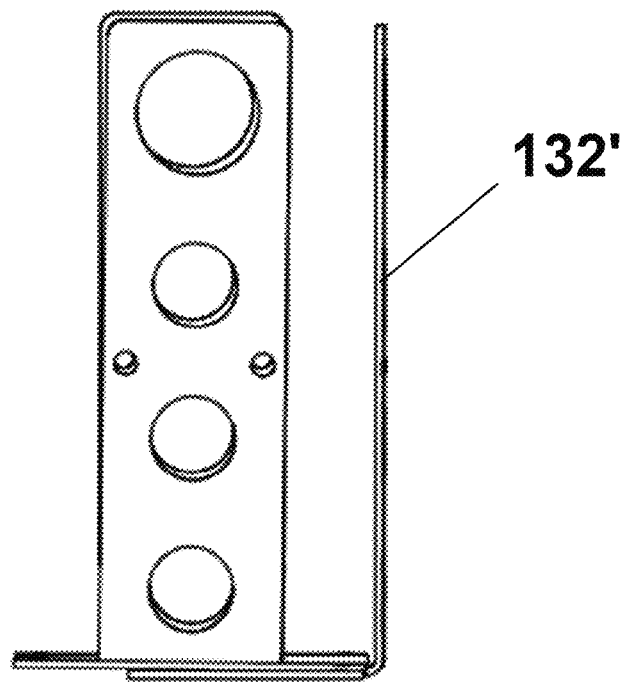
FIG. 41C is a side view of the substrate bracket of FIG. 41B.
Figure 42:
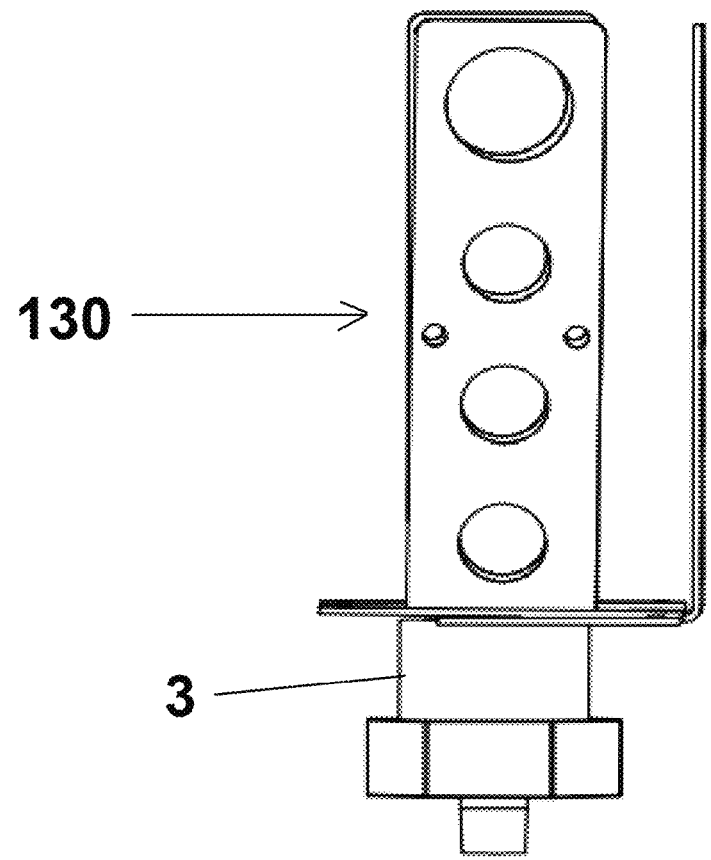
FIG. 42 is a side view of the invention of FIG. 41A.

As shown in the figures, the front enclosure sub-components are easily removeable to provide partial access to the system enclosed therein. As shown in FIGS. 37-38*a*, the first 135*a* enclosure component is easily removed to provide rear access (as applicable to the present exemplary installation, as well as the left side front enclosure subcomponent 136*a*, to provide access, viewing therein, including viewing/access of modular conditioning components mounted therein including a heated regulator mounted to the substrate base (see FIG. 38A).

Based upon the above and foregoing a modular conditioning system is provided comprising a substrate coupling engaging and providing passage to a conduit leading to a pressurized fluid source, said substrate coupling having mounted thereto a substrate bracket supporting one or more modular conditioning components, and first and second housing components formed to provide passage therethrough of a portion of one or more of said modular components so as to provide exterior access thereto.

Further, one of the methods of providing a modular sample conditioning utilizing the various embodiments of the present invention can be summarized as comprising, for example, the steps of:

a. providing a substrate coupling formed to engage a fluid passage, said substrate coupling formed to selectively facilitate the passage of an extraction device therethrough;

b. mounting said substrate coupling to a conduit containing a pressurized fluid;

c. mounting a substrate bracket to said substrate coupling, said substrate bracket having emanating therefrom a module mounting area having a length;

d. mounting one or more modular components along the length of said module mounting area;

e. providing fluid from said fluid extraction device to said modular components;

f. facilitating the passage of said fluid extraction device through said substrate coupling to engage the pressurized fluid;

g. facilitating the flow of fluid from said fluid extraction device to said modular components;

h. providing an enclosure to engage said substrate coupling to enclose same, forming a housing, while i. allowing portions of said modular components to pass through said housing, providing exterior portions of said modular components outside of said housing for visibility and/or access.

Still further, as earlier discussed, the housing enclosure components as designed can be used to directly or indirectly engage said modular components passing through said housing so as to support and secure said housing in place.

ELEMENTS

A, A' Analyzer
C Conduit

M Modular Components
E Elbow
R,' Regulator
T Tube
V Valve
P,'," Probe/probe assembly
1 pressurized source
2,',"  process isolation valve
3, 3', 3", 3a, 3b substrate coupling, base, tooling flat, threaded mounting apertures,
4, 4' extraction device (as probe), tooling flat
5,5' modular sample system, w/heat trace
6,', 6a,6a substrate bracket, base
7 temperature indicator
8 fittings
9 relief valve
10 pressure gauge
11 NPT connection
12 conduit junction box
13 block heater
14a,b enclosure halves
15 clasps
16 cables
17 pins
18, 18a gasket, gasket
19,a substrate coupling engagement slot
20, a,b enclosure base width, depth
21 enclosure length
22 base width, depth
23, a module mounting area, length
24, 24', 24a, 24b module component mounting apertures, access apertures
25 pass through
26 threaded Connector
27, 27' housing Mounting Area (on substrate coupling), cylindrical sidewall
28, 28', 28" substrate Coupling Housing Engagement area, width/diameter, base width/diameter
29 substrate coupling base extension
30, 30' mounting aperture for engaging substrate housing engagement area, width
31, 31', 31" substrate coupling first, second ends, length, diameter
32, 32', 32" substrate coupling socket, passage, threaded connection
33, 33' substrate coupling, threaded nipple
34, 34', 34" insertion assembly of extraction device 4, threaded end
35, 35' insertion retrieval, removal
36, 36' end, side of housing enclosure
37,' heat trace
38,' flexible insulated housing/enclosure
39,' top, bottom w/slit
40,',"  side wall, corners
41,' first, second edges
42, 42' fastener strip
43, 43', 43" fastener straps
44, 44', 44" space for passage of conditioning component therethrough
45 raised, upper edge
46,' top, open bottom
47,' components
48 GP2 Probe
49 threaded conduit passage
50 male threaded connection
51 substrate coupling (alternative)
52,' belts
53, 53' buckles
54 space
55,' edges
56,' top open bottom
57,',"  back, sidewalls
58,' front panels
59 upper
60 flange
61, 61' central passage flange, mounting surface threaded bore
62 threaded area of probe
63,',"  threaded passages
64,',"  spacers
65,' first, second ends
66,' flange ends
67.',"  fasteners/screws
68,',"  mounting surfaces
69 housing mounted
70 tightening
71,' housing outer, inner material
72 insulating layer
73 probe housing mounted to conduit C
74 insertion probe
75 probe housing
76,',"  first, second ends, passage
77 foot valve
78,' modular components
79 component
80 alternative substrate bracket
81 module mounting area
82 side mounting panel
83 base
84, ' length width
85 substrate coupling engagement slot
86,' module component mounting apertures
87,',"  modular components
88,', height, width
93 analyzer
94 housing
95 probe
96 flowing
97,' base width, depth
98,',"  housing length, depth, height
99,',"  heat trace, length, end
100,' retaining straps
101 affixed
102 inner wall of housing
110,',"  fitting ports (threadolets)
111,',"  nipple
112 housing
113a, b first, second housing components
114a, b housing sub-components
115 modular conditioning system
116 split
117 longitudinal axis
118 probe tip
119, 119' modular conditioning components
120, 120' modular component access apertures
121, 121' modular component mounting apertures
122 mounting aperture for engaging substrate housing engagement area
123,' sub-component latches
124, ' housing component latches
125,' cable
130 substrate bracket
131 base
132, ', " module mounting areas 133 recessed
134 housing
135a, b first, second housing components
136a, b housing sub components
138 joined edges
139 gaskets
140 components
141 regulator
142a, b, c, d housing side walls
143,','' modular component access apertures
144,','' modular component mounting apertures
145,' edges where the components/subcomponents are joined
146, ',''  mounted modular components
150,' quarter section, corner,
151 quarter access
160 engaging
161 backplate
162 mounting apertures The embodiments listed are not intended to be an exhaustive list of applications, but only intended to show the need and some of the practical applications of the invention. Further, the invention embodiments herein described are done so in detail for exemplary purposes only and may be subject to many different variations in design, structure, application and operation methodology. Thus, the detailed disclosures therein should be interpreted in an illustrative, exemplary manner, and not in a limited sense.

I claim:

1. The method of housing a sample conditioning system, comprising the steps of:
   a. providing a substrate coupling having a passage formed therethrough to receive a fluid extraction device, said substrate coupling having a first and second ends;
   b. mounting said first end of said substrate coupling so that said passage of said substrate coupling leads a conduit containing a pressurized fluid;
   c. mounting a substrate bracket to said second end of said substrate coupling, said substrate bracket having a module mounting area;
   d. mounting one or more modular components along said module mounting area of said substrate bracket;
   e. providing between one or more of said mounted modular components fluid communication pursuant to a desired flow path, providing mounted modular components;
   f. providing first and second enclosure components configured to engage one another to provide a housing, said housing having one or more module component access apertures, and a mounting aperture formed to engage said substrate coupling;
   g. mounting and securing said housing, comprising the steps of positioning said first and second enclosure components about said substrate coupling and substrate bracket, and assembling said first and second enclosure components so as to form said housing, so that said mounting aperture of said housing is situated around said sidewall of said substrate coupling, and said substrate coupling mounting area is enclosed by said housing; while
   h. aligning one or more of said module component access apertures formed in said housing with one or more of said mounted modular components so as to provide exterior access or visibility to said one or more of said mounted modular components, from outside of said housing.

2. The method of claim 1, wherein in step "g" said step of assembling said first and second enclosure components comprises; utilizing said one or more of said module component access apertures formed in said housing to engage said one or more of said mounted modular components, so as to support and retain said housing in place.

3. The method of claim 2, wherein in step "e" said housing is formed of insulated material, comprising a top, a sidewall joined along its upper edge with a top, said sidewall forming first and second panels having first and second edges, respectively, said first and second edges having a space therebetween defining said one or more openings to facilitate the passage therebetween of said one or more mounted modular components.

4. The method of claim 3, wherein in step "g", fasteners are used to engage said first and second edges of said first and second panels about said one or more mounted modular components.

5. The method of claim 4, wherein said fasteners comprise straps used to draw said first and second edges of said first and second panels together and block any space therebetween.

6. The method of claim 1, wherein in step "d" said modular components comprise modular sample components, and wherein there is an added step "i" of facilitating the flow of fluid from said modular sample components to an analyzer.

7. The method of claim 6, wherein said modular sample components comprise modular sample conditioning components, and wherein in step "i" there is added the sub-step "i(a)" of using said modular sample conditioning components to condition said pressurized fluid, providing conditioned sample fluid, and directing said conditioned sample fluid to said analyzer.

8. The method of claim 6, wherein in step "e" there is provided the added step of mounting said analyzer to said substrate bracket, and in step "g" said housing is secured so as to enclose said analyzer along with said mounted modular components, while providing exterior access to a portion of said one or more modular components.

9. The method of claim 1, wherein in step "e" said housing comprises first and second enclosure components and there is further included the step of providing a gasket along said one or more said module component access apertures formed in said housing, and step "h" includes the step of utilizing said gasket to facilitate engagement of said housing to one or more said mounted modular components.

10. The method of claim 9, wherein in step "c" said substrate bracket has the module component mounting apertures formed in said module mounting area to receive said modular components, and said module component access apertures formed in said enclosure components are positioned to facilitate alignment with openings formed in said housing when said housing is mounted in steps "g" and "h".

11. The method of claim 10, wherein there is an added step "i" of utilizing said exterior access to monitor and control the flow of fluid to said modular components.

12. The method of claim 11, wherein in step "d" the step of providing a fluid extraction device having a length, and engaging said substrate coupling by positioning a portion of said length through said substrate coupling passage, providing a mounted extraction device, and there is further added a step "j" of removing at least one of said enclosure components to provide access to said mounted extraction device.

13. The method of claim 12, wherein said fluid extraction device is a sample probe.

14. The method of claim 1, wherein one of said first or second enclosure components comprise first and second sub-components, each said first and second sub-components comprising a first and second corners of said housing when assembled.

15. The method of claim 14, wherein in step "f" said housing has sides, and wherein in step "c" said substrate bracket comprises first and second module mounting areas comprising one or more component mounting apertures, and in step "h", each said first and second module mounting areas are aligned with a different side of said housing.

16. The method of claim 15, wherein in step "c" said module component access apertures are formed in more than one side of said housing so that each module component access aperture is in alignment with a respective component mounting aperture formed in said first and second mounting areas.

17. A modular sampling system for retrieving a sample from a pressurized fluid source, comprising:
    a substrate coupling having first and second ends, said substrate supported by a conduit containing a pressurized fluid, said substrate coupling formed to allow passage of an extraction device therethrough to engage said pressurized fluid;
    a mounting bracket having a base engaging said second end of said substrate coupling, said mounting bracket having emanating therefrom a module mounting area having a length;
    one or more modular components mounted along said module mounting area of said mounting bracket so as to provide mounted modular components, at least two of said mounted modular components having fluid communication therebetween pursuant to a desired flow path, said modular components formed to receive fluid from said extraction device;
    a housing having one or more component passages for receiving portions of one or more of said modular components therethrough, so as to facilitate exterior access and/or monitoring of said one or more modular components outside of said housing;
    whereby, upon positioning said housing about said modular components and said mounting bracket, positioning said one or more component passages formed in said housing about a portion of at least one or more of said mounted modular components so as to engage said housing therewith via said component passages, providing exterior access to portions of said mounted modular components, while retaining said housing in place.

18. The apparatus of claim 17, wherein said modular components comprise modular sample components configured to condition pressurized fluid from said extraction device, providing conditioned fluid.

19. The apparatus of claim 18, wherein said extraction device comprises an insertion probe inserted into said substrate coupling conduit, said insertion probe having a tip positioned to receive fluid from said pressurized fluid source.

20. The apparatus claim 18, wherein said housing comprises first and second enclosure components formed to enclose said module mounting area of said substrate bracket, forming a housing, while allowing the passage of portions of said mounted modular components for access exterior said housing.

21. The apparatus of claim 20, wherein said module mounting area of said mounting bracket has module component mounting apertures formed to receive said modular components, and said enclosure components are formed to engage along their length to form said housing, said housing having module component access apertures aligned with said module component mounting apertures of said module mounting area upon mounting, so as to allow the passage of portions of said mounted modular components through said housing, while providing exterior thereto.

22. The apparatus of claim 21, wherein said housing comprises first and second enclosure components, wherein one of said first or second enclosure components comprise first and second sub-components, each said first and second sub-components comprising a first and second corners of said housing when assembled.

23. The method of claim 22, wherein said housing has sides, and wherein said substrate bracket comprises first and second module mounting areas comprising one or more component mounting apertures, whereby, upon assembling said first and second enclosure components to assemble said housing about said modular components and said mounting bracket while positioning said one or more component passages formed in said housing side walls to engage at least one or more of said mounted modular components via said component passages, there is provided exterior access to portions of said mounted modular components with said first and second module mounting areas aligned with a different side of said housing, while retaining said housing in place.

24. The apparatus of claim 22, wherein said enclosure components are formed to engage one another while interfacing with said mounted modular components and substrate coupling so as to provide a structural integration therebetween, said integration enhancing stability, while increasing rigidity of the system and retaining said housing in place.

25. The apparatus of claim 21, wherein said housing comprises first and second enclosure components formed to enclose said module mounting area of said substrate bracket, forming a housing, while allowing the passage of portions of said mounted modular components for access exterior said housing.

26. The apparatus of claim 18, wherein said housing is formed to allow the passage of said extraction device through said substrate coupling without the need to remove said mounting bracket or said substrate coupling, as well as allow said enclosure component to be removed independently without hinges.

27. The apparatus of claim 18, wherein said housing is formed a of flexible and/or insulating material, said housing having an open bottom.

28. The apparatus of claim 27, wherein said substrate bracket has a base having a length and width, and wherein said open bottom of said housing has a length and width formed to envelope said base, so as to close said open bottom.

29. The apparatus of claim 28, wherein said housing comprises side, front and back panels, and a top panel forming a cover, the front panel having being longitudinally separated to form first and second edges.

30. The apparatus of claim 29, where said space between said first and second edges forms said one or more component passages.

31. The apparatus of claim 30, wherein said first and second edges have first and second fastener strips, respectively, to engage and tighten said first and second edges about said one or more modular components.

32. A modular sampling system for retrieving a sample from a pressurized gas source, comprising:
    a substrate coupling comprising:

a flange having first and second ends and a bore therethrough, said bore formed to provide passage for a probe to a conduit containing a pressurized gas;

at least first and second spacers having first and second ends, said first end of said spacers affixed to said first end of said flange, said second end of said spacers forming a mounting surface;

a substrate bracket mounted to said mounting surface of said spacers, said substrate bracket formed to engage and support modular components formed to receive pressurized fluid from said probe in a predefined flow pattern, providing conditioned fluid;

a housing formed to enclose said substrate bracket, said housing having space formed therein to receive one or more of said modular components so as to allow provide in one or more of said modular components at least partial exterior access and/or visibility, so as to provide protruded modular components;

whereby said housing houses said modular sample system and is retained in place and supported by said protruded modular components.

33. The apparatus of claim 32, wherein said housing comprises first and second enclosure components, wherein one of said first or second enclosure components comprise first and second sub-components, each said first and second sub-components comprising a first and second corners of said housing when assembled.

34. The method of claim 33, wherein said housing has sides, and wherein said substrate bracket comprises a first and second module mounting area comprising one or more component mounting apertures, whereby, upon assembling said first and second enclosure components to assemble said housing about said modular components and said mounting bracket while positioning said one or more component passages formed in said housing side walls to engage at least one or more of said mounted modular components via said component passages, there is provided exterior access to portions of said mounted modular components with said first and second module mounting areas aligned with a different side of said housing, while retaining said housing in place.

35. A method providing a sample conditioning system, comprising the steps of:
 a. providing a substrate coupling formed to engage a fluid passage, said substrate coupling having a passage formed to receive a fluid extraction device;
 b. mounting said substrate coupling to a conduit containing a pressurized fluid;
 c. mounting a substrate bracket to said substrate coupling, said substrate bracket having emanating therefrom a module mounting area;
 d. mounting one or more modular components along the length of said module mounting area, providing mounted modular components;
 e. facilitating the passage of said fluid extraction device through said substrate coupling to engage the pressurized fluid;
 f. facilitating the flow of fluid from said fluid extraction device to said modular components;
 g. providing a housing having one or more component passages for receiving portions of one or more of said modular components therethrough, so as to facilitate exterior access and/or monitoring of said one or more modular components outside of said housing; and
 h. positioning said housing about said modular components and said substrate bracket, positioning said one or more component passages formed in said housing about a portion of at least one or more of said mounted modular components so as to engage said housing therewith via said component passages, providing exterior access to portions of said mounted modular components, while retaining said housing in place.

36. A method of housing a modular sample system, comprising the steps of:
 a. providing a substrate coupling formed to engage a fluid passage, said substrate coupling having an axial bore formed therethrough to facilitate the positioning of a fluid extraction device therethrough;
 b. mounting said substrate coupling to a conduit containing a pressurized fluid;
 c. mounting a bracket to said substrate coupling, said bracket having emanating therefrom a module mounting area having a length;
 d. mounting one or more components to said module mounting area of said bracket;
 e. positioning a fluid extraction device through said substrate coupling to engage said pressurized fluid;
 f. facilitating the flow of said pressurized fluid through said fluid extraction device to one or more of said components;
 g. positioning an enclosure to engage said substrate coupling, forming a housing about said modular sample system, while
 h. providing one or more openings in said housing to facilitate access and/or visibility of at least a portion of one or more of said components, providing exposed components; while
 i. utilizing said module mounting area of said bracket to stabilize and support said enclosure forming said housing.

37. The method of claim 36, wherein following step "h" there is provided the added step "step "h1" of positioning said one or more openings in said enclosure so to facilitate the visibility and/or access to said one or more components exterior said housing.

38. The method of claim 37, wherein following sub-step "h1", there is provide the added sub-step "h2" of utilizing said portions of components passing through said openings to stabilize and support said housing about said modular sample system.

39. The method of claim 36, wherein in step "i" there if is further provided the step "i1" of utilizing said module mounting area to form a backplate to provide a barrier behind said exposed components, and "i2" allowing said backplate to engage said enclosure forming said housing to as to stabilize and support same.

40. The method of claim 36, wherein in step "i" there if is further provided the step "i1" of providing a backplate associated with said module mounting area of said substrate bracket, said backplate formed to provide a barrier behind the exposed components, and "i2" allowing said backplate to engage said enclosure forming said housing to as to stabilize and support same.

41. The method of housing a modular sample system, comprising the steps of:
 a. providing a substrate coupling having a passage formed therethrough to receive a fluid extraction device, said substrate coupling having a first and second end;
 b. mounting said substrate coupling so that said passage of said substrate coupling engages a conduit containing a pressurized fluid;
 c. mounting a base of a substrate bracket to said substrate coupling, said substrate bracket having a first module mounting area;

d. mounting one or more modular components along said first mounting area of said substrate bracket, providing mounted modular components;

e. providing a housing having one or more openings;

f. positioning said housing to engage said first module mounting area so that said component opening(s) provide exterior access or visibility to at least a portion of one or more of said mounted modular components; while g. utilizing engagement of said housing to said first module mounting area to support and secure said housing in place, with said housing enclosing said base of said substrate bracket, at least a portion of one or more of said modular components, and at least a portion of said substrate coupling.

42. The method of claim 41, wherein in step "d" one or more of said modular components comprise modular sample components, and wherein there is provided the added step "h" of facilitating the flow of fluid from one or more of said modular sample components to an analyzer.

43. The method of claim 42, wherein in step "h" there provided the sub-step "h1" of conditioning said fluid as it flows through said one or more modular sample components to provide conditioned sample fluid, as well as the added sub-step "h2" of flowing said conditioned sample fluid to said analyzer.

44. The method of claim 43, wherein in step "d" there is provided the added step "d1" of mounting said analyzer to said substrate bracket, and in step "g" said housing is secured so as to house said analyzer along with said mounted modular components, while providing exterior access or visibility to a portion of said one or more modular components.

45. The method of claim 41, wherein in step "e" said housing comprises first and second enclosure components, and wherein there is further included the added sub-step "e1" of providing a gasket along said one or more said component openings formed in said housing, and wherein in step "g" there is included the added sub-step "g1" of utilizing said gasket to facilitate engagement of said first and second enclosure components forming said housing to one or more said mounted modular components.

46. A sampling system for retrieving a sample from a pressurized fluid source, comprising:

a substrate coupling having a first and second ends, said first end of said substrate coupling mounted to and engaging a conduit providing passage to a pressurized fluid, said substrate coupling formed to allow the passage of an extraction device therethrough to receive flow from said pressurized fluid;

a mounting bracket having a base engaging said second end of said substrate coupling, said mounting bracket further comprising a first mounting area having a length situated at a right angle relative to said base;

one or more components mounted along said first mounting area of said mounting bracket, wherein one or more of said mounted components are formed to receive fluid from said extraction device;

a housing having one or more openings formed to facilitate exterior access and/or monitoring of one or more of said components;

whereby, upon mounting said housing to said sampling system to form an enclosure enveloping at least a portion of said substrate coupling and at least a portion of one or more of said components, said first mounting area of said mounting bracket provides support to retain said housing in place, while providing exterior access and/or visibility to said one or more components.

47. The apparatus of claim 46, wherein one or more of said components are configured to condition pressurized fluid from said extraction device to provide conditioned fluid.

48. The apparatus of claim 46, wherein said extraction device comprises a sample probe.

49. The apparatus of claim 46, wherein said extraction device comprises an insertion probe.

50. The apparatus claim 46, wherein said housing comprises at least first and second enclosure components formed to enclose said mounting bracket, and at least a portion of said substrate coupling and said components.

51. The apparatus of claim 50, wherein said first mounting area of said mounting bracket has component mounting apertures formed along its length to receive said components, and said enclosure components are formed to engage along their length to form said housing, said housing having formed therethrough one or more component access apertures aligned with said component mounting apertures of said first mounting area, so as to provide exterior access to said components with said housing situated thereupon.

52. The apparatus of claim 51, wherein one or more of said mounted components are positioned relative to said housing to facilitate exterior access thereto as well as facilitate the conditioning of fluid flowing therethrough, and wherein one or more of said protruded modular components further formed to engage said housing to support and retain said housing in place.

53. The apparatus of claim 46, wherein there is further provided a second mounting area having a length emanating from and orthogonally oriented relative to said base, said second mounting area orthogonally oriented relative to said first mounting area, said second mounting area having an analyzer mounted thereto, said analyzer formed to receive fluid flow from one or more of said mounted components.

* * * * *